United States Patent
Ali et al.

(10) Patent No.: US 9,108,920 B2
(45) Date of Patent: *Aug. 18, 2015

(54) DIAZENIUMDIOLATE HETEROCYCLIC DERIVATIVES

(75) Inventors: Amjad Ali, Freehold, NJ (US); Michael Man-Chu Lo, Edison, NJ (US); Robert K. Baker, Cranford, NJ (US); Zhiqiang Guo, Morganville, NJ (US); Brent Whitehead, Morristown, NJ (US); Timothy J. Henderson, Edison, NJ (US); Edward Metzger, Somerset, NJ (US); Lin Yan, East Brunswick, NJ (US); Shrenik K. Shah, Metuchen, NJ (US); James Dellureficio, Millington, NJ (US); Jun Wang, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/881,929

(22) PCT Filed: Oct. 25, 2011

(86) PCT No.: PCT/US2011/057641
§ 371 (c)(1),
(2), (4) Date: Jul. 12, 2013

(87) PCT Pub. No.: WO2012/058203
PCT Pub. Date: May 3, 2012

(65) Prior Publication Data
US 2013/0289003 A1 Oct. 31, 2013

Related U.S. Application Data

(60) Provisional application No. 61/408,012, filed on Oct. 29, 2010, provisional application No. 61/549,821, filed on Oct. 21, 2011.

(51) Int. Cl.
| | | |
|---|---|---|
| A61K 31/655 | (2006.01) |
| C07D 207/12 | (2006.01) |
| C07D 211/44 | (2006.01) |
| C07D 205/04 | (2006.01) |
| C07D 207/16 | (2006.01) |
| C07D 207/273 | (2006.01) |
| C07D 307/20 | (2006.01) |
| C07D 309/12 | (2006.01) |
| C07D 401/04 | (2006.01) |
| C07D 401/12 | (2006.01) |
| C07D 403/04 | (2006.01) |
| C07D 403/10 | (2006.01) |
| C07D 413/04 | (2006.01) |
| C07D 413/10 | (2006.01) |
| C07D 417/04 | (2006.01) |

(52) U.S. Cl.
CPC ............ *C07D 211/44* (2013.01); *A61K 31/655* (2013.01); *C07D 205/04* (2013.01); *C07D 207/12* (2013.01); *C07D 207/16* (2013.01); *C07D 207/273* (2013.01); *C07D 307/20* (2013.01); *C07D 309/12* (2013.01); *C07D 401/04* (2013.01); *C07D 401/12* (2013.01); *C07D 403/04* (2013.01); *C07D 403/10* (2013.01); *C07D 413/04* (2013.01); *C07D 413/10* (2013.01); *C07D 417/04* (2013.01)

(58) Field of Classification Search
USPC .......... 514/149, 150; 534/551, 556; 544/336; 546/193, 242, 278.7; 548/132, 144, 548/364.1, 531, 950; 549/419, 475
See application file for complete search history.

(56) References Cited

U.S. PATENT DOCUMENTS

| | | | |
|---|---|---|---|
| 4,801,596 A | 1/1989 | Simon et al. | |
| 5,614,656 A | 3/1997 | Toda et al. | |
| 6,750,254 B2 | 6/2004 | Hrabie | |
| 7,348,319 B2 | 3/2008 | Hrabie et al. | |
| 7,468,435 B2 | 12/2008 | Waterhouse et al. | |
| 8,361,994 B2 * | 1/2013 | Ali et al. | 514/149 |
| 8,623,846 B2 * | 1/2014 | Ali et al. | 514/150 |

(Continued)

FOREIGN PATENT DOCUMENTS

| | | |
|---|---|---|
| WO | 9746521 A1 | 12/1997 |
| WO | 2007144512 A2 | 6/2007 |

(Continued)

OTHER PUBLICATIONS

Kadam et al. "Principles of medicinal chem . . . " vol. II, p. 403-404 (2007).*
Thornber "Isosterism . . . " Chem. Soc. Rev. vol. 8, 563-580 (1979).*
Piperidine Wikipedia p. 1-4 (2014).*
Leenen "Intermittent blodd pressure . . . " Can. J. Cardio. 15, suppl C:13C-18C (1999) abstract.*
Mancia et al. "Manual of hypertension of . . . " p. 232 (2008).*
Valdez et al; "Hydrolytic Reactivity Trends among Potential Prodrugs of the O2-Glycosylated Diazeniumdiolate Family. Targeting Nitric Oxide to Macrophages for Antileishmanial Activity"; Journal of Medicinal Chemistry, vol. 51; pp. 3961-3970, 3963, Compound 12 (2008).
Chakrapani, et al; "Nitric Oxide Prodrugs: Diazeniumdiolate Anions of Hindered Secondary Amines"; Organic Letters; vol. 9; pp. 4551-4554 (2007).

*Primary Examiner* — Celia Chang
(74) *Attorney, Agent, or Firm* — Nicole M. Beeler; Catherine D. Fitch

(57) ABSTRACT

A compound having the structure: useful for treating hypertension, Pulmonary Arterial Hypertension (PAH), congestive heart failure, conditions resulting from excessive water retention, cardiovascular disease, diabetes, oxidative stress, endothelial dysfunction, cirrhosis, pre-eclampsia, osteoporosis or nephropathy.

I

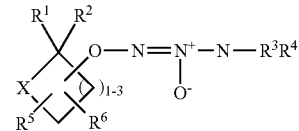

21 Claims, No Drawings

(56) References Cited

U.S. PATENT DOCUMENTS

| | | | |
|---|---|---|---|
| 8,648,058 B2* | 2/2014 | Ali et al. | 514/151 |
| 2005/0065194 A1 | 3/2005 | Shankar | |
| 2005/0137191 A1 | 6/2005 | Thatcher | |
| 2014/0088048 A1* | 3/2014 | Ali et al. | 514/150 |

FOREIGN PATENT DOCUMENTS

| | | |
|---|---|---|
| WO | 2009070241 A2 | 6/2009 |
| WO | 2009094242 A1 | 7/2009 |
| WO | 2009103875 A | 8/2009 |

* cited by examiner

DIAZENIUMDIOLATE HETEROCYCLIC DERIVATIVES

PRIORITY CLAIM

This application is a 371 of PCT/US11/057641, filed Oct. 25, 2011, which claims the benefit of U.S. Provisional Application Nos. 61/549,821, filed Oct. 21 2011, and 61/408,012, filed Oct. 29, 2010.

JOINT RESEARCH AGREEMENT

The claimed invention was made as a result of activities undertaken within the scope of a joint research agreement between Merck & Co., Inc. and NicOx SA. The agreement was executed on Mar. 20, 2006.

BACKGROUND OF THE INVENTION

WO09103875 describes diazeniumdiolate dihydro indole derivatives of a specified formula for treating hypertension and cardiovascular disease. WO07144512 describes diazeniumdiolate tetrazole-biphenyl derivatives of a specified formula for treating hypertension and cardiovascular disease. US 2005137191 describes nitrate ester compounds, e.g., 1,2-dichloro-4-(2-methyl-butyldisulfanyl)-benzene, useful for preventing or mitigating tissue and/or cellular damage associated with aging, septic shock, ulcers, gastritis, ulcerative colitis and Crohn's disease. US 2005065194 describes use of an endothelial gene differentiation receptor modulator such as 1-(2-ethoxyphenyl)-3-(hydroxyphenylamino)-pyrrolidine-2,5-dione, to modulate receptor-mediated biological activity such as cell proliferation stimulated by lysophosphatidic acid leading to ovarian cancer and other forms of cancer, and to treat conditions such as cancer, cardiovascular disease, ischemia, and atherosclerosis. WO 9746521 describes aliphatic nitrate esters useful for treating neurological conditions, especially Parkinson's, Alzheimer's and Huntington's disease.

The present invention relates to novel diazeniumdiolate heterocyclic derivatives, useful as antihypertensive agents.

SUMMARY OF THE INVENTION

The present invention includes diazeniumdiolate heterocyclic derivatives, including various pharmaceutically acceptable salts and hydrates of these forms, and pharmaceutical formulations comprising the diazeniumdiolate heterocyclic derivatives.

The invention also includes a method for treating hypertension, Pulmonary Arterial Hypertension (PAH), congestive heart failure, conditions resulting from excessive water retention, cardiovascular disease, diabetes, oxidative stress, endothelial dysfunction, cirrhosis, pre-eclampsia, osteoporosis or nephropathy, comprising administering a compounds of the invention to a patient having such a condition, or being at risk to having such condition.

DETAILED DESCRIPTION OF THE INVENTION AND PREFERRED EMBODIMENTS

The invention is a compound of formula I:

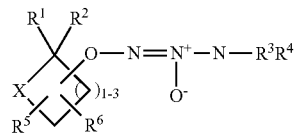

or a pharmaceutically acceptable salt thereof, wherein
$X$ is $O$ or $NR^7$;
$R^1$ is hydrogen, —C(O)O$C_{1-6}$alkyl, or —C(O)OH, or together with $R^2$, forms =O;
$R^2$ is hydrogen, or together with $R^1$, forms =O;
$R^3$ and $R^4$ are independently
—$C_{1-6}$alkyl,
—$C_{1-6}$alkylene-OH,
—$C_{1-6}$alkylene-C(O)OH,
—$C_{1-6}$alkylene-O—C(O)$C_{1-6}$alkyl,
—$C_{1-6}$alkylene-aryl, or
—CH$_2$CH=CH$_2$,
or, together with the nitrogen atom to which they are attached, form a 4- to 7-membered heterocyclic ring containing one nitrogen atom and 0 or 1 oxygen atoms, wherein said ring is unsubstituted or mono-, di- or tri-substituted with halogen, —$C_{1-6}$alkyl or $C_{1-6}$alkyl-OH;
$R^5$ and $R^6$, which are attached to any available carbon ring atom, are independently
hydrogen,
—$C_{1-6}$alkyl,
—C(O)O$C_{1-6}$alkyl,
—C(O)OH,
aryl,
or $R^5$ and $R^6$, when they are attached to the same carbon atom, together form =O;
$R^7$ is
hydrogen,
—$C_{1-6}$alkyl,
—$C_{1-6}$alkylene-aryl,
—$C_{1-6}$alkyleneC(O)O—$C_{1-6}$alkyl,
—$C_{1-6}$alkyleneC(O)OH,
—$C_{1-6}$alkyleneCF$_3$,
—CN,
—C(O)O—$C_{1-6}$alkyl,
—C(O)$C_{1-6}$alkyl,
—C(O)O$C_{3-6}$carbocycle,
—C(O)CHF$_2$,
—C(O)CHF$_3$,
—C(O)CH$_2$OH,
—C(O)aryl,
—C(O)$C_{1-6}$alkyleneOHC(O)$C_{3-6}$-carbocycle,
—C(O)NH$_2$,
—C(O)NH$C_{1-6}$alkyl,
—C(O)NH-aryl,
—C(O)heterocycle,
—C(O)NH$C_{3-6}$carbocycle,
—C(O)N($C_{1-6}$alkyl)$C_{1-6}$alkyl,
—C(O)NHSO$_2$aryl,
—SO$C_{1-6}$alkyl,
—SO$_2C_{1-6}$alkyl,
—SO$_2$CF$_3$, —SO₂aryl,
—SO₂heteroaryl,
aryl,
heteroaryl,
heterocycle, or
—C₃₋₆-carbocycle;
wherein aryl, alkyl, carbocycle, heteroaryl, and heterocycle are unsubstituted or substituted with 1, 2, 3 or 4 groups independently selected from $R^8$, where $R^8$ is independently —CN, halogen, CF₃, =O, —C(O)OC₁₋₆alkyl, —O—C₁₋₆alkyl, —OCF₃, —C₁₋₆alkyl, heteroaryl, —C(O)NH₂, or —O—N=N⁺(O⁻)N(CH₃)(C(CH₃)₃), and pharmaceutically acceptable salts thereof.

In one embodiment, the compound is of formula Ia, which is

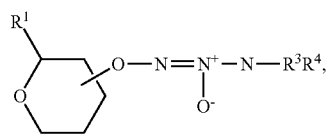

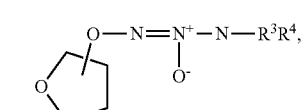

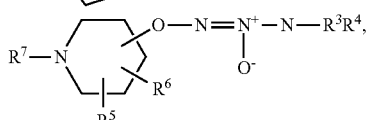

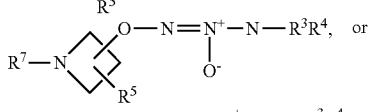

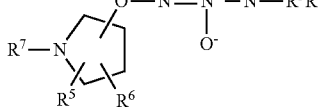

In another embodiment, the compound is of formula Ib, which is

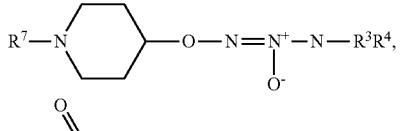

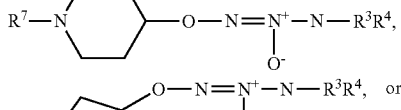

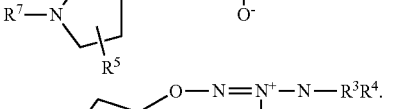

In another embodiment, $R^1$ together with $R^2$, forms =O.

In another embodiment, $R^7$ is hydrogen, —CH₃, —CH₂CF₃, —CH₂C₆H₅, —CH(CH₃)C₆H₅, —CH₂C(O)OH, —CH₂C(O)OCH₃, —CH(CH₃)C(O)OCH₂CH₃, —C(CH₃)₂C(O)OCH₂CH₃, —CH₂CH(CH₂CH₃)₂, —CH(CH₂CH₃)₂, —C(CH₃)₂C₆H₅, —C(CH₃)₃, —CN, —CH₂CH(CH₃)₂, or

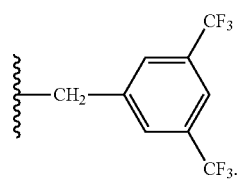

In another embodiment, $R^7$ is —C₆H₅,

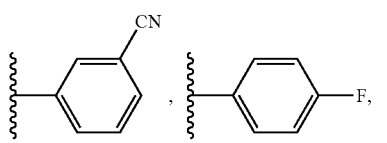

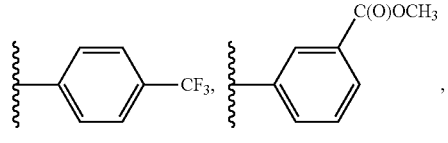

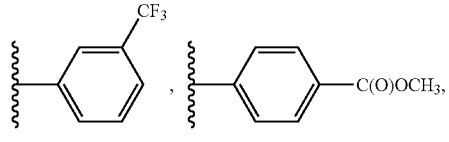

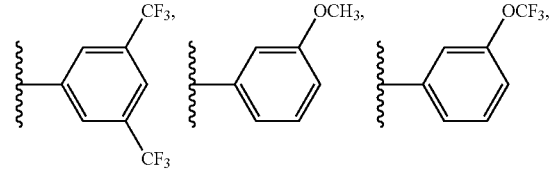

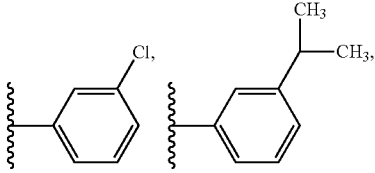

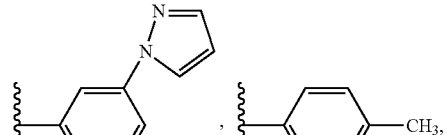

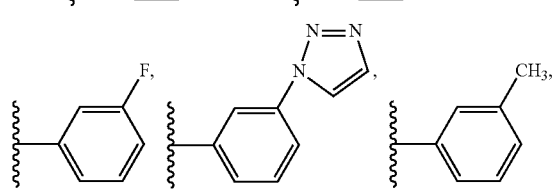

5

-continued

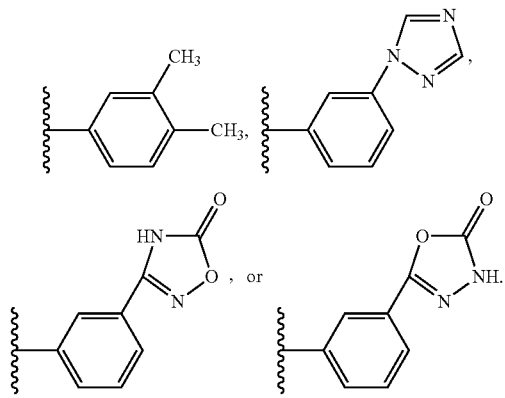

In another embodiment, R⁷ is

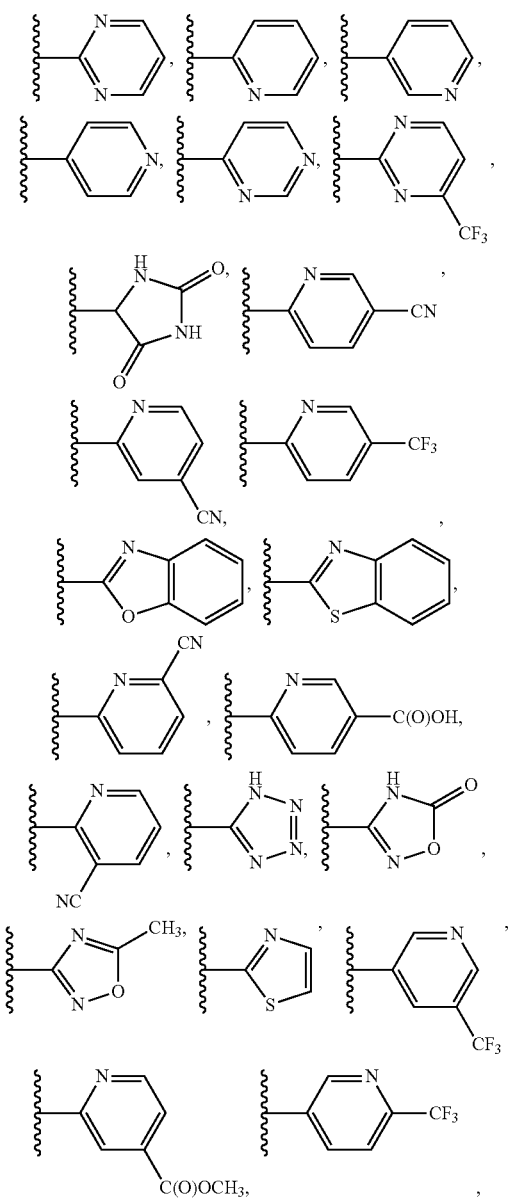

6

-continued

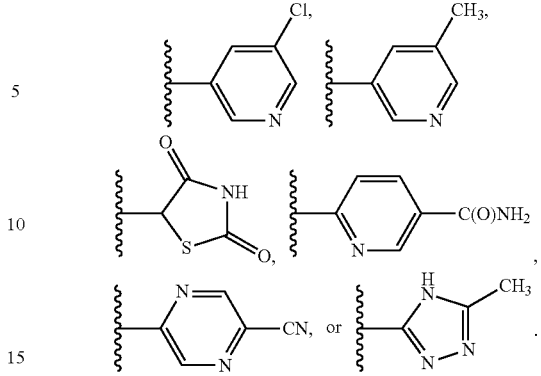

In another embodiment, $R^5$ and $R^6$ are attached to the same carbon atom and together form =O.

In another embodiment, $R^5$ and $R^6$ are independently hydrogen or deuterium.

In another embodiment, $R^3$ is —CD$_2$C$_{1-5}$alkyl, —C(CH$_3$)$_3$, —CH$_2$CH$_3$, or —CH(CH$_3$)$_2$.

In another embodiment, $R^4$ is —CD$_2$C$_{1-5}$alkyl, —CH$_3$, —CH$_2$CH$_3$, —CH$_2$CH$_2$CH$_3$, —CH$_2$CH$_2$CH$_2$CH$_3$, —CH$_2$CH$_2$-phenyl, —CH$_2$-phenyl, —CD$_2$CH$_3$, —CH$_2$CH$_2$OH, —CH$_2$C(O)OH, —CH$_2$CH$_2$OC(O)CH$_3$, —CH$_2$CH=CH$_2$.

In another embodiment, $R^3$ and $R^4$, together with the N atom to which they are attached, form a 5- or 6-membered heterocyclic ring containing 1 N atom, which ring is unsubstituted or substituted with —CH$_2$OH.

In another embodiment, compounds of the invention are
O²-[(3R)-1-(tert-butoxycarbonyl)pyrrolidin-3-yl]1-(N-tert-butyl-N-methylamino)diazen-1-ium-1,2-diolate,
O²-[(3S)-1-(tert-butoxycarbonyl)pyrrolidin-3-yl]1-(N-tert-butyl-N-methylamino)diazen-1-ium-1,2-diolate,
O²-[(3R)-1-(tert-butoxycarbonyl)pyrrolidin-3-yl]1-(N-tert-butyl-N-ethylamino)diazen-1-ium-1,2-diolate,
O²-[(3R)-1-(tert-butoxycarbonyl)pyrrolidin-3-yl]1-(N-tert-butyl-N-ethylamino)diazen-1-ium-1,2-diolate,
O²-[1-(tert-butoxycarbonyl)piperidin-4-yl]1-(N-tert-butyl-N-methylamino)diazen-1-ium-1,2-diolate,
O²-[1-(tert-butoxycarbonyl)piperidin-4-yl]1-(N-tert-butyl-N-ethylamino)diazen-1-ium-1,2-diolate,
O²-[1-(tert-butoxycarbonyl)piperidin-4-yl]1-(N,N-diethylamino)diazen-1-ium-1,2-diolate,
O²-[1-(tert-butoxycarbonyl)piperidin-4-yl]1-(N-tert-butyl-N-propylamino)diazen-1-ium-1,2-diolate,
O²-[1-(tert-butoxycarbonyl)piperidin-4-yl]1-(N-butyl-N-tert-butylamino)diazen-1-ium-1,2-diolate,
O²-[1-(tert-butoxycarbonyl)piperidin-4-yl]1-(N-tert-butyl-N-phenylethylamino)diazen-1-ium-1,2-diolate,
O²-[1-(tert-butoxycarbonyl)piperidin-4-yl]1-[N-tert-butyl-N-(2'-hydroxyethyl)amino]diazen-1-ium-1,2-diolate,
(±)-O²-[1-(tert-butoxycarbonyl)piperidin-3-yl]1-(N-tert-butyl-N-methylamino)diazen-1-ium-1,2-diolate,
O²-[1-(tert-butoxycarbonyl)azetidin-3-yl]1-(N-tert-butyl-N-methylamino)diazen-1-ium-1,2-diolate,
O²-[1-(tert-butoxycarbonyl)azetidin-3-yl]1-(N-tert-butyl-N-ethylamino)diazen-1-ium-1,2-diolate,
O²-[(3R)-pyrrolidin-3-yl]1-(N-tert-butyl-N-methylamino)diazen-1-ium-1,2-diolate,
O²-[(3R)-pyrrolidin-3-yl]1-(N-tert-butyl-N-ethylamino)diazen-1-ium-1,2-diolate,
O²-(piperidin-4-yl)1-(N-tert-butyl-N-ethylamino)diazen-1-ium-1,2-diolate, O²-[(3R)-1-(2-methylpropyl)pyrrolidin-3-yl]1-(N-tert-butyl-N-methylamino)diazen-1-ium-1,2-diolate,
O²-[(3R)-1-benzylpyrrolidin-3-yl]1-(N-tert-butyl-N-methylamino)diazen-1-ium-1,2-diolate,
(±)-O²-[(3R)-1-(1-phenylethyl)pyrrolidin-3-yl]1-(N-tert-butyl-N-methylamino)diazen-1-ium-1,2-diolate,
O²-[(3R)-1-(2-phenylpropan-2-yl)pyrrolidin-3-yl]1-(N-tert-butyl-N-methylamino)diazen-1-ium-1,2-diolate,
O²-[(3R)-1-tert-butylpyrrolidin-3-yl]1-(N-tert-butyl-N-methylamino)diazen-1-ium-1,2-diolate,
O²-(1-methylpiperidin-4-yl)1-(N-tert-butyl-N-ethylamino)diazen-1-ium-1,2-diolate,
O²-[(3R)-1-(2,2,2-trifluoroethyl)pyrrolidin-3-yl]1-(N-tert-butyl-N-ethylamino)diazen-1-ium-1,2-diolate,
O²-[1-(2,2,2-trifluorethyl)piperidin-4-yl]1-(N-tert-butyl-N-ethylamino)diazen-1-ium-1,2-diolate,
O²-(1-benzylpiperidin-4-yl)1-(N-tert-butyl-N-ethylamino)diazen-1-ium-1,2-diolate,
(±)-O²-[1-(1-phenylethyl)piperidin-4-yl]1-(N-tert-butyl-N-ethylamino)diazen-1-ium-1,2-diolate,
O²-[(3R)-1-phenylpyrrolidin-3-yl]1-(N-tert-butyl-N-methylamino)diazen-1-ium-1,2-diolate,
O²-[(3R)-1-(3-cyanophenyl)pyrrolidin-3-yl]1-(N-tert-butyl-N-methylamino)diazen-1-ium-1,2-diolate,
O²-{(3R)-1-[3-(methoxycarbonyl)phenyl]pyrrolidin-3-yl}1-(N-tert-butyl-N-methylamino)diazen-1-ium-1,2-diolate,
O²-{(3R)-1-[3-(trifluoromethyl)phenyl]pyrrolidin-3-yl}1-(N-tert-butyl-N-methylamino)diazen-1-ium-1,2-diolate,
O²-{(3R)-1-[3,5-bis(trifluoromethyl)phenyl]pyrrolidin-3-yl}1-(N-tert-butyl-N-methylamino)diazen-1-ium-1,2-diolate,
O²-[(3R)-1-(1,3-thiazol-2-yl)pyrrolidin-3-yl]1-(N-tert-butyl-N-methylamino)diazen-1-ium-1,2-diolate,
O²-[1-(pyridin-2-yl)piperidin-4-yl]1-(N-tert-butyl-N-methylamino)diazen-1-ium-1,2-diolate,
O²-[1-(pyridin-3-yl)piperidin-4-yl]1-(N-tert-butyl-N-methylamino)diazen-1-ium-1,2-diolate,
O²-(1-phenylpiperidin-4-yl)1-(N-tert-butyl-N-ethylamino)diazen-1-ium-1,2-diolate,
O²-[1-(3-cyanophenyl)piperidin-4-yl]1-(N-tert-butyl-N-ethylamino)diazen-1-ium-1,2-diolate,
O²-[1-(6-cyanopyridin-2-yl)piperidin-4-yl]1-(N-tert-butyl-N-ethylamino)diazen-1-ium-1,2-diolate,
O²-[1-(5-cyanopyridin-2-yl)piperidin-4-yl]1-(N-tert-butyl-N-ethylamino)diazen-1-ium-1,2-diolate,
O²-[1-(4-cyanopyridin-2-yl)piperidin-4-yl]1-(N-tert-butyl-N-ethylamino)diazen-1-ium-1,2-diolate,
O²-[1-(3-cyanopyridin-2-yl)piperidin-4-yl]1-(N-tert-butyl-N-ethylamino)diazen-1-ium-1,2-diolate,
O²-[(3R)-1-(tert-butylcarbamoyl)pyrrolidin-3-yl]1-(N-tert-butyl-N-methylamino)diazen-1-ium-1,2-diolate,
O²-[(3R)-1-(tert-butylcarbamoyl)pyrrolidin-3-yl]1-(N-tert-butyl-N-ethylamino)diazen-1-ium-1,2-diolate,
O²-{(3R)-2-oxo-1-[4-(trifluoromethyl)phenyl]pyrrolidin-3-yl}1-(N-tert-butyl-N-methylamino)diazen 1-ium-1,2-diolate,
O²-[(3R)-1-acetylpyrrolidin-3-yl]1-(N-tert-butyl-N-methylamino)diazen-1-ium-1,2-diolate,
O²-(1-acetylpiperidin-4-yl)1-(N-tert-butyl-N-ethylamino)diazen-1-ium-1,2-diolate,
O²-[1-(phenylcarbonyl)piperidin-4-yl]1-(N-tert-butyl-N-ethylamino)diazen-1-ium-1,2-diolate,
O²-[1-(hydroxyacetyl)piperidin-4-yl]1-(N-tert-butyl-N-ethylamino)diazen-1-ium-1,2-diolate,
O²-[1-(difluoroacetyl)piperidin-4-yl]1-(N-tert-butyl-N-ethylamino)diazen-1-ium-1,2-diolate,
O²-[1-(trifluoroacetyl)piperidin-4-yl]1-(N-tert-butyl-N-ethylamino)diazen-1-ium-1,2-diolate,
O²-[1-(phenylcarbonyl)azetidin-3-yl]1-(N-tert-butyl-N-methylamino)diazen-1-ium-1,2-diolate,
O²-[(3R)-1-(methylsulfonyl)pyrrolidin-3-yl]1-(N-tert-butyl-N-methylamino)diazen-1-ium-1,2-diolate,
O²-[(3R)-1-(tert-butylsulfonyl)pyrrolidin-3-yl]1-(N-tert-butyl-N-methylamino)diazen-1-ium-1,2-diolate,
O²-[(3R)-1-(2,2,2-trifluoroethyl)pyrrolidin-3-yl]1-(N-tert-butyl-N-methylamino)diazen-1-ium-1,2-diolate,
O²-[(3R)-2-oxo-1-(2,2,2-trifluoroethyl)pyrrolidin-3-yl]1-(N-tert-butyl-N-methylamino)diazen-1-ium-1,2-diolate,
O²-[(3R)-5-oxo-1-(2,22-trifluoroethyl)pyrrolidin-3-yl]1-(N-tert-butyl-N-methylamino)diazen-1-ium-1,2-diolate,
(±)-O²-[1-(5-cyanopyridin-2-yl)-2-oxopiperidin-A-yl]1-(N-tert-butyl-N-ethylamino)diazen 1-ium-1,2-diolate,
O²-[(3S)-tetrahydrofuran-3-yl]1-(N-tert-butyl-N-ethylamino)diazen-1-ium-1,2-diolate,
O²-[(3R)-tetrahydrofuran-3-yl]1-(N-tert-butyl-N-ethylamino)diazen-1-ium-1,2-diolate,
O²-(tetrahydro-2H-pyran-4-yl)1-(N-tert-butyl-N-ethylamino)diazen-1-ium-1,2-diolate,
O²-(tetrahydro-2H-pyran-4-yl)1-(N-tert-butyl-N-methylamino)diazen-1-ium-1,2-diolate,
O²-[(3R,5S)-1-(tert-butoxycarbonyl)-5-(methoxycarbonyl)pyrrolidin-3-yl]1-(N-tert-butyl-N-ethylamino)diazen-1-ium-1,2-diolate,
O²-[(3R,5S)-5-(methoxycarbonyl)pyrrolidin-3-yl]1-(N-tert-butyl-N-ethylamino)diazen-1-ium-1,2-diolate,
O²-[(3R,5S)-5-carboxypyrrolidin-3-yl]1-(N-tert-butyl-N-ethylamino)diazen-1-ium-1,2-diolate,
O²-[1-(2-methoxy-2-oxoethyl)piperidin-4-yl]1-(N-tert butyl-N-ethylamino)diazen-1-ium-1,2-diolate,
O²-[1-(carboxymethyl)piperidin-4-yl]1-(N-tert-butyl-N-ethylamino)diazen-1-ium-1,2-diolate,
(±)-O²-[1-(2,4-dioxo-1,3-thiazolidin-5-yl)piperidin-4-yl]1-(N-tert-butyl-N-ethylamino)diazen-1-ium-1,2-diolate,
O²-[1-(2,5-dioxoimidazolidin-4-yl)piperidin-4-yl]1-(N-tert-butyl-N-ethylamino)diazen-1-ium-1,2-diolate,
O²-[1-(1-ethoxy-2-methyl-1-oxopropan-2-yl)piperidin-4-yl]1-(N-tert-butyl-N-ethylamino)diazen-1-ium-1,2-diolate,
O²-[1-(5-carbamoylpyridin-2-yl)piperidin-4-yl]1-(N-tert-butyl-N-ethylamino)diazen-1-ium-1,2-diolate,
O²-[(3R)-1-(5-cyanopyrazin-2-yl)pyrrolidin-3-yl]1-(N-tert-butyl-N-methylamino)diazen-1-ium-1,2-diolate,
O²-{(3R)-1-[3-(1H-pyrazol-1-yl)phenyl]pyrrolidin-3-yl}1-(N-tert-butyl-N-methylamino)diazen-1-ium-1,2-diolate,
O²-{(3R)-1-[3-(1H-1,2,4-triazol-1-yl)phenyl]pyrrolidin 3-yl}1-(N-tert-butyl-N-methylamino)diazen-1-ium-1,2-diolate,
O²-{(3R)-1-[3-(1H-1,2,3-triazol-1-yl)phenyl]pyrrolidin-3-yl}1-(N-tert-butyl-N-methylamino)diazen-1-ium-1,2-diolate,
O¹-{(3R)-1-[3-(5-oxo-4,5-dihydro-1,2,4-oxadiazol-3-yl)phenyl]pyrrolidin-3-yl}1-(N-tert-butyl-N-methylamino)diazen-1-ium-1,2-diolate,
O²-{(3R)-1-[3-(5-oxo-4,5-dihydro-1,3,4-oxadiazol-2-yl)phenyl]pyrrolidin-3-yl}1-(N-tert-butyl-N-methylamino)diazen-1-ium-1,2-diolate,
O²-[(3R)-1-cyanopyrrolidin-3-yl]1-(N-tert-butyl-N-methylamino)diazen-1-ium-1,2-diolate,
O²-[(3R)-1-(5-methyl-1,2,4-oxadiazol-3-yl)pyrrolidin-3-yl]1-(N-tert-butyl-N-methylamino)diazen-1-ium-1,2-diolate, O²-[(3R)-1-(5-methyl-4H-1,2,4-triazol-3-yl)pyrrolidin-3-yl]1-(N-tert-butyl-N-methylamino)diazen-1-ium-1,2-diolate,
O²-[(3R)-1-(5-oxo-4,5-dihydro-1,2,4-oxadiazol-3-yl)pyrrolidin-3-yl]1-(N-tert-butyl-N-methylamino)diazen-1-ium-1,2-diolate,
O²-[(3R)-1-(1H-tetrazol-5-yl)pyrrolidin-3-yl]1-(N-tert-butyl-N-methylamino)diazen-1-ium-1,2-diolate,
O²-[(3R)-1-carbamoylpyrrolidin-3-yl]1-(N-tert-butyl-N-methylamino)diazen-1-ium-1,2-diolate,
O²-{(3R)-1-[tert-butyl(methyl)carbamoyl]pyrrolidin-3-yl}1-(N-tert-butyl-N-methylamino)diazen-1-ium-1,2-diolate,
O²-{(3R)-1-[(3-cyanophenyl)carbamoyl]pyrrolidin-3-yl}1-(N-tert-butyl-N-methylamino)diazen-1-ium-1,2-diolate,
1,1'-carbonylbis{O²-[(3R)-pyrrolidin-3-yl]1-(N-tert-butyl-N-methylamino)diazen-1-ium-1,2-diolate},
O²-[(3R)-1-(ter-butylcarbamoyl)pyrrolidin-3-yl]1-(N-(tert-butyl-N-propylamino)diazen-1-ium-1,2-diolate,
O²-[(3R)-1-(tert-butylcarbamoyl)pyrrolidin-3-yl]1-(N-tert-butyl-N-allylamino)diazen-1-ium-1,2-diolate,
O²-[(3R)-1-(tert-butylcarbamoyl)pyrrolidin-3-yl]1-[N-tert-butyl-N-(2'-hydroxyethyl)amino]diazen-1-ium-1,2-diolate,
O²-[(3R)-1-(tert-butylcarbamoyl)pyrrolidin-3-yl]1-[N-tert-butyl-N-(carboxymethyl)amino]diazen-1-ium-1,2-diolate,
O²-[(3R)-1-(tert-butylcarbamoyl)pyrrolidin-3-yl]1-(N-benzyl-N-isopropylamino)diazen-1-ium-1,2-diolate,
O²-[(3R)-1-(tert-butylcarbamoyl)pyrrolidin-3-yl]1-(N-benzyl-N-butylamino)diazen-1-ium-1,2-diolate,
O²-[(3R)-1-(tert-butylcarbamoyl)pyrrolidin-3-yl]1-(pyrrolidin-1-yl)diazen-1-ium-1,2-diolate,
O²-[(3R)-1-(tert-butylcarbamoyl)pyrrolidin-3-yl]1-(piperidin-1-yl)diazen-1-ium-1,2-diolate,
O²-[(3R)-1-(tert-butylcarbamoyl)pyrrolidin-3-yl]1-[2-(hydroxymethyl)piperidin-1-yl]diazen-1-ium-1,2-diolate,
O²-[(3R)-1-(2-ethylbutyl)pyrrolidin-3-yl]1-(N-tert-butyl-N-methylamino)diazen-1-ium-1,2-diolate (example 19)
O²-[(3R)-1-(pentan-3-yl)pyrrolidin-3-yl]1-(N-tert-butyl-N-methylamino)diazen-1-ium-1,2-diolate (example 20),
O²-[(3R)-1-(heptan-4-yl)pyrrolidin-3-yl]1-(N-tert-butyl-N-methylamino)diazen-1-ium-1,2-diolate (example 21),
O²-[(3R)-1-cyclopentylpyrrolidin-3-yl]1-(N-tert-butyl-N-methylamino)diazen-1-ium-1,2-diolate (example 22),
O²-[(3R)-1-cyclohexylpyrrolidin-3-yl]1-(N-tert-butyl-N-methylamino)diazen-1-ium-1,2-diolate (example 23),
O²-[1-(2-ethylbutyl)piperidin-4-yl]1-(N-tert-butyl-N-ethylamino)diazen-1-ium-1,2-diolate (example 24),
O²-[1-(pentan-3-yl)piperidin-4-yl]1-(N-tert-butyl-N-ethylamino)diazen-1-ium-1,2-diolate (example 25),
O²-(1-cyclopentylpiperidin-4-yl)1-(N-tert-butyl-N-ethylamino)diazen-1-ium-1,2-diolate (example 26),
O²-(1-cyclohexylpiperidin-4-yl)1-(N-tert-butyl-N-ethylamino)diazen-1-ium-1,2-diolate (example 27),
O²-{(3R)-2-oxo-1-[5-(trifluoromethyl)pyridin-2-yl]pyrrolidin-3-yl}1-(N-tert-butyl-N-methylamino)diazen-1-ium-1,2-diolate (example 63),
O²-[(3R)-1-(3-methoxyphenyl)-2-oxopyrrolidin-3-yl]1-(N-tert-butyl-N-methylamino)diazen-1-ium-1,2-diolate (example 64),
O²-{(3R)-2-oxo-1-[3-(trifluoromethyl)phenyl]pyrrolidin-3-yl}1-(N-tert-butyl-N-methylamino)diazen-1-ium-1,2-diolate (example 65),
O²-{(3R)-1-[3,5-bis(trifluoromethyl)phenyl]-2-oxopyrrolidin-3-yl}1-(N-tert-butyl-N-methylamino)diazen-1-ium-1,2-diolate (example 66),
O²-[(3R)-1-(3-cyanophenyl)-2-oxopyrrolidin-3-yl]1-(N-tert-butyl-N-methylamino)diazen-1-ium-1,2-diolate (example 67),
O²-[(3R)-2-oxopyrrolidin-3-yl]1-(N-tert-butyl-N-methylamino)diazen-1-ium-1,2-diolate (example 68),
O²-[(3R)-1-benzyl-2-oxopyrrolidin-3-yl]1-(N-tert-butyl-N-methylamino)diazen-1-ium-1,2-diolate (example 69),
O²-{(3R)-2-oxo-1-[3-(trifluoromethoxy)phenyl]pyrrolidin-3-yl}1-(N-tert-butyl-N-methyl amino)diazen-1-ium-1,2-diolate (example 70),
O²-[(3R)-1-(3-chlorophenyl)-2-oxopyrrolidin-3-yl]1-(N-tert-butyl-N-methylamino)diazen-1-ium-1,2-diolate (example 71),
O²-{(3R)-2-oxo-1-[3-propan-2-yl)phenyl]pyrrolidin-3-yl}1-(N-tert-butyl N-methylamino)diazen-1-ium-1,2-diolate (example 72),
O²-{(3R)-2-oxo-1-[6-(trifluoromethyl)pyridin-3-yl]pyrrolidin-3-yl}1-(N-tert-butyl-N-methylamino)diazen-1-ium-1,2-diolate (example 73),
O²-{(3R)-2-oxo-1-[3-(1H-pyrazol-1-yl)phenyl]pyrrolidin-3-yl}1-(N-tert-butyl-N-methylamino)diazen-1-ium-1,2-diolate (example 74),
O²-[(3R)-1-(4-methylphenyl)-2-oxopyrrolidin-3-yl]1-(N-tert-butyl-N-methylamino)diazen-1-ium-1,2-diolate (example 75),
O²-[(3R)-1-(3-fluorophenyl)-2-oxopyrrolidin-3-yl]1-(N-tert-butyl N-methylamino)diazen-1-ium-1,2-diolate (example 76),
O²-{(3R)-2-oxo-1-[3-(1H-1,2,3-triazol-1-yl)phenyl]pyrrolidin-3-yl}1-(N-tert-butyl-N-methylamino)diazen-1-ium-1,2-diolate (example 77),
O²-[(3R)-1-(5-cyanopyridin-2-yl)-2-oxopyrrolidin-3-yl]1-(N-tert-butyl-N-methylamino)diazen-1-ium-1,2-diolate (example 78),
O²-{(3R)-2-oxo-1-[4-(trifluoromethyl)phenyl]pyrrolidin-3-yl}1-N-tert-butyl N-ethylamino)diazen-1-ium-1,2-diolate (example 79),
O²-[(3R)-1-(3-methylphenyl)-2-oxopyrrolidin-3-yl]1-(N-tert-butyl-N-ethylamino)diazen-1-ium-1,2-diolate (example 80),
O²-[(3R)-1-(5-chloropyridin-3-yl)-2-oxopyrrolidin-3-yl]1-(N-tert-butyl N-ethylamino)diazen-1-ium-1,2-diolate (example 81),
O²-{(3R)-2-oxo-1-[3-(1H-pyrazol-1-yl)phenyl]pyrrolidin-3-yl}1-(N-tert-butyl-N-ethylamino)diazen-1-ium-1,2-diolate (example 82),
O²-[(3R)-1-(5-methylpyridin-3-yl)-2-oxopyrrolidin-3-yl]1-(N-ter-butyl-N-ethylamino)diazen-1-ium-1,2-diolate (example 83),
O²-[(3R)-1-(3,4-dimethylphenyl)-2-oxopyrrolidin-3-yl]1-(N-tert-butyl-N-ethylamino)diazen-1-ium-1,2-diolate (example 84),
O²-{(3R)-2-oxo-1-[5-(trifluoromethyl)pyridin-3-yl]pyrrolidin-3-yl}1-(N-tert-butyl-N-ethylamino)diazen-1-ium-1,2-diolate (example 85), or
O²-{(3R)-2-oxo-1-[3-(1H-1,2,3-triazol-1-yl)phenyl]pyrrolidin-3-yl}1-(N-tert-butyl-N-ethylamino)diazen-1-ium-1,2-diolate (example 86).

In another embodiment, the compound is of formula Ii:

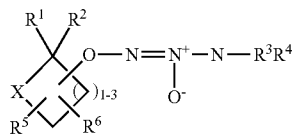

or a pharmaceutically acceptable salt thereof, wherein
X is O or NR$^7$;
R$^1$ is hydrogen, —C(O)OC$_{1-6}$alkyl, or —C(O)OH, or together with R$^2$, forms =O;
R$^2$ is hydrogen, or together with R$^1$, forms =O;
R$^3$ and R$^4$ are independently
- —C$_{1-6}$alkyl,
- —CD$_2$C$_{1-5}$-alkyl,
- —C$_{2-5}$alkylene-OH,
- —C$_{2-5}$alkylene-O—C(O)C$_{1-6}$alkyl,
- —C$_{1-6}$alkylene-aryl, or
- —CH$_2$CH=CH$_2$,
- or, together with the nitrogen atom to which they are attached, form a 4- to 7-membered heterocyclic ring containing one nitrogen atom and 0 or 1 oxygen atoms, wherein said ring is unsubstituted or mono-, di- or tri-substituted with halogen or —C$_{1-6}$alkyl;

R$^5$ and R$^6$, which are attached to any available carbon ring atom, are independently
- hydrogen,
- deuterium,
- —C$_{1-6}$alkyl,
- —C(O)OC$_{1-6}$alkyl,
- —C(O)OH,
- aryl,
- or R$^5$ and R$^6$, when they are attached to the same carbon atom, together form =O;

R$^7$ is
- hydrogen,
- —C$_{1-6}$alkyl,
- —C$_{1-6}$alkylene-aryl,
- —C$_{1-6}$alkyleneC(O)O—C$_{1-6}$alkyl,
- —C$_{1-6}$alkyleneCF$_3$,
- —CN,
- —C(O)O—C$_{1-6}$alkyl,
- —C(O)C$_{1-6}$alkyl,
- —C(O)OC$_{3-6}$carbocycle,
- —C(O)CHF$_2$,
- —C(O)CHF$_3$,
- —C(O)CH$_2$OH,
- —C(O)aryl,
- —C(O)C$_{1-6}$alkyleneOHC(O)C$_{3-6}$carbocycle,
- —C(O)NH$_2$,
- —C(O)NHC$_{1-6}$alkyl,
- —C(O)heterocycle,
- —C(O)NHC$_{3-6}$carbocycle,
- —C(O)N(C$_{1-6}$alkyl)C$_{1-6}$alkyl,
- —C(O)NHSO$_2$aryl,
- —SOC$_{1-6}$alkyl,
- —SO$_2$C$_{1-6}$alkyl,
- —SO$_2$CF$_3$,
- —SO$_2$aryl,
- —SO$_2$heteroaryl,
- aryl,
- heteroaryl,
- heterocycle, or
- —C$_{3-6}$carbocycle;
wherein aryl, alkyl, carbocycle, heteroaryl, and heterocycle are unsubstituted or substituted 3 or 4 groups independently selected from —CN, halogen, —CF$_3$, =O, —C(O)OC$_{1-6}$alkyl or —O—C$_{1-6}$alkyl;
and pharmaceutically acceptable salts thereof.

In another embodiment, the compound is of formula Iai, which is

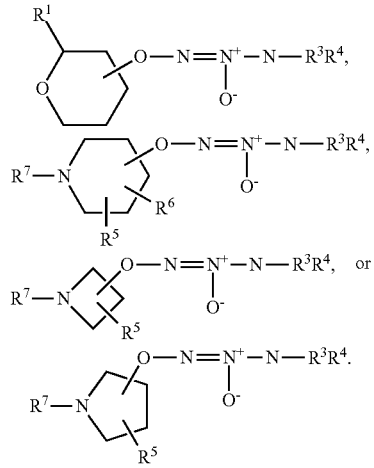

In another embodiment, the compound is of formula Ibi, which is

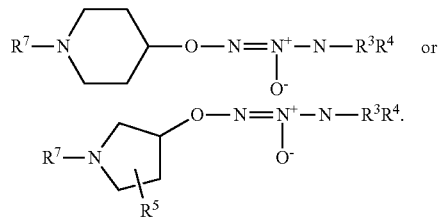

In another embodiment, R$^1$ is hydrogen, —C(O)OH, or —C(O)OCH$_3$.

In another embodiment, R$^2$ is hydrogen.

In another embodiment, R$^7$ is
hydrogen, —CH$_3$, —CH$_2$CF$_3$, —CH$_2$C$_6$H$_5$, —CH(CH$_3$)C$_6$H$_5$, —CH(CH$_3$)C(O)OCH$_2$CH$_3$, —CH$_2$CH(CH$_2$CH$_3$)$_2$, —CH(CH$_2$CH$_3$)$_2$, —C(CH$_3$)$_2$C$_6$H$_5$, —C(CH$_3$)$_3$, —CN, —CH$_2$CH(CH$_3$)$_2$, or

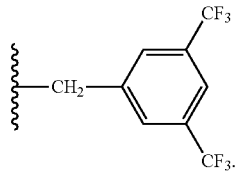

In another embodiment, R$^7$ is
—C(O)OC(CH$_3$)$_3$, —C(O)CH$_3$, —C(O)CF$_3$, —C(O)OCH$_2$CH$_3$, —C(O)OC$_6$H$_{11}$, —C(O)CHF$_2$, —C(O)C$_6$H$_5$, —C(O)CH$_2$OH, —C(O)C$_3$H$_5$, —C(O)C(CH$_3$)$_3$, —C(O)NH$_2$, —C(O)NHC(CH$_3$)$_3$, —C(O)NHC$_6$H$_{11}$, —C(O)N(CH$_3$)C(CH$_3$)$_3$, —C(O)SC(CH$_3$)$_3$, —C(O)NHSO$_2$C$_6$H$_5$,

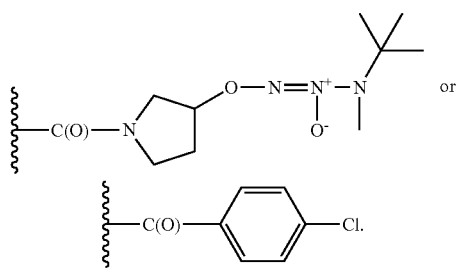

In another embodiment, R$^7$ is
—SO$_2$CH$_3$, —SO$_2$C$_6$H$_5$, —SO$_2$C(CH$_3$)$_3$, —SOC(CH$_3$)$_3$, —SO$_2$CF$_3$,

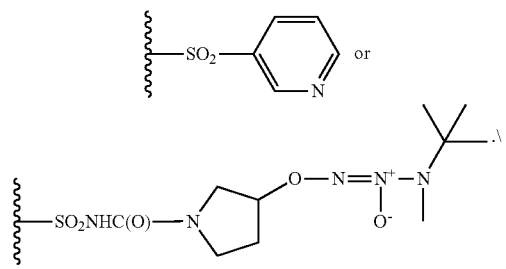

In another embodiment, R$^7$ is
—C$_6$H$_5$,

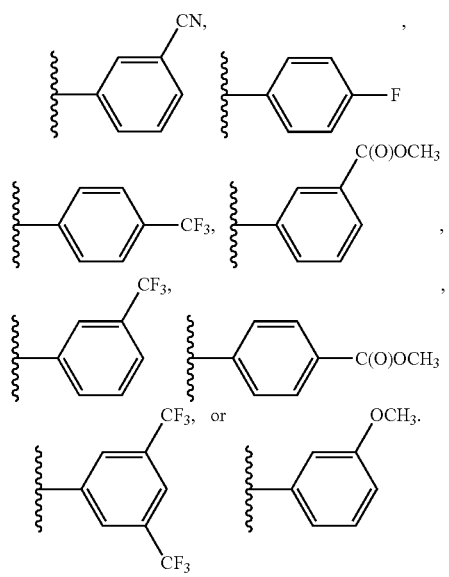

In another embodiment, R$^7$ is

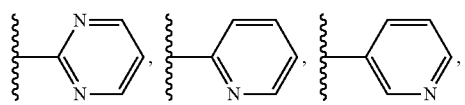

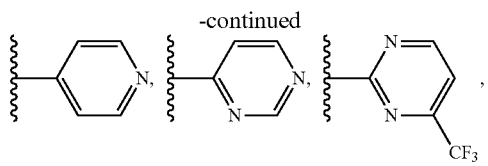

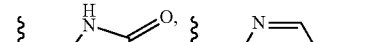
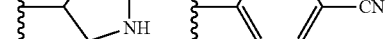
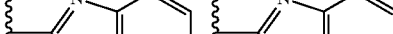
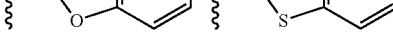
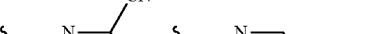
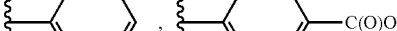
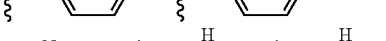
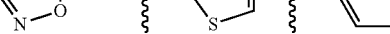

In another embodiment, R$^7$ is —CH$_1$ or —C$_5$H$_9$.
In another embodiment, R$^5$ is hydrogen, —CH$_3$, —C(O)OCH$_3$, —C(O)OH, or phenyl.
In another embodiment, R$^5$ and R$^6$ together form =O.
In another embodiment, R$^6$ is hydrogen or —CH$_3$.
In another embodiment, R$^3$ is —C(CH$_3$)$_3$ or —CH$_2$CH$_3$.
In another embodiment, R$^4$ is —CH$_3$, —CH$_2$CH$_3$, —CH$_2$CH$_2$CH$_3$, —CH$_2$CH$_2$CH$_2$CH$_3$, —CH$_2$CH$_2$-phenyl, —CD$_2$CH$_3$, —CH$_2$CH$_2$OH, or —CH$_2$CH$_2$OC(O)CH$_3$.
In another embodiment, compounds of the invention are
O$^2$-[(3R)-1-(tert-butoxycarbonyl)pyrrolidin-3-yl]1-(N-tert-butyl-N-methylamino)diazen-1-ium-1,2-diolate,
O$^2$-[(3S)-1-(tert-butoxycarbonyl)pyrrolidin-3-yl]1-(N-tert-butyl-N-methylamino)diazen-1-ium-1,2-diolate,
O$^2$-[(3R)-1-(tert-butoxycarbonyl)pyrrolidi-3-yl]1-(N-tert-butyl N-ethylamino)diazen-1-ium-1,2-diolate,
O$^2$-[(3R)-1-(tert-butoxycarbonyl)pyrrolidin-3-yl]1-(N-tert-butyl-N-ethylamino)diazen-1-ium-1,2-diolate,
O$^2$-[1-(tert-butoxycarbonyl)piperidin-4-yl]1-(N-tert-butyl-N-methylamino)diazen-1-ium-1,2-diolate,
O$^2$-[1-(tert-butoxycarbonyl)piperidin-4-yl]1-(N-tert-butyl-N-ethylamino)diazen-1-ium-1,2-diolate,
O$^2$-[1-(tert-butoxycarbonyl)piperidin-4-yl]1-(N,N-diethylamino)diazen-1-ium-1,2-diolate, O²-[1-(tert-butoxycarbonyl)piperidin-4-yl]1-(N-tert-butyl-N-propylamino)diazen-1-ium-1,2-diolate,
O²-[1-(tert-butoxycarbonyl)piperidin-4-yl]1-(N-butyl-N-tert-butylamino)diazen-1-ium-1,2-diolate,
O²-[1-(tert-butoxycarbonyl)piperidin-4-yl]1-(N-tert-butyl-N-phenylethylamino)diazen-1-ium-1,2-diolate,
O²-[1-(tert-butoxycarbonyl)piperidin-4-yl]1-[N-tert-butyl-N-(2'-hydroxyethyl)amino]diazen-1-ium-1,2-diolate,
(±)-O²-[1-(tert-butoxycarbonyl)piperidin-3-yl]1-(N-tert-butyl-N-methylamino)diazen-1-ium-1,2-diolate,
O²-[1-(tert-butoxycarbonyl)azetidin-3-yl]1-(N-tert-butyl-N-methylamino)diazen-1-ium-1,2-diolate,
O²-[1-(tert-butoxycarbonyl)azetidin-3-yl]1-(N-tert-butyl-N-ethylamino)diazen-1-ium-1,2-diolate,
O²-[(3R)-pyrrolidin-3-yl]1-(N-tert-butyl-N-methylamino)diazen-1-ium-1,2-diolate,
O²-[(3R)-pyrrolidin-3-yl]1-(N-tert-butyl-N-ethylamino)diazen-1-ium-1,2-diolate,
O²-(piperidin-4-yl)1-(N-tert-butyl-N-ethylamino)diazen-1-ium-1,2-diolate,
O²-[(3R)-1-(2-methylpropyl)pyrrolidin-3-yl]1-(N-tert-butyl-N-methylamino)diazen-1-ium-1,2-diolate,
O²-[(3R)-1-benzylpyrrolidin-3-yl]1-(N-tert-butyl-N-methylamino)diazen-1-ium-1,2-diolate,
(±)-O²-[(3R)-1-(1-phenylethyl)pyrrolidin-3-yl]1-(N-tert-butyl-N-methylamino)diazen-1-ium-1,2-diolate,
O²-[(3R)-1-(2-phenylpropan-2-yl)pyrrolidin-3-yl]1-(N-tert-butyl-N-methylamino)diazen-1-ium-1,2-diolate,
O²-[(3R)-1-tert-butylpyrrolidin-3-yl]1-(N-tert-butyl-N-methylamino)diazen-1-ium-1,2-diolate,
O²-(1-methylpiperidin-4-yl)1-(N-tert-butyl-N-ethylamino)diazen-1-ium-1,2-diolate,
O²-[(3R)-1-(2,2,2-trifluoroethyl)pyrrolidin-3-yl]1-(N-tert-butyl-N-ethylamino)diazen-1-ium-1,2-diolate,
O²-[1-(2,2,2-trifluoroethyl)piperidin-4-yl]1-(N-tert-butyl-N-ethylamino)diazen-1-ium-1,2-diolate,
O²-(1-benzylpiperidin-4-yl)1-(N-tert-butyl-N-ethylamino)diazen-1-ium-1,2-diolate,
(±)-O²-[1-(1-phenylethyl)piperidin-4-yl]1-(N-tert-butyl-N-ethylamino)diazen-1-ium-1,2-diolate,
O²-[(3R)-1-phenylpyrrolidin-3-yl]1-(N-ter-butyl-N-methylamino)diazen-1-ium-1,2-diolate,
O²-[(3R)-1-(3-cyanophenyl)pyrrolidin-3-yl]1-(N-tert-butyl-N-methylamino)diazen-1-ium-1,2-diolate,
O²-{(3R)-1-[3-(methoxycarbonyl)phenyl]pyrrolidin-3-yl}1-(N-tert-butyl-N-methylamino)diazen-1-ium-1,2-diolate,
O²-{(3R)-1-[3-(trifluoromethyl)phenyl]pyrrolidin-3-yl}1-(N-tert-butyl-N-methylamino)diazen-1-ium-1,2-diolate,
O²-{(3R)-1-[3,5-bis(trifluoromethyl)phenyl]pyrrolidin-3-yl}1-(N-tert-butyl-N-methylamino)diazen-1-ium-1,2-diolate,
O²-[(3R)-1-(1,3-thiazol-2-yl)pyrrolidin-3-yl]1-(N-tert-butyl-N-methylamino)diazen-1-ium-1,2-diolate,
O²-[1-(pyridin-2-yl)piperidin-4-yl]1-(N-tert-butyl-N-methylamino)diazen-1-ium-1,2-diolate,
O²-[1-(pyridin-3-yl)piperidin-4-yl]1-(N-tert-butyl-N-methylamino)diazen-ium-1,2-diolate,
O²-(1-phenylpiperidin-4-yl)1-(N-tert-butyl-N-ethylamino)diazen-1-ium-1,2-diolate,
O²-[1-(3-cyanophenyl)piperidin-4-yl]1-(N-tert-butyl-N-ethylamino)diazen-1-ium-1,2-diolate,
O²-[1-(6-cyanopyridin-2-yl)piperidin-4-yl]1-(N-tert-butyl-N-ethylamino)diazen-1-ium-1,2-diolate,
O²-[1-(5-cyanopyridin-2-yl)piperidin-4-yl]1-(N-tert-butyl-N-ethylamino)diazen-1-ium-1,2-diolate,
O²-[1-(4-cyanopyridin-2-yl)piperidin-4-yl]1-(N-tert-butyl-N-ethylamino)diazen-1-ium-1,2-diolate,
O²-[1-(3-cyanopyridin-2-yl)piperidin-4-yl]1-(N-tert-butyl-N-ethylamino)diazen-1-ium-1,2-diolate,
O²-[(3R)-1-(tert-butylcarbamoyl)pyrrolidin-3-yl]1-(N-tert-butyl-N-methylamino)diazen-1-ium-1,2-diolate,
O²-[(3R)-1-(tert-butylcarbamoyl)pyrrolidin-3-yl]1-(N-tert-butyl-N-ethylamino)diazen-1-ium-1,2-diolate,
O²-{(3R)-2-oxo-1-[4-(trifluoromethyl)phenyl]pyrrolidin-3-yl}1-(N-tert-butyl-N-methylamino)diazen-1-ium-1,2-diolate,
O²-[(3R)-1-acetylpyrrolidin-3-yl]1-(N-tert-butyl-N-methylamino)diazen-1-ium-1,2-diolate,
O²-(1-acetylpiperidin-4-yl)1-(N-tert-butyl-N-ethylamino)diazen-1-ium-1,2-diolate,
O²-[1-(phenylcarbonyl)piperidin-4-yl]1-(N-tert-butyl-N-ethylamino)diazen-1-ium-1,2-diolate,
O²-[1-(hydroxyacetyl)piperidin-4-yl]1-(N-tert-butyl-N-ethylamino)diazen-1-ium-1,2-diolate,
O²-[1-(difluoroacetyl)piperidin-4-yl]1-(N-tert-butyl-N-ethylamino)diazen-1-ium-1,2-diolate,
O²-[1-(trifluoroacetyl)piperidin-4-yl]1-(N-tert-butyl-N-ethylamino)diazen-1-ium-1,2-diolate,
O²-[1-(phenylcarbonyl)azetidin-3-yl]1-(N-tert-butyl-N-methylamino)diazen-1-ium-1,2-diolate,
O²-[(3R)-1-(methylsulfonyl)pyrrolidin-3-yl]1-(N-tert-butyl-N-methylamino)diazen-1-ium-1,2-diolate,
O²-[(3R)-1-(tert-butylsulfonyl)pyrrolidin-3-yl]1-(N-tert-butyl-N-methylamino)diazen-1-ium-1,2-diolate,

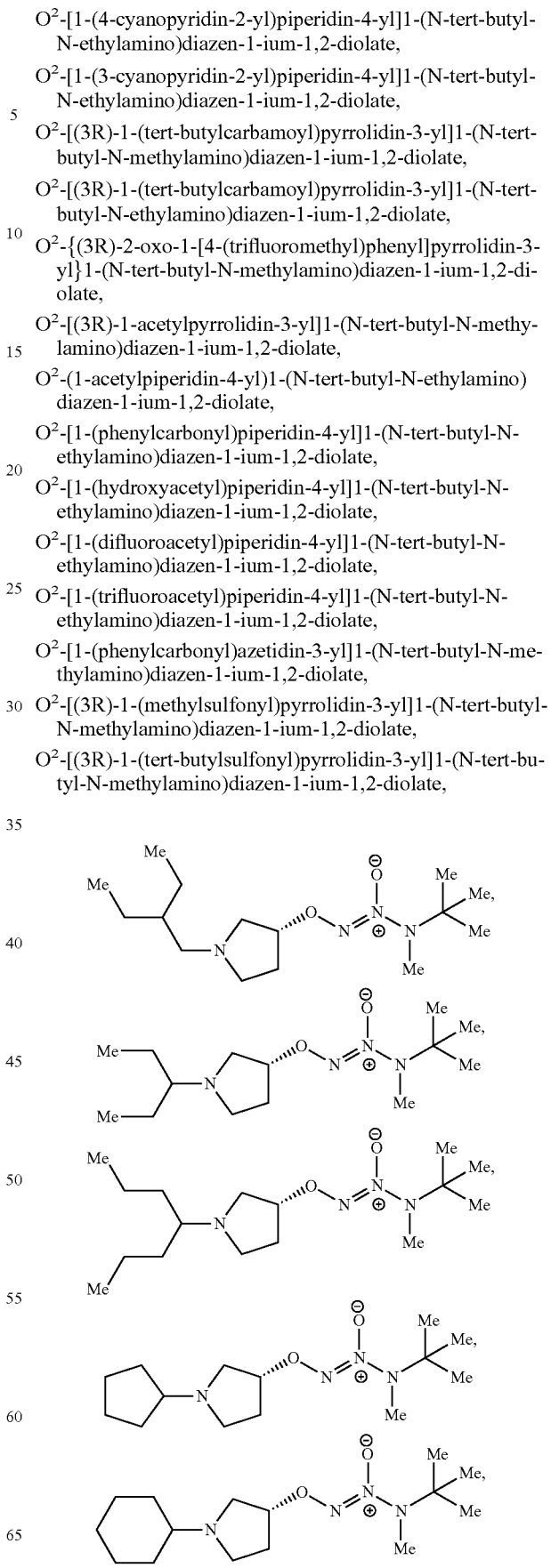

-continued

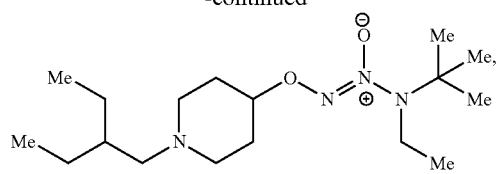
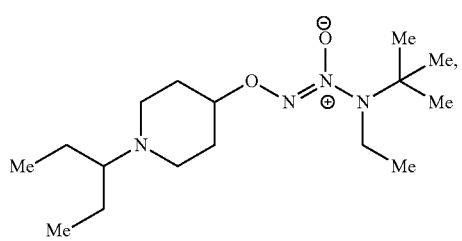
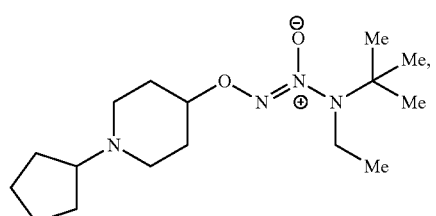
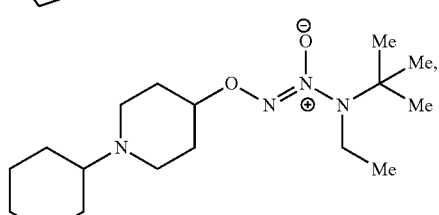
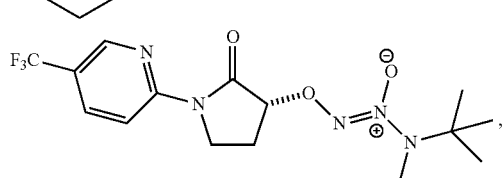
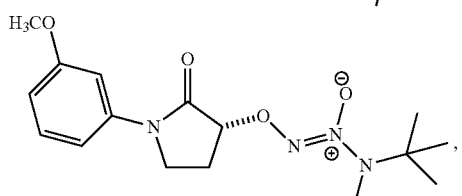
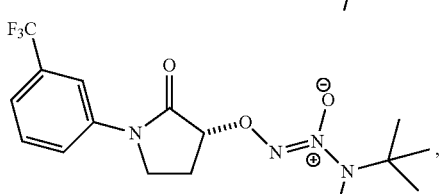
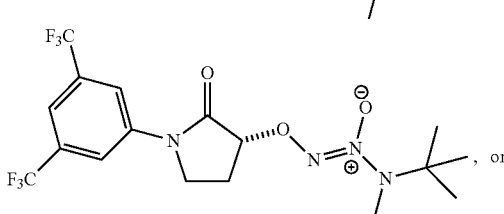

, or

-continued

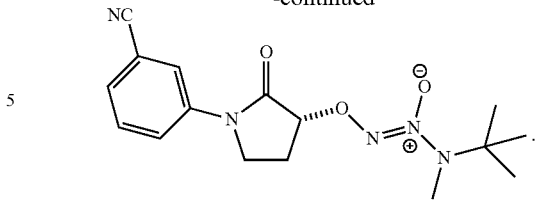

Compounds of the invention can be used to treat hypertension, treat angina, improve insulin sensitivity, and provide renal protection. The compounds can be used alone or in combination (e.g., separate but co-administered, or administered in a fixed dose) with other antihypertensives such as, for example, angiotensin II receptor blockers, diuretics, ACE inhibitors, β-blockers, and calcium channel blockers.

Pharmaceutically acceptable salts include non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, carbonate, cyclopentanepropionate, digluconate, dodecylsulfate, ethanesulfonate, fumarate, glucoheptanoate, gluconate, glycerophosphate, hemisulfate, heptanoate, hexanoate, hippurate, hydrochloride, hydrobromide, hydroiodide, 2-hydroxyethanesulfonate, lactate, lactobionate, laurylsulfate, malate, maleate, mesylate, methanesulfonate, 2-naphthalenesulfonate, nicotinate, nitrate, oleate, oxalate, pamoate, pectinate, persulfate, 3-phenylpropionate, picrate, pivalate, propionate, stearate, succinate, sulfate, tartrate, thiocyanate, tosylate, and undecanoate. Additional specific anionic salts include ascorbate, gluceptate, glutamate, glucoronate, besylate, caprylate, isetionate, gentisate, malonate, napasylate, edfisylate, pamoate, xinafoate, and napadisylate.

Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Additional specific cationic salts include tromethamine, benzathine, benethamine, diethylammonium, epolamine, hydrabamine.

When the compounds of the invention contain one chiral center, the term "stereoisomer" includes both enantiomers and mixtures of enantiomers, such as the specific 50:50 mixture referred to as the racemic mixture. The compounds of the present invention may have multiple chiral centers, providing for multiple stereoisomers. This invention includes all of the stereoisomers and mixtures thereof. Unless specifically mentioned otherwise, reference to one stereoisomer applies to any of the possible stereoisomers. Whenever the stereoisomeric composition is unspecified, all possible stereoisomers are included. Where used, the structure marking "*" indicates the location of a carbon atom that is a chiral center. When bonds to a chiral carbon are depicted as straight lines, it is understood that both (R) and (S) configurations of the chiral carbon, and hence both enantiomers and mixtures thereof, are represented.

Some of the compounds described herein may exist as tautomers. The individual tautomers as well as mixtures thereof are encompassed with the described compounds.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

As used herein except where noted, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g.,

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. $C_{1-4}$ alkyl includes n-, iso-, sec- and t-butyl, n- and isopropyl, ethyl and methyl. If no number is specified, 1-4 carbon atoms are intended for linear or branched alkyl groups.

As used herein except where noted, the term "alkylene" refers to any divalent linear or branched chain aliphatic hydrocarbon radical having a number of carbon atoms in the specified range. Thus, for example, "—$C_1$-$C_6$ alkylene-" refers to any of the $C_1$ to $C_6$ linear or branched alkylenes, and "—$C_1$-$C_4$ alkylene-" refers to any of the $C_1$ to $C_4$ linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Another sub-class of interest is an alkylene selected from the group consisting of —$CH_2$—, —$CH(CH_3)$—, and —$C(CH_3)_2$—. Expressions such as "$C_1$-$C_4$ alkylene-phenyl" and "$C_1$-$C_4$ alkyl substituted with phenyl" have the same meaning and are used interchangeably.

Alkyl groups and alkylene groups may be unsubstituted, or substituted with 1 to 3 substituents on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —OC(O)$C_1$-$C_6$ alkyl, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_0$-$C_6$ alkyl)C(O)NH—, $H_2$N—C(NH)—, —O($C_1$-$C_6$ alkyl)$CF_3$, HC(O)—, ($C_1$-$C_6$ alkyl)C(O)—, HOC(O)—, ($C_1$-$C_6$ alkyl)OC(O)—, HO($C_1$-$C_6$ alkyl)-, ($C_1$-$C_6$ alkyl)O($C_1$-$C_6$ alkyl)-, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, HOC(O)NH—, ($C_1$-$C_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

As used herein except where noted, the term "aryl", alone or in combination, relates to a phenyl, naphthyl or indanyl group, preferably a phenyl group. The abbreviation "Ph" represents phenyl.

As used herein except where noted, the term "carbocycle" (and variations thereof such as "carbocyclic" or "carbocyclyl") refers to a $C_3$ to $C_8$ monocyclic saturated or unsaturated ring. The carbocycle may be attached to the rest of the molecule at any carbon atom which results in a stable compound. Saturated carbocyclic rings are also referred to as cycloalkyl rings, e.g., cyclopropyl, cyclobutyl, etc.

As used herein except where noted, the term "heteroaryl" refers to an unsaturated ring having 5 or 6 atom ring members including 1, 2, 3 or 4 heteroatoms independently selected from N, O or S, e.g., 5-membered rings containing one nitrogen (pyrrole), one oxygen (pyran) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen atoms, five-membered aromatic rings containing one oxygen, one nitrogen or one sulfur atom, five-membered aromatic rings containing two heteroatoms independently selected from oxygen, nitrogen and sulfur, 6-membered rings containing one nitrogen (pyridine), or one oxygen (furan) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Examples of such ring systems are furanyl, thienyl, pyrrolyl, pyridinyl, pyrimidinyl, indolyl, imidazolyl, triazinyl, thiazolyl, isothiazolyl, pyridazinyl, pyrazolyl, oxazolyl, and isoxazolyl.

As used herein except where noted, the terms "heterocycle" and "heterocyclic" refer to a saturated ring having a specified number of atom members and a specified number of heteroatoms, in which the entire ring system (whether mono- or poly-cyclic) is saturated, e.g., a 4- to 8-membered saturated monocyclic ring or a stable 7- to 12-membered bicyclic ring system which consists of carbon atoms and one or more heteroatoms selected from N, O and S, a 5- or 6-membered heterocyclic ring having 1 or 2 heteroatoms which are N, O or S, etc. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Aryl groups and carbocycles may be unsubstituted, or substituted with 1, 2, or 3 substituents on any one or more available carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, HS(O)$_{0-2}$—, ($C_1$-$C_6$ alkyl)S(O)$_{0-2}$—, ($C_1$-$C_6$ alkyl)S(O)$_{0-2}$(C$_1$-C$_6$ alkyl)-, HS(O)$_{0-2}$(C$_1$-C$_6$ alkyl)-, (C$_1$-C$_6$ alkyl)S(O)$_{0-2}$—, (C$_1$-C$_6$ alkyl)C(O)NH—, HC(O)NH—, H$_2$N—C(NH)—, —O(C$_1$-C$_6$ alkyl)CF$_3$, (C$_1$-C$_6$ alkyl)C(O)—, HC(O)—, (C$_1$-C$_6$ alkyl)OC(O)—, HOC(O)—, (C$_1$-C$_6$ alkyl)O(C$_1$-C$_6$ alkyl)-, HO(C$_1$-C$_6$ alkyl)-, (C$_1$-C$_6$ alkyl)C(O)$_{1-2}$(C$_1$-C$_6$ alkyl)-, (C$_1$-C$_6$ alkyl)C(O)$_{1-2}$—, HC(O)$_{1-2}$(C$_1$-C$_6$ alkyl)-, (C$_1$-C$_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Heteroaryl groups and heterocycles may be unsubstituted, or substituted with 1, 2, or 3 substituents on any one or more available carbon atoms, with halogen, C$_1$-C$_{20}$ alkyl, CF$_3$, NH$_2$, —NH(C$_1$-C$_6$ alkyl), —N(C$_1$-C$_6$ alkyl)$_2$, NO$_2$, oxo, CN, N$_3$, —OH, —O(C$_1$-C$_6$ alkyl), C$_3$-C$_{10}$ cycloalkyl, C$_2$-C$_6$ alkenyl, C$_2$-C$_6$ alkynyl, (C$_1$-C$_6$ alkyl)S(O)$_{0-2}$—, HS(O)$_{0-2}$—, (C$_1$-C$_6$ alkyl)S(O)$_{0-2}$(C$_1$-C$_6$ alkyl)-, HS(O)$_{0-2}$(C$_1$-C$_6$ alkyl)-, (C$_1$-C$_6$ alkyl)S(O)$_{0-2}$—, (C$_1$-C$_6$ alkyl)C(O)NH—, HC(O)NH—, H$_2$N—C(NH)—, —O(C$_1$-C$_6$ alkyl)CF$_3$, HC(O)—, (C$_1$-C$_6$ alkyl)C(O)—, (C$_1$-C$_6$ alkyl)OC(O)—, HOC(O)—, (C$_1$-C$_6$ alkyl)O(C$_1$-C$_6$ alkyl)-, HO(C$_1$-C$_6$ alkyl)-, (C$_1$-C$_6$ alkyl)O—, (C$_1$-C$_6$ alkyl)C(O)$_{1-2}$(C$_1$-C$_6$ alkyl)-, HC(O)$_{1-2}$(C$_1$-C$_6$ alkyl)-, (C$_1$-C$_6$ alkyl)C(O)$_{1-2}$, (C$_1$-C$_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 or 2 substituents on any one or more available nitrogen atoms, with C$_1$-C$_{20}$ alkyl, oxo, C$_3$-C$_{10}$ cycloalkyl, C$_2$-C$_6$ alkenyl, C$_2$-C$_6$ alkynyl, aryl, —C(O)C$_{1-6}$ alkyl, —C(O)NHC$_1$-C$_6$ alkyl, —C(O)NH$_2$, —C$_1$-C$_6$ alkylC(O)NH$_2$, —C$_1$-C$_6$ alkylOC(O)NH$_2$, or independently or additionally substituted with 1 substituent on any one or more sulfur atoms, with C$_1$-C$_{20}$ alkyl, oxo, C$_3$-C$_{10}$ cycloalkyl, C$_2$-C$_6$ alkenyl, C$_2$-C$_6$ alkynyl, aryl, where such substitution results in formation of a stable compound. Substituted heterocyclic rings include cyclic ureas, such as imidazolidin-2-one and tetrahydropyrimidin-2(1H)-one, which rings contain three sequential atoms that are nitrogen, carbon and niotrogen, wherein the carbon atom is substituted with an oxo substituent.

The compounds of the invention are useful for treating hypertension, Pulmonary Arterial Hypertension, congestive heart failure, angina, conditions resulting from excessive water retention, cardiovascular diseases, diabetes, oxidative stress, endothelial dysfunction, cirrhosis, pre-eclampsia, osteoporosis, or nephropathy, comprising administering a compounds of the invention to a patient having such a condition, or being at risk to having such condition The invention also relates to the use of compounds of the invention for the preparation of a medicament for the treatment and/or prophylaxis of the above-mentioned diseases.

The above-mentioned compounds of the invention are also of use in combination with other pharmacologically active compounds comprising angiotensin II receptor antagonists (e.g., losartan, valsartan, candesartan, irbesartan, olmesartan) angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren ((2S,4S, 5S,7S)—N-(2-carbamoyl-2-methylpropyl)-5-amino-4-hydroxy-2,7-diisopropyl-8-[4-methoxy-3-(3-methoxypropoxy)phenyl]-octanamid hemifumarate) SPP600, SPP630 and SPP635), endothelin receptors antagonists, vasodilators, calcium channel blockers (e.g., amlodipine, nifedipine, verapamil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds including (i) PPAR.gamma. agonists, such as the glitazones (e.g. troglitazone, pioglitazone, englitazone, MCC-555, rosiglitazone, balaglitazone, and the like) and other PPAR ligands, including PPAR.alpha./.gamma. dual agonists, such as KRP-297, muraglitazar, naveglitazar, Galida, tesaglitazar, TAK-559, PPAR.alpha. agonists, such as fenofibric acid derivatives (gemfibrozil, clofibrate, fenofibrate and bezafibrate), and selective PPAR.gamma. modulators (SPPAR.gamma.M's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors, glipizide, DPP-IV inhibitors such as sitagliptin, vildagliptin, alogliptin, and saxagliptin, which inhibit dipeptidyl peptidase-IV enzyme and which are useful for treating diabetes, or with other drugs beneficial for the prevention or the treatment of the above-mentioned diseases including nitroprusside and diazoxide. Such combination can be achieved by combining two active ingredients in a single dosage formulation containing two independent active ingredients, e.g., an angiotensin II receptor antagonist and a nitrooxy cyclopentane derivative of the invention.

The dosage regimen utilizing the compound of the invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds of the invention, when used for the indicated effects, will range between about 0.0125 mg per kg of body weight per day (mg/kg/day) to about 7.5 mg/kg/day, preferably 0.0125 mg/kg/day to 3.75 mg/kg/day, and more preferably 0.3125 mg/kg/day to 1.875 mg/kg/day. For example, an 80 kg patient would receive between about 1 mg/day and 600 mg/day, preferably 1 mg/day to 300 mg/day, more preferably 25 mg/day to 150 mg/day, and more preferably 5 mg/day to 100 mg/day. A suitably prepared medicament for once a day administration would thus contain between 1 mg and 600 mg, preferably between 1 mg and 300 mg, and more preferably between 25 mg and 300 mg, e.g., 25 mg, 50 mg, 100 mg, 150, 200, 250 and 300 mg. Advantageously, the compound of the invention may be administered in divided doses of two, three, or four times daily. For administration twice a day, a suitably prepared medicament would contain between 0.5 mg and 300 mg, preferably between 0.5 mg and 150 mg, more preferably between 12.5 mg and 150 mg, e.g., 12.5 mg, 25 mg, 50 mg, 75 mg, 100 mg, 125 mg and 150 mg.

The compounds of the invention can be administered in such oral forms as tablets, capsules and granules. The compounds of the invention are typically administered as active ingredients in admixture with suitable pharmaceutical binders as described below. % w/w expresses the weight percent of the indicated composition constituent compared to the total composition. Suitable fillers used in these dosage forms include microcrystalline cellulose, silicified microcrystalline cellulose, dicalcium phosphate, lactose, mannitol, and starch, preferably microcrystalline cellulose, dicalcium phosphate, lactose or mixtures thereof. Suitable binders include hydroxypropyl cellulose, hydroxypropyl methyl cellulose, starch, gelatin, natural sugars such as glucose or beta-lactose, corn-sweeteners, natural and synthetic gums such as acacia, tragacanth or sodium alginate, carboxymethylcellulose, and polyvinyl pyrrolidone. Lubricants used in these dosage forms include sodium oleate, sodium stearate, magnesium stearate, sodium benzoate, sodium acetate, sodium chloride, sodium stearyl fumarate, stearic acid and the like, preferably magnesium stearate. Suitable coating compositions include aqueous dispersion or organic solution of insoluble polymers such as ethyl cellulose, cellulose aetate, cellulose acetate butyrate and acrylate copolymers commercially known as Eudragit®. Plasticizers include triethyl citrate, dibutyl sebacate, dibutyl phthalate, triacetin and castor oil. Antitacking agents include talc, kaolin, colloidal silica or mixtures thereof.

Methods of Synthesis

Several methods for preparing the compounds of this invention are described in the following Examples. Starting materials and intermediates are made from known procedures or as otherwise illustrated. Variables are as described above unless otherwise indicated. Examples on the preparation of the sodium diazeniumdiolates can be found from the literature (Chakrapani, H.; Showalter, B. M.; Citro, M. L.; Keefer, L. K.; Saavedra, J. E. *Org. Lett.* 2007, 9, 4551-4554 and WO Patent 2009/094242.

Scheme 1 delineates a method to prepare $O^2$-alkylated diazeniumdiolates of the general structure 1-4 in this invention. Aminoalcohols of the general structure 1-1 can be prepared from reduction of the corresponding ketone or hydroboration/oxidation of the corresponding olefin. The amino group of 1-1 can react with the proper electrophile, such as acid chloride, acid anhydride, chloroformate, sulfonyl chloride, isocyanate, cyanogen bromide, or alkyl halide in the presence of a base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone, to afford the functionalized aminoalcohol 1-2. Alternatively, when $R^7$ is an aromatic ring/heteroaromatic ring, it can be synthesized by coupling (hetero)aryl halides to the aminoalcohol 1-1 through the use of a catalytic amount of palladium complex, such as palladium(II) acetate, tris(dibenzylideneacetone)dipalladium(0), with an appropriate ligand, such as tri-tert-butylphosphine, 1,1'-bis(dicyclohexylphosphino) ferrocene, (2-biphenyl)di-tert-butylphosphine, 2-dicyclohexylphosphino-2'-(N,N-dimethylamino)biphenyl, or a preformed palladium-ligand complex, such as chloro(2-dicyclohexylphosphino-2',4',6'-triisopropyl-1,1'-biphenyl)[2-(2-aminoethyl)phenyl)]palladium(II). With electron-deficient aromatics or heteroaromatics, such as 3-cyanophenyl, the desired aminoalcohol 1-2 can be obtained by heating aminoalcohol 1-1 and the corresponding aromatic/heteroaromatic compound with an appropriate leaving group in a solvent of high boiling point, such as dimethyl sulfoxide, N,N-dimethylformamide, N-methylpyrrolidinone, or 1,3-dimethyl-3,4,5,6-tetrahydro-2(1H)-pyrimidinone in the presence of a base such as triethylamine, N,N-diisopropylethylamine, or potassium carbonate. The functionalized aminoalcohol 1-2 can be activated for displacement at an appropriate temperature such as room temperature with a suitable reagent such as methanesulfonic anhydride, benzenesulfonyl chloride, 4-(trifluoromethyl)phenylsulfonyl chloride in the presence or absence of a base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone. The resultant sulfonate 1-3 can be displaced by the appropriate sodium diazeniumdiolate salt at an appropriate temperature such as room temperature in an appropriate solvent such as dichloromethane, dichloroethane, chloroform, acetonitrile, tetrahydrofuran, dioxane, toluene, N,N-dimethylformamide, or N-methylpyrrolidinone. The stereochemistry at the sulfonate carbon is typically inverted as a result of the displacement.

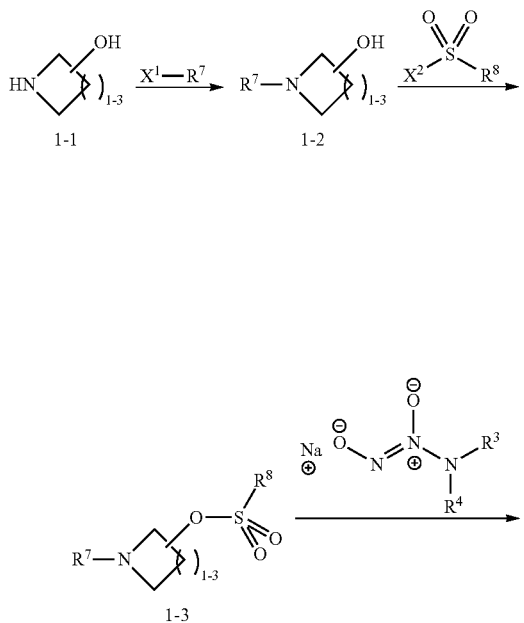

Scheme 1

-continued

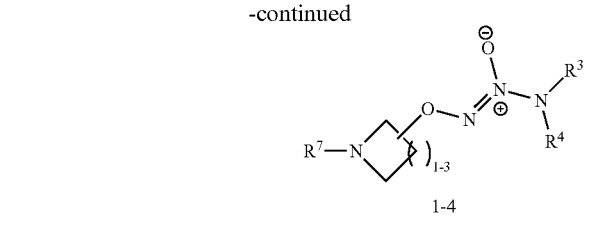

1-4

X¹—R⁷ = acid chloride, acid anhydride, chloroformate, sulfonyl chloride, isocyanate, cyanogen bromide, alkyl halide, (hetero)aromatic halide X² = Cl, OSO₂R⁸

R⁸ = straight or branched C$_{1-6}$alkyl, unsubstituted phenyl, or phenyl substituted with C$_{1-6}$alkyl Scheme 2 describes a method to prepare O²-alkylated diazeniumdiolates of general structure 2-5 in this invention. The N-tert-butoxycarbonyl protected aminoalcohol 2-1 can be activated for displacement at an appropriate temperature such as room temperature with a suitable reagent such as methanesulfonic anhydride, benzenesulfonyl chloride, 4-(trifluoromethyl)phenylsulfonyl chloride in the presence or absence of a base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone. The resultant sulfonate 2-2 can be displaced by the appropriate sodium diazeniumdiolate salt at an appropriate temperature such as room temperature in an appropriate solvent such as dichloromethane, dichloroethane, chloroform, acetonitrile, tetrahydrofuran, dioxane, toluene, N,N-dimethylformamide, or N-methylpyrrolidinone. The stereochemistry at the sulfonate carbon is typically inverted as a result of the displacement. The N-tert-butoxycarbonyl derivative 2-3 can be deprotected, typically with an appropriate acid such as trifluoroacetic acid, hydrochloric acid, phosphoric acid, or any other method described in Wuts, P. G. M.; Greene, T. W. *Greene's Protective Groups in Organic Synthesis*, 4$^{th}$ ed.; John Wiley & Sons, 2007. The resultant secondary cyclic amine 2-4 can be appropriately functionalized, using the various methods described for Scheme 1, to afford the general structure 2-5.

Scheme 2

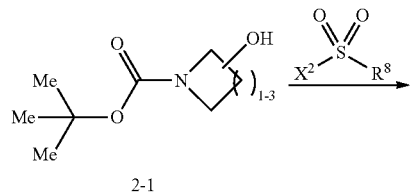

2-1

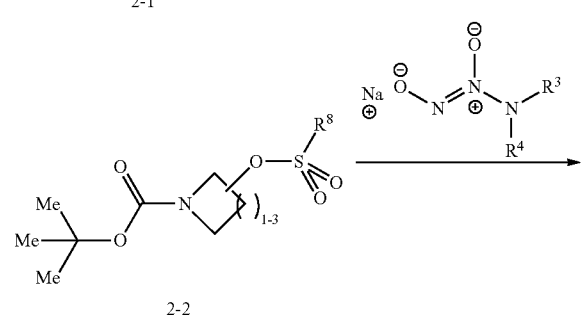

2-2

-continued

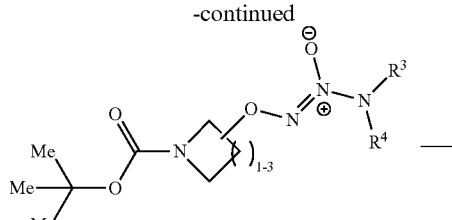

2-3

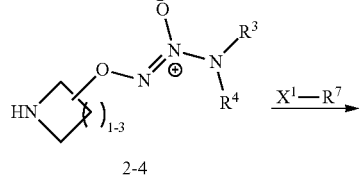

2-4

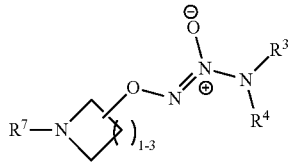

2-5

X¹—R⁷ = acid chloride, acid anhydride, chloroformate, sulfonyl chloride, isocyanate, cyanogen bromide, alkyl halide, (hetero)aromatic halide X² = Cl, OSO₂R⁸

R⁸ = straight or branched C$_{1-6}$alkyl, unsubstituted phenyl, or phenyl substituted with C$_{1-6}$alkyl Example 1

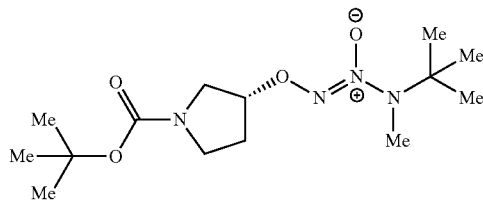 [SMILES: CN(/[N+]([O-])=N/O[C@@H]1CCN(C(=O)OC(C)(C)C)C1)C(C)(C)C]

O²-[(3R)-1-(tert-butoxycarbonyl)pyrrolidin-3-yl]1-(N-tert-butyl-N-methylamino)diazen-1-ium-1,2-diolate Step A: tert-butyl (3S)-3-({[4-(trifluoromethyl)phenyl]sulfonyl}oxy)pyrrolidine-1-carboxylate To a stirring dichloromethane (250 mL) solution of (3S)—N-(tert-butoxycarbonyl)pyrrolidinol (21.2 g, 113 mmol), 4-(dimethylamino)pyridine (1.40 g, 11.5 mmol), and triethylamine (40.0 mL, 287 mmol) at 0° C. was added 4-(trifluoromethyl)benzenesulfonyl chloride (30.5 g, 125 mmol). The reaction mixture was stirred for two hours at room temperature. The reaction was quenched with 1.0 M hydrochloric acid (100 mL) and extracted with diethyl ether (2×250 mL). The combined organic extracts were dried (magnesium sulfate), filtered and concentrated in vacuo to afford the crude product. Chromatography over silica gel, eluting with hexanes/ethyl acetate, afforded the title compound as a white solid. ¹H NMR (500 MHz, CDCl$_3$) δ 8.05 (d, J=8.1 Hz, 2H), 7.84 (d, J=7.9 Hz, 2H), 5.18-5.11 (m, 1H), 3.54-3.43 (m, 3H), 3.42 (td, J=10.4, 6.8 Hz, 1H), 2.25-1.97 (m, 2H), 1.43 (s, 9H).

Step B: O$^2$-[(3R)-1-(tert-butoxycarbonyl)pyrrolidin-3-yl]1-(N-tert-butyl-N-methylamino)diazen-1-ium-1,2-diolate To a stirring N,N-dimethylformamide (285 mL) solution of tert-butyl (3S)-3-({[4-(trifluoromethyl)phenyl]sulfonyl}oxy)pyrrolidine-1-carboxylate (45.1 g, 114 mmol) at 50° C. was added sodium 1-(N-tert-butyl-N-methylamino)diazen-1-ium-1,2-diolate (30.8 g, 182 mmol). The reaction mixture was stirred at 50° C. for 5 hours. The reaction mixture was diluted with water (500 mL) and extracted with ether (4×250 mL). The combined organic phase was washed with brine (2×250 mL), dried (magnesium sulfate), filtered and concentrated in vacuo to afford the crude product. Chromatography over silica gel, eluting with hexanes/ethyl acetate, afforded the title compound as a white solid. $^1$H NMR (500 MHz, CDCl$_3$) δ 4.94 (br s, 1H), 3.70 (t, J=13.0 Hz, 1H), 3.64-3.45 (m, 3H), 2.82 (s, 3H), 2.31-2.25 (m, 1H), 2.12 (br s, 1H), 1.46 (s, 9H), 1.24 (s, 9H); LC-MS: m/z 339.3 (M+Na).

Example 2

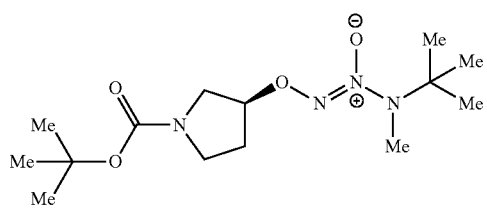 [SMILES: CN(/[N+]([O-])=N/O[C@H]1CCN(C(=O)OC(C)(C)C)C1)C(C)(C)C]

O$^2$-[(3S)-(tert-butoxycarbonyl)pyrrolidin-3-yl]1-(N-tert-butyl-N-methylamino)diazen-1-ium-1,2-diolate The title compound was made by following the procedures described in EXAMPLE 1, substituting (3R)—N-(tert-butoxycarbonyl)pyrrolidinol for (3S)—N-(tert-butoxycarbonyl)pyrrolidinol in step A.

Example 3

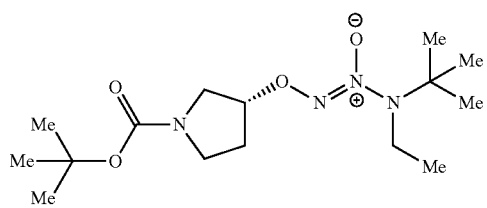 [SMILES: CCN(/[N+]([O-])=N/O[C@@H]1CCN(C(=O)OC(C)(C)C)C1)C(C)(C)C]

O$^2$-[(3R)-1-(tert-butoxycarbonyl)pyrrolidi-3-yl]-(N-tert-butyl-N-ethylamino)diazen-1-ium-2-diolate The title compound was made by following the procedures described in EXAMPLE 1, substituting sodium 1-(N-tert-butyl-N-ethylamino)diazen-1-ium-1,2-diolate for sodium 1-(N-tert-butyl-N-methylamino)diazen-1-ium-1,2-diolate in step B. $^1$H NMR (500 MHz, CDCl$_3$) δ 4.97 (br s, 1H), 3.70 (d, J=13.0 Hz, 1H), 3.66-3.46 (m, 3H), 3.12 (q, J=7.1 Hz, 2H), 2.28 (dd, J=13.8, 6.2 Hz, 1H), 2.15-2.08 (m, 1H), 1.45 (s, 9H), 1.25 (s, 9H), 1.05 (t, J=7.0 Hz, 3H); LC-MS: m/z 353.0 (M+Na).

Example 4

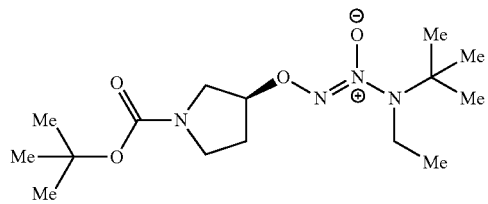 [SMILES: CCN(/[N+]([O-])=N/O[C@H]1CCN(C(=O)OC(C)(C)C)C1)C(C)(C)C]

O$^2$-[(3R)-1-(tert-butoxycarbonyl)pyrrolidin-3-yl]-(N-tert-butyl-N-ethylamino)diazen-1-ium-1,2-diolate The title compound was made by following the procedures described in EXAMPLE 3, substituting (3R)—N-(tert-butoxycarbonyl)pyrrolidinol for (3S)—N-(tert-butoxycarbonyl)pyrrolidinol.

Example 5

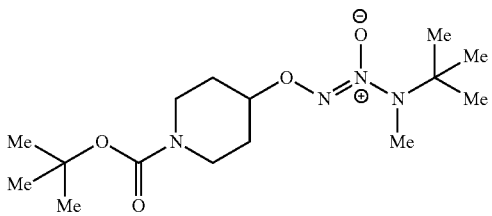 [SMILES: CN(/[N+]([O-])=N/OC1CCN(C(=O)OC(C)(C)C)CC1)C(C)(C)C]

O$^2$-[1-(tert-butoxycarbonyl)piperidin-4-yl]1-(N-tert-butyl-N-methylamino)diazen-1-ium-1,2-diolate The title compound was made by following the procedures described in EXAMPLE 1, substituting N-(tert-butoxycarbonyl)-4-hydroxypiperidine for (3S)—N-(tert-butoxycarbonyl)pyrrolidinol in step A. $^1$H NMR (500 MHz, CDCl$_3$) δ 4.43 (tt, J=8.8, 3.9 Hz, 1H), 3.90-3.76 (m, 2H), 3.11 (ddd, J=13.6, 9.4, 3.4 Hz, 2H), 2.80 (s, 3H), 2.02-1.94 (m, 2H), 1.81-1.72 (m, 2H), 1.45 (s, 9H), 1.23 (s, 9H); LC-MS: m/z 353.2 (M+Na).

Example 6

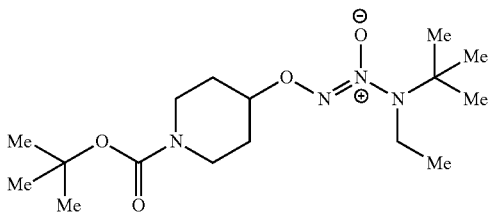 [SMILES: CCN(/[N+]([O-])=N/OC1CCN(C(=O)OC(C)(C)C)CC1)C(C)(C)C]

O²-[1-(tert-butoxycarbonyl)piperidin-4-yl]1-(N-tert-butyl-N-ethylamino)diazen-1-ium-1,2-diolate The title compound was made by following the procedures described in EXAMPLE 5, substituting sodium 1-(N-tert-butyl-N-ethylamino)diazen-1-ium-1,2-diolate for sodium 1-(N-tert-butyl-N-methylamino)diazen-1-ium-1,2-diolate. ¹H NMR (500 MHz, CDCl₃) δ 4.50-4.43 (m, 1H), 3.89-3.77 (m, 2H), 3.16-3.08 (m, 4H), 1.99 (d, J=12.4 Hz, 2H), 1.81-1.72 (m, 2H), 1.45 (s, 9H), 1.23 (s, 9H), 1.03 (t, J=7.0 Hz, 3H); LC-MS: m/z 367.1 (M+Na).

Example 7

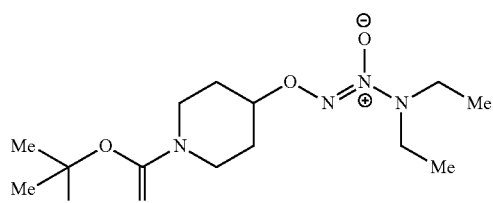

O²-[1-(tert-butoxycarbonyl)piperidin-4-yl]1-(N,N-diethylamino)diazen-1-ium-1,2-diolate The title compound was made by following the procedures described in EXAMPLE 5, substituting sodium 1-(N,N-diethylamino)diazen-1-ium-1,2-diolate for sodium 1-(N-tert-butyl-N-methylamino)diazen-1-ium-1,2-diolate. ¹H NMR (500 MHz, CDCl₃) δ 4.45 (tt, J=8.7, 3.9 Hz, 1H), 3.82 (m, 2H), 3.11 (ddd, J=13.7, 9.3, 3.5 Hz, 2H), 3.06 (q, J=7.1 Hz, 4H), 2.01-1.94 (m, 2H), 1.81-1.72 (m, 2H), 1.44 (s, 9H), 1.07 (t, J=7.1 Hz, 6H); LC-MS: m/z 339.3 (M+Na).

Example 8

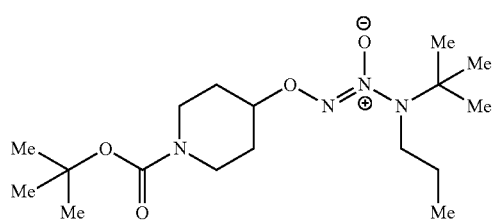 [SMILES: CCCN(/[N+]([O-])=N/OC1CCN(C(=O)OC(C)(C)C)CC1)C(C)(C)C]

O²-[1-(tert-butoxycarbonyl)piperidin-4-yl]1-(N-tert-butyl-N-propylamino)diazen-1-ium-1,2-diolate Step A: sodium 1-(N-tert-butyl-N-propylamino)diazen-1-ium-1,2-diolate To a methanol (2.5 mL) solution of N-tert-butyl-N-propylamine (1.88 g, 16.3 mmol) was added a 25 weight % methanolic solution of sodium methoxide (3.73 mL, 16.3 mmol). The solution was stirred for 24 hours at 25° C. under nitric oxide (350 psi). The methanol was removed in vacuo, and diethyl ether was added to precipitate a white solid. The solid was filtered, washed with diethyl ether, and dried under vacuum to afford the title compound. ¹H NMR (500 MHz, D₂O) δ 2.95 (t, J=7.2 Hz, 2H), 1.25 (sextet, J=7.4 Hz, 2H), 1.15 (s, 9H), 0.87 (t, J=7.4 Hz, 3H).

Step B: O²-[1-(tert-butoxycarbonyl)piperidin-4-yl]1-(N-tert-butyl-N-propylamino)diazen-1-ium-1,2-diolate The title compound was made by following the procedures described in EXAMPLE 5, substituting sodium 1-(N-tert-butyl-N-propylamino)diazen-1-ium-1,2-diolate for sodium 1-(N-tert-butyl-N-methylamino)diazen-1-ium-1,2-diolate. ¹H NMR (500 MHz, CDCl₃) δ 4.48 (tt, J=8.7, 3.9 Hz, 1H), 3.92-3.78 (m, 2H), 3.15 (ddd, J=13.6, 9.3, 3.4 Hz, 2H), 3.02 (t, J=7.3 Hz, 2H), 2.06-1.95 (m, 2H), 1.83-1.74 (m, 2H), 1.48 (s, 9H), 1.40 (sextet, J=7.4 Hz, 2H), 1.25 (s, 9H), 0.96 (t, J=7.4 Hz, 3H); LC-MS: m/z 381.2 (M+Na).

Example 9

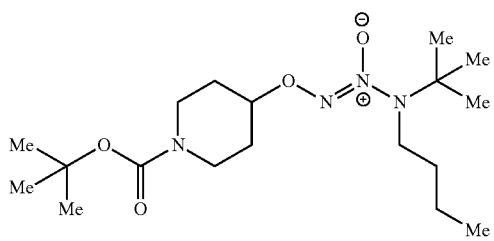 [SMILES: CCCCN(/[N+]([O-])=N/OC1CCN(C(=O)OC(C)(C)C)CC1)C(C)(C)C]

O²-[1-(tert-butoxycarbonyl)piperidin-4-yl]1-(N-butyl-N-tert-butylamino)diazen-1-ium-1,2-diolate The title compound was made by following the procedures described in EXAMPLE 8, substituting N-butyl-N-tert-butylamine for N-tert-butyl-N-propylamine in step A. ¹H NMR (500 MHz, CDCl₃) δ 4.45 (tt, J=8.7, 3.9 Hz, 1H), 3.88-3.76 (m, 2H), 3.12 (ddd, J=13.6, 9.3, 3.3 Hz, 2H), 3.02 (t, J=6.7 Hz, 2H), 2.02-1.93 (m, 2H), 1.81-1.71 (m, 2H), 1.44 (s, 9H), 1.38-1.30 (m, 4H), 1.21 (s, 9H), 0.89 (t, J=6.9 Hz, 3H); LC-MS: m/z 395.3 (M+Na).

Example 10

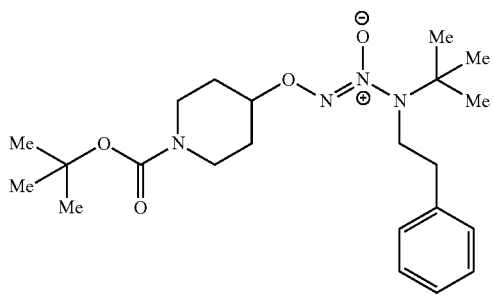 [SMILES: CC(C)(C)OC(=O)N1CCC(O/N=[N+](\[O-])N(CCc2ccccc2)C(C)(C)C)CC1]

O²-[1-(tert-butoxycarbonyl)piperidin-4-yl]1-(N-tert-butyl-N-phenylethylamino)diazen-1-ium-1,2-diolate The title compound was made by following the procedures described in EXAMPLE 8, substituting N-tert-butyl-N-phenylethylamine for N-tert-butyl-N-propylamine in step A. ¹H NMR (500 MHz, CDCl₃) δ 7.24-7.17 (m, 2H), 7.16-7.11 (m, 3H), 4.41 (tt, J=8.7, 3.9 Hz, 1H), 3.85-3.70 (m, 2H), 3.20 (t, J=7.8 Hz, 2H), 3.06 (ddd, J=13.6, 9.2, 3.4 Hz, 2H), 2.58 (t, J=7.8 Hz, 2H), 1.98-1.88 (m, 2H), 1.77-1.66 (m, 2H), 1.38 (s, 9H), 1.14 (s, 9H); LC-MS: m/z 443.3 (M+Na).

Example 11

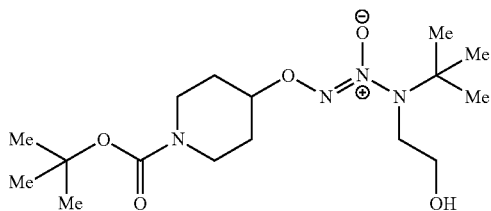 [SMILES: CC(C)(C)OC(=O)N1CCC(O/N=[N+](\[O-])N(CCO)C(C)(C)C)CC1]

O²-[1-(tert-butoxycarbonyl)piperidin-4-yl]1-[N-tert-butyl-N-(2'-hydroxyethyl)amino]diazen-1-ium-1,2-diolate The title compound was made by following the procedures described in EXAMPLE 8, substituting 2-(tert-butylamino)ethanol for N-tert-butyl-N-propylamine in step A. ¹H NMR (500 MHz, CDCl₃) δ 4.46 (tt, J=8.7, 3.8 Hz, 1H), 3.91-3.76 (br m, 3H), 3.54 (q, J=5.1 Hz, 2H), 3.24 (t, J=4.9 Hz, 2H), 3.13 (ddd, J=13.6, 9.3, 3.4 Hz, 2H), 2.02-1.94 (m, 2H), 1.82-1.70 (m, 2H), 1.45 (s, 9H), 1.24 (s, 9H); LC-MS: m/z 383.3 (M+Na).

Example 12

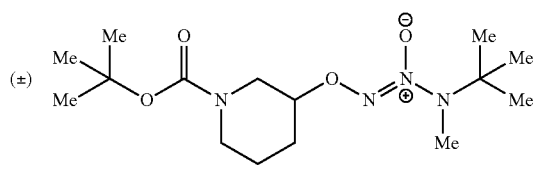 [SMILES: CN(/[N+]([O-])=N/OC1CCCN(C(=O)OC(C)(C)C)C1)C(C)(C)C]

(±)-[1-(tert-butoxycarbonyl)piperidin-3-yl]1-(N-tert-butyl-N-methylamino)diazen-1-ium-1,2-diolate The title compound was made by following the procedures described in EXAMPLE 1, substituting (±)-N-(tert-butoxycarbonyl)-3-hydroxypiperidine for (3S)—N-(tert-butoxycarbonyl)pyrrolidinol in step A. ¹H NMR (500 MHz, CDCl₃) δ 4.28 (m, 1H), 4.03 (dd, J=4.0, 13.1 Hz, 1H), 3.71 (m, 1H), 3.17 (m, 1H), 2.99 (m, 1H), 2.81 (s, 3H), 2.11-2.08 (m, 1H), 1.84-1.67 (m, 2H), 1.57-1.41 (m, 10H), 1.23 (s, 9H): LC-MS: m/z 352.9 (M+Na)

Example 13

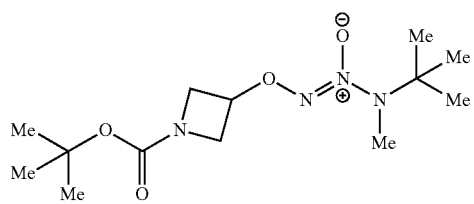 [SMILES: CN(/[N+]([O-])=N/OC1CN(C(=O)OC(C)(C)C)C1)C(C)(C)C]

O²-[1-(tert-butoxycarbonyl)azetidin-3-yl]1-(N-tert-butyl-N-methylamino)diazen-1-ium-1,2-diolate The title compound was made by following the procedures described in EXAMPLE 1, substituting N-(tert-butoxycarbonyl)-3-hydroxyazetidine for (3S)—N-(tert-butoxycarbonyl)pyrrolidinol in step A. ¹H NMR (500 MHz, CDCl₃) δ 4.96 (m, 1H), 4.12 (m, 2H), 3.98 (m, 2H), 2.72 (s, 3H), 1.35 (m, 9H), 1.15 (m, 9H).

Example 14

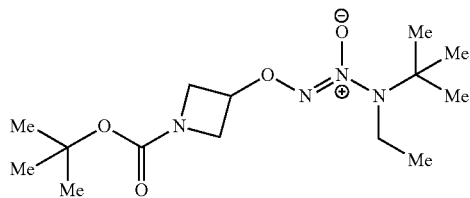 [SMILES: CCN(/[N+]([O-])=N/OC1CN(C(=O)OC(C)(C)C)C1)C(C)(C)C]

O²-[1-(tert-butoxycarbonyl)azetidin-3-yl]1-(N-tert-butyl-N-ethylamino)diazen-1-ium-1,2-diolate The title compound was made by following the procedures described in EXAMPLE 13, substituting sodium 1-N-(tert-butyl-N-ethylamino)diazen-1-ium-1,2-diolate for sodium 1-(N-tert-butyl-N-methylamino)diazen-1-ium-1,2-diolate. ¹H NMR (500 MHz, CDCl₃) δ 5.01 (m, 1H), 4.20 (m, 2H), 4.03 (m, 2H), 3.10 (m, 2H), 1.43 (m, 9H), 1.23 (m, 9H), 1.02 (m, 3H).

Example 15

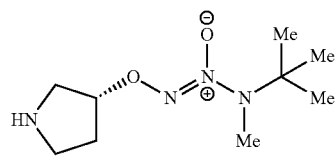 [SMILES: CN(/[N+]([O-])=N/O[C@@H]1CCNC1)C(C)(C)C]

O²-[(3R)-pyrrolidin-3-yl]1-(N-tert-butyl-N-methylamino)diazen-1-ium-1,2-diolate

To a stirring acetonitrile (60 mL) solution of O²-[(3R)-1-(tert-butoxycarbonyl)pyrrolidin-3-yl]1-(N-tert-butyl-N-methylamino)diazen-1-ium-1,2-diolate (EXAMPLE 1, 3.50 g, 11.1 mmol) was added 5 M hydrochloric acid (11.0 mL, 55.0 mmol). The reaction mixture was stirred at room temperature for 16 hours. The reaction mixture was concentrated in vacuo, redissolved in tert-butanol and lyophilized to afford the hydrochloride salt of the title compound. ¹H NMR (500 MHz, CDCl₃) δ 10.12 (br s, 1H), 9.90 (br s, 1H), 5.10 (br s, 1H), 3.85-3.52 (m, 3H), 3.53-3.40 (m, 1H), 2.82 (s, 3H), 2.49-2.29 (m, 2H), 1.24 (s, 9H); LC-MS: m/z 217.3 (M+H).

Example 16

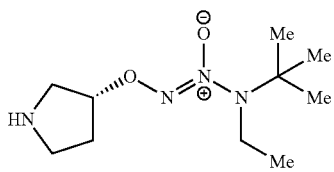 [SMILES: CCN(/[N+]([O-])=N/O[C@@H]1CCNC1)C(C)(C)C]

O²-[(3R)-pyrrolidin-3-yl]1-(N-tert-butyl-N-ethylamino)diazen-1-ium-1,2-diolate

The title compound was made by following the procedures described in EXAMPLE 15, substituting O²-[(3R)-1-(tert-butoxycarbonyl)pyrrolidin-3-yl]1-(N-tert-butyl-N-ethylamino)diazen-1-ium-1,2-diolate (EXAMPLE 3) for O²-[(3R)-1-(tert-butoxycarbonyl)pyrrolidin-3-yl]1-(N-tert-butyl-N-methylamino)diazen-1-ium-1,2-diolate (EXAMPLE 1). The free base form was generated by stirring a dichloromethane solution of the salt of the title compound with potassium carbonate and removing the solvent in vacuo. $^1$H NMR (500 MHz, CDCl$_3$) δ 5.00 (t, J=5.5 Hz, 1H), 3.27 (d, J=13.3 Hz, 1H), 3.20 (dt, J=11.6, 7.2 Hz, 1H), 3.13 (q, J=7.0 Hz, 2H), 2.99 (dd, J=13.3, 4.8 Hz, 1H), 2.88 (ddd, J=11.5, 8.5, 5.9 Hz, 1H), 2.16-2.01 (m, 2H), 1.26 (s, 9H), 1.06 (t, J=7.0 Hz, 3H); LC-MS: m/z 231.0 (M+H).

Example 17

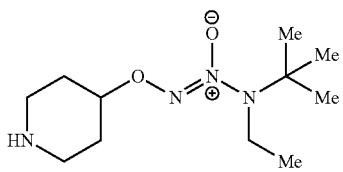 [SMILES: CCN(/[N+]([O-])=N/OC1CCNCC1)C(C)(C)C]

O²-(piperidin-4-yl)1-N-tert-butyl-N-ethylamino)diazen-1-ium-1,2-diolate

The hydrochloride salt of the title compound was made by following the procedures described in EXAMPLE 15, substituting O²-[1-(tert-butoxycarbonyl)piperidin-4-yl]1-(N-tert-butyl-N-ethylamino)diazen-1-ium-1,2-diolate (EXAMPLE 6) for O²-[(3R)-1-(tert-butoxycarbonyl)pyrrolidin-3-yl]1-(N-tert-butyl-N-methylamino)diazen-1-ium-1,2-diolate (EXAMPLE 1). $^1$H NMR (500 MHz, CDCl$_3$) δ 4.70-4.63 (m, 1H), 3.45-3.32 (m, 2H), 3.36-3.26 (m, 2H), 3.13 (q, J=7.0 Hz, 2H), 2.31-2.14 (m, 4H), 1.23 (s, 9H), 1.02 (t, J=7.0 Hz, 3H); LC-MS: m/z 245.3 (M+H).

Example 18

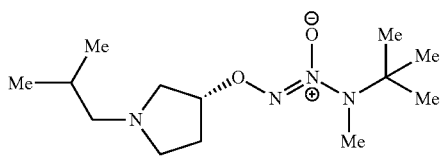 [SMILES: CC(C)CN1CC[C@@H](O/N=[N+](\[O-])N(C)C(C)(C)C)C1]

O²-[(3R)-1-(2-methylpropyl)pyrrolidin-3-yl]1-(N-tert-butyl-N-methylamino)diazen-1-ium-1,2-diolate To a mixture of the hydrochloride salt of O²-[(3R)-pyrrolidin-3-yl]1-(N-tert-butyl-N-methylamino)diazen-1-ium-1,2-diolate (15 mg, 0.045 mmol) and isobutyraldehyde was charged N,N-dimethylformamide (2 mL) solution with 15% acetic acid (150 μL), followed by polymer-bound cyanoborohydride (0.17 g, 0.40 mmol). The reaction mixture was stirred at 55° C. for 16 hours, filtered, rinsed with N,N-dimethylformamide (2×0.5 mL) and purified by mass-directed reversed-phase HPLC. LC-MS: m/z 273.2 (M+H).

The following examples were prepared using the same procedures described for EXAMPLE 18, substituting the appropriate aldehyde or ketone for isobutyraldehyde:

| | Structure | Aldehyde/ketone | LC-MS (m/z) |
|---|---|---|---|
| EXAMPLE 19 | 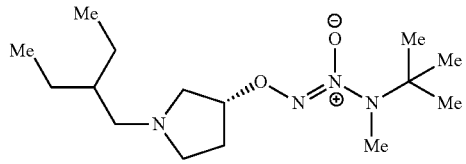 [SMILES: CCC(CC)CN1CC[C@@H](O/N=[N+](\[O-])N(C)C(C)(C)C)C1] | 2-ethylbutyraldehyde | 301.6 |
| EXAMPLE 20 | 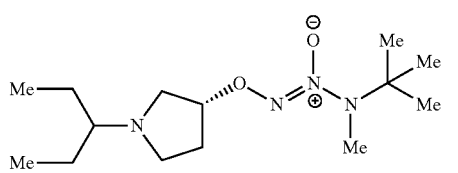 [SMILES: CCC(CC)N1CC[C@@H](O/N=[N+](\[O-])N(C)C(C)(C)C)C1] | 3-pentanone | 287.5 |

| Structure | Aldehyde/ketone | LC-MS (m/z) |
|---|---|---|
| EXAMPLE 21 | 4-heptanone | 315.2 |
| EXAMPLE 22 | cyclopentanone | 285.2 |
| EXAMPLE 23 | cyclohexanone | 299.2 |

The following examples were prepared using the same procedures described for EXAMPLE 18, substituting $O^2$-(piperidin-4-yl)1-(N-tert-butyl-N-ethylamino)diazen-1-ium-1,2-diolate (EXAMPLE 17) for $O^2$-[(3R)-pyrrolidin-3-yl]1-(N-tert-butyl-N-methylamino)diazen-1-ium-1,2-diolate (EXAMPLE 15), and the appropriate aldehyde or ketone for isobutyraldehyde:

| Structure | Aldehyde/ketone | LC-MS (m/z) |
|---|---|---|
| EXAMPLE 24 | 2-ethylbutyraldehyde | 329.2 |
| EXAMPLE 25 | 3-pentanone | 315.2 |
| EXAMPLE 26 | cyclopentanone | 313.2 |

| Structure | Aldehyde/ketone | LC-MS (m/z) |
|---|---|---|
| EXAMPLE 27 ![structure] | cyclohexanone | 327.2 |

Example 28

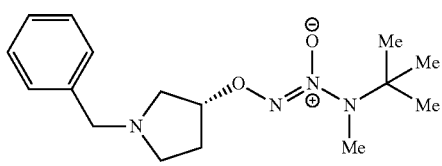 [SMILES: CN(/[N+]([O-])=N/O[C@@H]1CCN(Cc2ccccc2)C1)C(C)(C)C]

O²-[(3R)-1-benzylpyrrolidin-3-yl]1-(N-tert-butyl-N-methylamino)diazen-1-ium-1,2-diolate To a N,N-dimethylformamide (10 mL) solution of the hydrochloride salt of O²-[(3R)-pyrrolidin-3-yl]1-(N-tert-butyl-N-methylamino)diazen-1-ium-1,2-diolate (EXAMPLE 15, 420 mg, 1.27 mmol) and triethylamine (0.151 mL, 1.08 mmol) was added benzaldehyde (191 mg, 1.80 mmol). After stirring 15 minutes, sodium triacetoxyborohydride (636 mg, 3.00 mmol) was added in three portions over 30 minutes. The reaction mixture was stirred for 4 hours and quenched with saturated sodium carbonate (2 mL) and stirred for 30 minutes. It was diluted with diethyl ether (40 mL), and the combined organic extracts were washed with brine, dried (sodium sulfate), filtered and concentrated in vacuo to afford a crude product. Chromatography over silica gel, eluting with hexanes/acetone, afforded the title compound as a yellow liquid. ¹H NMR (500 MHz, CDCl₃) δ 7.35-7.26 (m, 5H), 4.99-4.95 (m, 1H), 3.68 (d, J=12.8 Hz, 1H), 3.66 (d, J=12.8 Hz, 1H), 2.98-2.94 (m, 1H), 2.82 (s, 3H), 2.85-2.77 (m, 2H), 2.62-2.58 (m, 1H), 2.32-2.23 (m, 1H), 2.12-2.07 (m, 1H), 1.25 (s, 9H); LC-MS: m/z 307 (M+H).

Example 29

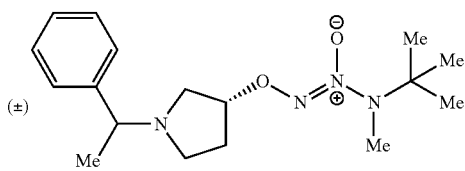 [SMILES: CC(c1ccccc1)N1CC[C@@H](O/N=[N+](\[O-])N(C)C(C)(C)C)C1]

O²-[(3R)-1-(1-phenylethyl)pyrrolidin-3-yl]1-(N-tert-butyl-N-methylamino)diazen-1-ium-1,2-diolate The title compound as a diastereomeric mixture was made by following the procedures described in EXAMPLE 28, substituting acetophenone for benzaldehyde. LC-MS: m/z 321 (M+H).

Example 30

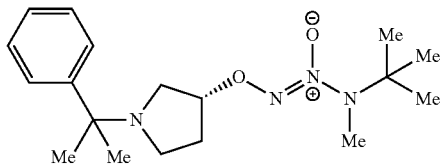 [SMILES: CN(/[N+]([O-])=N/O[C@@H]1CCN(C(C)(C)c2ccccc2)C1)C(C)(C)C]

O²-[3R)-1-(2-phenylpropan-2-yl)pyrrolidin-3-yl]1-(N-tert-butyl-N-methylamino)diazen-1-ium-1,2-diolate Step A: O²-[(3R)-1-(2-cyanopropan-2-yl)pyrrolidin-3-yl]1-(N-tert-butyl-N-methylamino)diazen-1-ium-1,2-diolate To an aqueous (2 mL) solution of the hydrochloride salt of O²-[(3R)-pyrrolidin-3-yl]1-(N-tert-butyl-N-methylamino)diazen-1-ium-1,2-diolate (EXAMPLE 15, 1.01 g, 4.00 mmol) was added 2 N hydrochloric acid until the pH is about 1-2, followed by potassium cyanide (0.260 g, 4.00 mmol). This solution was added dropwise to a diethyl ether (2 mL) solution of acetone (0.308 mL, 4.20 mmol) at 0° C. The reaction vial was sealed, and the reaction mixture was stirred at room temperature for 36 hours. It was diluted with diethyl ether (10 mL), washed with brine (2×2 mL), dried (magnesium sulfate), filtered and concentrated in vacuo to afford the title compound as a pale brown oil. ¹H NMR (500 MHz, CDCl₃) δ 4.93-4.90 (m, 1H), 3.08-3.06 (m, 1H), 3.06-2.98 (m, 1H), 2.90-2.86 (m, 1H), 2.78 (s, 3H), 2.61-2.56 (m, 1H), 2.32-2.25 (m, 1H), 2.13-2.07 (m, 1H), 1.46 (s, 3H), 1.45 (s, 3H), 1.20 (s, 9H).

Step B: O²-[(3R)-(2-phenylpropan-2-yl)pyrrolidin-3-yl]1-(N-tert-butyl-N-methylamino)diazen-1-ium-1,2-diolate To a tetrahydrofuran (2 ml) solution of O²-[(3R)-1-(2-cyanopropan-2-yl)pyrrolidin-3-yl]1-(N-tert-butyl-N-methylamino)diazen-1-ium-1,2-diolate (500 mg, 1.76 mmol) at 0° C. was added phenylmagnesium bromide (2.65 mL, 2.65 mmol). The reaction mixture was stirred for 30 minutes, and then allowed to warm to room temperature overnight. It was quenched with saturated ammonium chloride (3 mL) and extracted with diethyl ether (2×15 mL). The combined organic extracts were washed with brine, dried (magnesium sulfate), and concentrated in vacuo to afford the crude product. Chromatography over silica gel, eluting with hexanes/acetone, afforded the title compound as a yellow liquid. $^1$H NMR (500 MHz, CDCl$_3$) δ 7.53-7.20 (m, 5H), 4.91-4.88 (m, 1H), 2.95-2.92 (m, 1H), 2.82 (s, 3H), 2.80-2.75 (m, 2H), 2.60-2.55 (m, 1H), 2.24-2.15 (m, 1H), 2.07-2.02 (m, 1H), 1.42 (s, 6H), 1.24 (s, 9H); LC-MS: m/z 335 (M+H).

Example 31

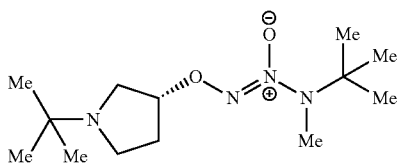 [SMILES: CN(/[N+]([O-])=N/O[C@@H]1CCN(C(C)(C)C)C1)C(C)(C)C]

O$^2$-[(3R)-1-tert-butylpyrrolidin-3-yl]1-(N-tert-butyl-N-methylamino)diazen-1-ium-1,2-diolate The title compound was made by following the procedures described in EXAMPLE 30, substituting methylmagnesium bromide for phenylmagnesium bromide in step B. $^1$H NMR (500 MHz, CDCl$_3$) δ 4.99-4.92 (m, 1H), 3.16-3.10 (m, 1H), 2.82 (s, 3H), 3.04-2.65 (m, 3H), 2.27-2.16 (m, 1H), 2.10-2.04 (m, 1H), 1.27 (s, 9H), 1.10 (s, 9H).

Example 32

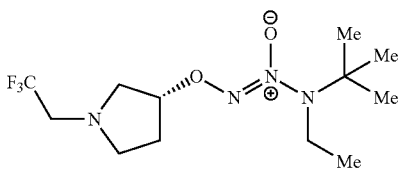 [SMILES: CCN(/[N+]([O-])=N/O[C@@H]1CCN(CC(F)(F)F)C1)C(C)(C)C]

O$^2$-[(3R)-1-(2,2,2-trifluoroethyl)pyrrolidin-3-yl]-1-(N-tert-butyl-N-ethylamino)diazen-1-ium-1,2-diolate To a stirring acetonitrile (8.6 mL) mixture of O$^2$-[(3R)-pyrrolidin-3-yl]1-(N-tert-butyl-N-ethylamino)diazen-1-ium-1,2-diolate (EXAMPLE 16,446 mg, 1.94 mmol) and potassium carbonate (589 mg, 4.26 mmol) was added 2,2,2-trifluoromethyl trifluoromethanesulfonate (0.335 mL, 2.32 mmol). The mixture was heated to 40° C. for 2 hours. Water (10 mL) was added, and the product was extracted with methyl tert-butyl ether (3×20 mL), dried (magnesium sulfate), filtered and concentrated in vacuo to give a crude oil. Chromatography over silica gel, eluting with hexanes/ethyl acetate, afforded the title compound as a viscous oil. $^1$H NMR (500 MHz, CDCl$_3$) δ 5.02-4.97 (m, 1H), 3.28 (dd, J=11.2, 6.1 Hz, 1H), 3.19-3.09 (m, 4H), 2.94-2.87 (m, 3H), 2.31-2.21 (m, 1H), 2.16-2.09 (m, 1H), 1.26 (s, 9H), 1.06 (t, J=7.0 Hz, 3H); LC-MS: m/z 313.0 (M+H).

Example 33

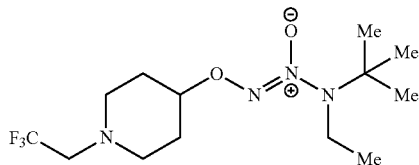 [SMILES: CCN(/[N+]([O-])=N/OC1CCN(CC(F)(F)F)CC1)C(C)(C)C]

O$^2$-[1-(2,2,2-trifluoroethyl)piperidin-4-yl]1-(N-tert-butyl-N-ethylamino)diazen-1-ium-1,2-diolate The title compound was made by following the procedures described in EXAMPLE 32, substituting O$^2$-(piperidin-4-yl)1-(N-tert-butyl-N-ethylamino)diazen-1-ium-1,2-diolate (EXAMPLE 17) for O$^2$-[(3R)-pyrrolidin-3-yl]1-(N-tert-butyl-N-ethylamino)diazen-1-ium-1,2-diolate (EXAMPLE 16). $^1$H NMR (500 MHz, CDCl$_3$) δ 4.39-4.32 (m, 1H), 3.10 (q, J=7.0 Hz, 2H), 2.97 (q, J=9.6 Hz, 2H), 2.92-2.85 (m, 2H), 2.57 (ddd, J=11.5, 8.9, 3.3 Hz, 2H), 2.06-1.98 (m, 2H), 1.90 (dtd, J=13.1, 8.6, 3.7 Hz, 2H), 1.23 (s, 9H), 1.03 (t, J=7.0 Hz, 3H); LC-MS: m/z 327.0 (M+H).

Example 34

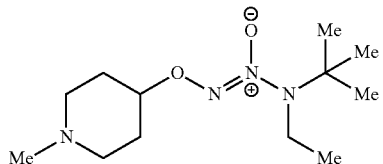 [SMILES: CCN(/[N+]([O-])=N/OC1CCN(C)CC1)C(C)(C)C]

O$^2$-(1-methylpiperidin-4-yl)1-(N-tert-butyl-N-ethylamino)diazen-1-ium-1,2-diolate The title compound was made by following the procedures described in EXAMPLE 5, substituting 1-methylpiperidin-4-ol for N-(tert-butoxycarbonyl)-4-hydroxypiperidine. $^1$H NMR (500 MHz, CDCl$_3$) δ 4.72-4.67 (m, 1H), 3.51 (d, J=11.8 Hz, 2H), 3.12 (q, J=6.9 Hz, 2H), 3.12-3.05 (m, 2H), 2.85 (s, 3H), 2.39-2.28 (m, 2H), 2.31-2.21 (m, 2H), 1.23 (s, 9H), 1.02 (t, J=7.0 Hz, 3H); LC-MS: m/z 259.2 (M+H).

Example 35

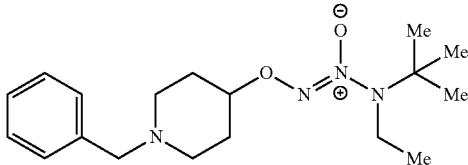 [SMILES: CCN(/[N+]([O-])=N/OC1CCN(Cc2ccccc2)CC1)C(C)(C)C]

O²-(1-benzylpiperidin-4-yl)1-(N-tert-butyl-N-ethylamino)diazen-1-ium-1,2-diolate To a dichloromethane (5 mL) solution of 2-(piperidin-4-yl)1-(N-tert-butyl-N-ethylamino)diazen-1-ium-1,2-diolate (EXAMPLE 17, 371 mg, 0.859 mmol) and triethylamine (0.36 mL, 2.6 mmol) was added benzyl bromide (0.21 mL, 1.8 mmol). The reaction was stirred at room temperature for 14 hours. The reaction was washed with water and extracted with dichloromethane (2×20 mL). The combined organic extracts were dried (magnesium sulfate) and concentrated in vacuo to afford the crude product. Chromatography over silica gel, eluting with hexanes/ethyl acetate, afforded the purified compound. It was dissolved in acetonitrile, stirred with 1.0 equivalent of hydrochloric acid, and lyophilized to afford the hydrochloride salt of the title compound. ¹H NMR (500 MHz, CDCl₃) δ 7.68 (dd, J=6.2, 2.9 Hz, 2H), 7.45-7.42 (m, 3H), 4.72-4.67 (m, 1H), 4.10 (d, J=5.6 Hz, 2H), 3.33-3.25 (m, 2H), 3.10 (q, J=7.0 Hz, 2H), 3.01-2.90 (m, 2H), 2.83-2.71 (m, 2H), 2.22-2.14 (m, 2H), 1.22 (s, 9H), 1.01-0.96 (m, 3H); LC-MS: m/z 335.0 (M+H).

Example 36

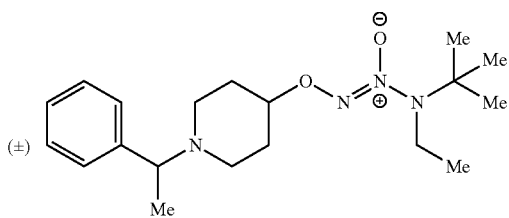 [SMILES: CCN(/[N+]([O-])=N/OC1CCN(C(C)c2ccccc2)CC1)C(C)(C)C]

(±)-O²-[1-(1-phenylethyl)piperidin-4-yl]1-(N-tert-butyl-N-ethylamino)diazen-1-ium-1,2-diolate The title compound was made by following the procedures described in EXAMPLE 35, substituting (±)-(1-bromoethyl)benzene for benzyl bromide. ¹H NMR (500 MHz, CDCl₃) δ 7.33-7.26 (m, 4H), 7.26-7.19 (m, 1H), 4.32-4.26 (m, 1H), 3.40 (q, J=6.7 Hz, 1H), 3.09 (q, J=7.0 Hz, 2H), 2.94-2.86 (m, 1H), 2.76-2.69 (m, 1H), 2.22-2.09 (m, 2H), 2.07-1.94 (m, 2H), 1.90-1.76 (m, 2H), 1.34 (d, J=6.7 Hz, 3H), 1.22 (s, 9H), 1.02 (t, J=7.0 Hz, 3H); LC-MS: m/z 349.4 (M+H).

Example 37

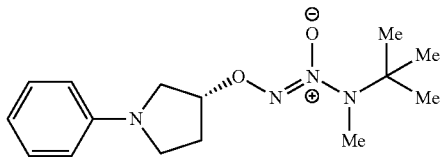 [SMILES: CN(/[N+]([O-])=N/O[C@@H]1CCN(c2ccccc2)C1)C(C)(C)C]

O²-[(3R)-1-phenylpyrrolidin-3-yl]1-(N-tert-butyl-N-methylamino)diazen-1-ium-1,2-diol To a stirring toluene (0.75 mL) suspension of tris(dibenzylideneacetone)dipalladium(0) (36 mg, 0.040 mmol), 2-(dicyclohexylphosphino)-2'-(N,N-dimethylamino) biphenyl (23 mg, 0.059 mmol), and sodium tert-butoxide (57.0 mg, 0.593 mmol) was added bromobenzene (42 μL, 0.40 mmol), followed by a toluene (1 mL) solution of O²-[(3R)-pyrrolidin-3-yl]1-(N-tert-butyl-N-methylamino)diazen-1-ium-1,2-diolate (100 mg, 0.40 mmol). The reaction mixture was heated with stirring to 80° C. for 3 hours. It was cooled down to room temperature, diluted with dichloromethane (10 mL), filtered through diatomaceous earth, and concentrated in vacuo to afford a crude product. Chromatography over silica gel, eluting with hexanes/ethyl acetate, afforded the title compound. ¹H NMR (500 MHz, CDCl₃) δ 7.24 (t, J=7.8 Hz, 2H), 6.73 (t, J=7.3 Hz, 1H), 6.59 (d, J=8.05 Hz, 2H), 5.19-5.08 (m, 1H), 3.70 (dd, J=11.3, 5.1 Hz, 1H), 3.60 (d, J=11.4 Hz, 1H), 3.53 (q, J=8.2 Hz, 1H), 3.45 (td, J=8.8, 3.2 Hz, 1H), 2.84 (s, 3H), 2.48-2.42 (m, 1H), 2.38-2.28 (m, 1H), 1.26 (s, 9H); LC-MS: m/z 293.3 (M+H).

Example 38

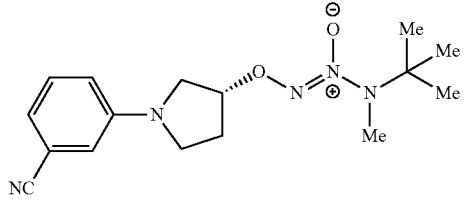 [SMILES: CN(/[N+]([O-])=N/O[C@@H]1CCN(c2cccc(C#N)c2)C1)C(C)(C)C]

O²-[(3R)-1-(3-cyanophenyl)pyrrolidin-3-yl]1-(N-tert-butyl-N-methylamino)diazen-1-ium-1,2-diolate To a stirring toluene (4 mL) suspension of tris(dibenzylideneacetone)dipalladium(0) (254 mg, 0.277 mmol), 2-(di-tert-butylphosphino)biphenyl (248 mg, 0.831 mmol), and sodium tert-butoxide (399 mg, 4.15 mmol) was added 3-bromobenzonitrile (504 mg, 2.77 mmol). After 10 minutes, a toluene (4 mL)/dichloromethane (2 mL) solution of O²-[(3R)-pyrrolidin-3-yl]1-(N-tert-butyl-N-methylamino)diazen-1-ium-1,2-diolate (700 mg, 2.77 mmol) was added to the reaction mixture. The reaction mixture was heated with stirring to 50° C. for 4 hours. It was cooled down to room temperature, diluted with dichloromethane (10 mL), filtered through diatomaceous earth, and concentrated in vacuo to afford a crude product. Chromatography over silica gel, eluting with hexanes/ethyl acetate, afforded the title compound. ¹H NMR (500 MHz, CDCl₃) δ 7.29 (t, J=7.8 Hz, 1H), 6.97 (d, J=7.5 Hz, 1H), 6.77-6.71 (m, 2H), 5.15 (t, J=4.7 Hz, 1H), 3.67 (dd, J=11.5, 4.8 Hz, 1H), 3.60 (d, J=11.5 Hz, 1H), 3.53 (td, J=9.3, 7.0 Hz, 1H), 3.45 (td, J=9.0, 2.6 Hz, 1H), 2.84 (s, 3H), 2.53-2.46 (m, 1H), 2.39-2.29 (m, 1H), 1.26 (s, 9H); LC-MS: m/z 340.3 (M+Na).

Example 39

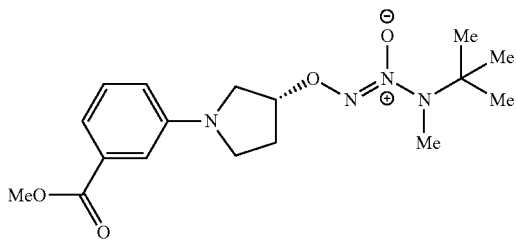 [SMILES: COC(=O)c1cccc(N2CC[C@@H](O/N=[N+](\[O-])N(C)C(C)(C)C)C2)c1]

O²-{(3R)-1-[3-(methoxycarbonyl)phenyl]pyrrolidin-3-yl}1-(N-tert-butyl-N-methylamino)diazen-1-ium-1,2-diolate The title compound was made by following the procedures described in EXAMPLE 37, substituting 2-(dicyclohexylphosphino)biphenyl for 2-(dicyclohexylphosphino)-2'-(N,N-dimethylamino)biphenyl and methyl 3-bromobenzoate for bromobenzene. $^1$H NMR (500 MHz, CDCl$_3$) δ 7.39 (d, J=7.7 Hz, 1H), 7.32-7.27 (m, 1H), 7.24 (s, 1H), 6.75 (dd, J=8.2, 2.6 Hz, 1H), 5.18-5.12 (m, 1H), 3.93 (s, 3H), 3.73 (dd, J=11.4, 5.0 Hz, 1H), 3.65 (d, J=11.4 Hz, 1H), 3.57 (td, J=9.1, 7.0 Hz, 1H), 3.49 (td, J=8.9, 3.0 Hz, 1H), 2.84 (s, 3H), 2.51-2.44 (m, 1H), 2.39-2.30 (m, 1H), 1.26 (s, 9H); LC-MS: m/z 351.3 (M+H).

Example 40

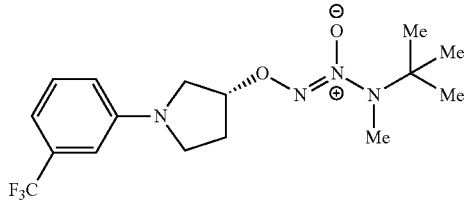 [SMILES: CN(/[N+]([O-])=N/O[C@@H]1CCN(c2cccc(C(F)(F)F)c2)C1)C(C)(C)C]

O²-{(3R)-1-[3-(trifluoromethyl)phenyl]pyrrolidin-3-yl}1-(N-tert-butyl-N-methylamino)diazen-1-ium-1,2-diolate The title compound was made by following the procedures described in EXAMPLE 38, substituting 3-bromobenzotrifluoride for 3-bromobenzonitrile. $^1$H NMR (500 MHz, CDCl$_3$) δ 7.33 (t, J=8.0 Hz, 1H), 6.96 (d, J=7.7 Hz, 1H), 6.76 (s, 1H), 6.71 (d, J=8.5 Hz, 1H), 5.18-5.12 (m, 1H), 3.71 (dd, J=11.4, 4.9 Hz, 1H), 3.65 (d, J=11.4 Hz, 1H), 3.56 (td, J=9.2, 7.0 Hz, 1), 3.48 (td, J=8.9, 2.8 Hz, 1H), 2.84 (s, 3H), 2.53-2.46 (m, 1H), 2.39-2.30 (m, 1H), 1.26 (s, 9H); LC-MS: m/z 361.3 (M+H).

Example 41

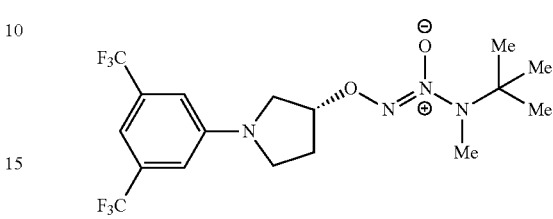

O²-{(3R)-1-[3,5-bis(trifluoromethyl)phenyl]pyrrolidin-3-yl}1-(N-tert-butyl-N-methylamino)diazen-1-ium-1,2-diolate The title compound was made by following the procedures described in EXAMPLE 38, substituting 3,5-bis(trifluoromethyl)bromobenzene for 3-bromobenzonitrile. $^1$H NMR (500 MHz, CDCl$_3$) δ 7.17 (s, 1H), 6.88 (s, 2H), 5.17-5.14 (m, 1H), 3.73 (dd, J=11.6, 4.5 Hz, 1H), 3.72-3.66 (m, 1H), 3.60 (td, J=9.4, 7.0 Hz, 1H), 3.53 (td, J=9.0, 2.5 Hz, 1H), 2.84 (s, 3H), 2.54 (dd, J=14.1, 6.7 Hz, 1H), 2.36 (dtd, J=14.0, 9.4, 5.1 Hz, 1H), 1.25 (s, 9H); LC-MS: m/z 429.3 (M+H).

Example 42

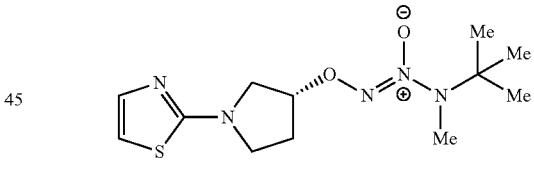

O²-[(3R)-1-(1,3-thiazol-2-yl)pyrrolidin-3-yl]1-(N-tert-butyl-N-methylamino)diazen-1-ium-1,2-diolate Chloro[2-(di-tert-butylphosphino)-2',4',6'-triisopropyl-1,1'-biphenyl][2-(2-aminoethyl)phenyl)]palladium(II) (222 mg, 0.331 mmol), O²-[(3R)-pyrrolidin-3-yl]1-(N-tert-butyl-N-methylamino)diazen-1-ium-1,2-diolate (EXAMPLE 15, 716 mg, 3.31 mmol), and 2-bromothiazole (0.295 mL, 3.31 mmol) were combined and diluted with tert-amyl alcohol (25 mL). To the stirring suspension was added potassium tert-butoxide (1.0 M in tert-amyl alcohol, 10 mL, 10 mmol). The reaction vessel was sealed and heated to 50° C. with stirring for 16 hours. The reaction mixture was cooled to room temperature, filtered through diatomaceous earth, concentrated in vacuo and purified by reversed phase HPLC to afford the title compound. $^1$H NMR (500 MHz, CDCl$_3$) δ 7.38 (s, 1H), 6.69

(s, 1H), 5.23 (s, 1H), 4.18-3.71 (m, 4H), 2.84 (s, 3H), 2.71-2.58 (m, 1H), 2.59-2.39 (m, 1H), 1.25 (s, 9H); LC-MS: m/z 300.3 (M+H).

Example 43

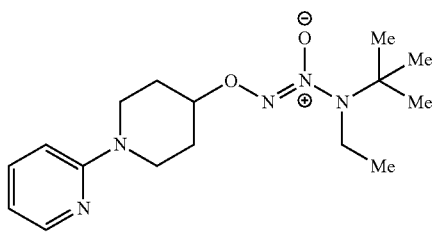 [SMILES: CCN(/[N+]([O-])=N/OC1CCN(c2ccccn2)CC1)C(C)(C)C]

O²-[1-(pyridin-2-yl)piperidin-4-yl]1-(N-tert-butyl-N-methylamino)diazen-1-ium-1,2-diolate Chloro(2-dicyclohexylphosphino-2',6'-dimethoxy-1,1'-biphenyl)[2-(2-aminoethylphenyl)]palladium(II) (359 mg, 0.472 mmol), the hydrochloride salt of O²-(piperidin-4-yl)1-(N-tert-butyl-N-ethylamino)diazen-1-ium-1,2-diolate (EXAMPLE 17, 330 mg, 1.18 mmol), and 2-bromopyridine (0.226 mL, 2.36 mmol) were combined and diluted with tetrahydrofuran (5 mL). To the stirring suspension was added potassium tert-butoxide (1.0 M in tetrahydrofuran, 3.54 mL, 3.54 mmol). The reaction vessel was sealed and stirred at 30° C. for 24 hours. The reaction mixture was cooled to room temperature, filtered through diatomaceous earth, concentrated in vacuo and purified by reversed phase HPLC to afford the title compound. ¹H NMR (500 MHz, CDCl₃) δ 8.17 (dd, J=4.9, 1.9 Hz, 1H), 7.46 (t, J=7.9 Hz, 1H), 6.68 (d, J=8.6 Hz, 1H), 6.60 (dd, J=7.1, 5.0 Hz, 1H), 4.59-4.53 (m, 1H), 4.05 (dt, J=13.4, 4.9 Hz, 2H), 3.26 (ddd, J=13.3, 9.4, 3.2 Hz, 2H), 3.11 (q, J=7.0 Hz, 2H), 2.16-2.08 (m, 2H), 1.90 (dtd, J=13.1, 9.2, 3.9 Hz, 2H), 1.24 (s, 9H), 1.04 (t, J=7.0 Hz, 3H); LC-MS: m/z 322.3 (M+H).

Example 44

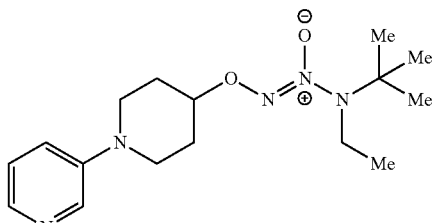

O²-[1-(pyridin-3-yl)piperidin-4-yl]1-(N-tert-butyl-N-methylamino)diazen-1-ium-1,2-diolate The title compound was made by following the procedures described in EXAMPLE 43, substituting chloro[2-(di-tert-butylphosphino)-2',4',6'-triisopropyl-1,1'-biphenyl][2-(2-aminoethyl)phenyl)]palladium(II) for chloro(2-dicyclohexylphosphino-2',6'-dimethoxy-1,1'-biphenyl)[2-(2-aminoethylphenyl)]palladium(II), and 3-bromopyridine for 2-bromopyridine. ¹H NMR (500 MHz, CDCl₃) δ 8.33 (s, 1H), 8.09 (s, 1H), 7.20 (d, J=8.6 Hz, 1H), 7.16 (dd, J=8.5, 4.4 Hz, 1H), 4.55-4.49 (m, 1H), 3.60-3.54 (m, 2H), 3.12 (q, J=7.0 Hz, 2H), 3.10-3.04 (m, 2H), 2.18-2.13 (m, 2H), 2.04-1.96 (m, 2H), 1.25 (s, 9H), 1.05 (t, J=7.0 Hz, 3H); LC-MS: m/z 322.3 (M+H).

Example 45

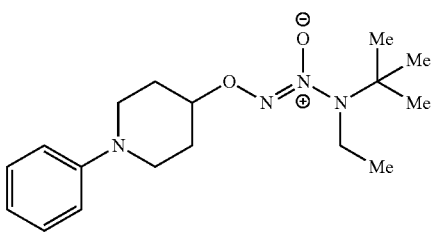 [SMILES: CCN(/[N+]([O-])=N/OC1CCN(c2ccccc2)CC1)C(C)(C)C]

O²-(1-phenylpiperidin-4-yl)1-(N-tert-butyl-N-ethylamino)diazen-1-ium-1,2-diolate To a dichloromethane (25 mL) solution of (2-(piperidin-4-yl)1-(N-tert-butyl-N-ethylamino)diazen-1-ium-1,2-diolate (EXAMPLE 17, 5.03 g, 13.4 mmol) and triethylamine (6.0 mL, 43 mmol) was added a pre-mixed slurry of copper(II) acetate (2.78 g, 15.3 mmol) and phenylboronic acid (3.28 g, 26.9 mmol). The blue mixture was then warmed to 30° C. and stirred for 24 hours open to the air with a condenser. The slurry was filtered, rinsed with dichloromethane, and water (200 mL) was added to the filtrate. Hydrochloric acid (1 M) was added to help separation and dissolve copper salts. The combined organic layers were washed with brine, dried (magnesium sulfate), and concentrated in vacuo to afford the crude product. Chromatography over silica gel, eluting with dichloromethane/methanol, afforded the title compound. ¹H NMR (500 MHz, CDCl₃) δ 7.25 (t, J=7.4 Hz, 2H), 6.94 (d, J=8.2 Hz, 2H), 6.84 (t, J=7.3 Hz, 1H), 4.52-4.45 (m, 1H), 3.57 (dt, J=12.6, 4.9 Hz, 2H), 3.12 (q, J=7.0 Hz, 2H), 3.00 (ddd, J=12.6, 9.5, 3.2 Hz, 2H), 2.18-2.13 (m, 2H), 1.99 (dtd, J=13.0, 9.2, 3.8 Hz, 2H), 1.25 (s, 9H), 1.05 (t, J=7.0 Hz, 3H); LC-MS m/z 321.3 (M+H).

Example 46

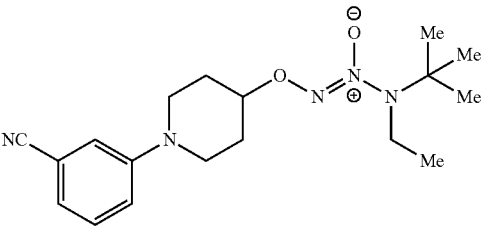 [SMILES: CCN(/[N+]([O-])=N/OC1CCN(c2cccc(C#N)c2)CC1)C(C)(C)C]

O²-[1-(3-cyanophenyl)piperidin-4-yl]1-(N-tert-butyl-N-ethylamino)diazen-1-ium-1,2-diolate Step A: 3-(4-hydroxypiperidin-1-yl)benzonitrile A dimethylsulfoxide (30 mL) solution of 3-fluorobenzonitrile (9.73 g, 80.0 mmol) and 4-hydroxypiperidine (8.15 g, 81 mmol) was heated to 100° C. and stirred for 5 hours. The solution was cooled to room temperature and added dropwise to water (500 mL). The mixture was extracted with ethyl acetate (2×300 mL) and washed with water (2×200 mL), brine (200 mL), dried (magnesium sulfate) and concentrated in vacuo to afford the crude product. Chromatography over silica gel, eluting with hexanes/ethyl acetate, afforded the title compound.

Step B: O$^2$-[1-(3-cyanophenyl)piperidin-4-yl]1-(N-tert-butyl-N-ethylamino)diazen-1-ium-1,2-diolate The title compound was made by following the procedures described in EXAMPLE 5, substituting 3-(4-hydroxypiperidin-1-yl)benzonitrile for N-(tert-butoxycarbonyl)-4-hydroxypiperidine. $^1$H NMR (500 MHz, CDCl$_3$) δ 7.30 (dt, J=9.5, 3.7 Hz, 1H), 7.13-7.10 (m, 2H), 7.08 (d, J=7.6 Hz, 1H), 4.53 (tt, J=8.4, 3.9 Hz, 1H), 3.60-3.53 (m, 2H), 3.14-3.05 (m, 4H), 2.19-2.11 (m, 2H), 2.02-1.94 (m, 2H), 1.25 (s, 9H), 1.05 (t, J=7.0 Hz, 3H); LC-MS m/z 346.3 (M+H).

Example 47

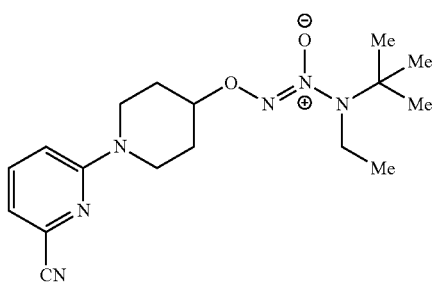 [SMILES: CCN(/[N+]([O-])=N/OC1CCN(c2cccc(C#N)n2)CC1)C(C)(C)C]

O$^2$-[1-(6-cyanpyridin-2-yl)piperidin-4-yl]1-(N-tert-butyl-N-ethylamino)diazen-1-ium-1,2-diolate The title compound was made by following the procedures described in EXAMPLE 46, substituting 6-bromopyridine-2-carbonitrile for 3-fluorobenzonitrile in step A. $^1$H NMR (500 MHz, CDCl$_3$) δ 7.50 (dd, J=8.8, 7.2 Hz, 1H), 6.95 (d, J=7.2 Hz, 1H), 6.84 (d, J=8.8 Hz, 1H), 4.62-4.56 (m, 1H), 4.02 (ddd, J=13.5, 6.3, 4.1 Hz, 2H), 3.37 (ddd, J=13.6, 8.9, 3.5 Hz, 2H), 3.11 (q, J=7.0 Hz, 2H), 2.14-2.06 (m, 2H), 1.93-1.84 (m, 2H), 1.24 (s, 9H), 1.04 (t, J=7.0 Hz, 3H); LC-MS: m/z 369.4 (M+Na).

Example 48

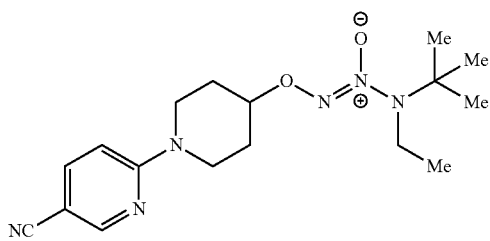 [SMILES: CCN(/[N+]([O-])=N/OC1CCN(c2ccc(C#N)cn2)CC1)C(C)(C)C]

O$^2$-[1-(5-cyanopyridin-2-yl)piperidin-4-yl]1-(N-tert-butyl-N-ethylamino)diazen-1-ium-1,2-diolate The title compound was made by following the procedures described in EXAMPLE 46, substituting 6-chloropyridine-3-carbonitrile for 3-fluorobenzonitrile in step A. $^1$H NMR (500 MHz, CDCl$_3$) δ 8.40 (d, J=2.3 Hz, 1H), 7.60 (dd, J=9.1, 2.4 Hz, 1H), 6.63 (d, J=9.1 Hz, 1H), 4.65-4.58 (m, 1H), 4.05 (ddd, J=13.6, 6.9, 4.0 Hz, 2H), 3.49 (ddd, J=13.7, 8.6, 3.7 Hz, 2H), 3.11 (q, J=7.0 Hz, 2H), 2.13-2.06 (m, 2H), 1.91 (dtd, J=13.4, 8.3, 3.9 Hz, 2H), 1.24 (s, 9H), 1.04 (t, J=7.0 Hz, 3H); LC-MS: m/z 369.4 (M+Na).

Example 49

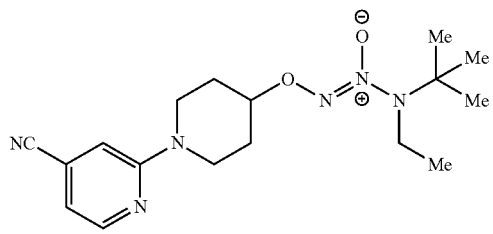

O$^2$-[1-(4-cyanopyridin-2-yl)piperidin-4-yl]1-(N-tert-butyl-N-ethylamino)diazen-1-ium-1,2-diolate The title compound was made by following the procedures described in EXAMPLE 46, substituting 2-chloropyridine-4-carbonitrile for 3-fluorobenzonitrile in step A. $^1$H NMR (500 MHz, CDCl$_3$) δ 8.26 (d, J=5.0 Hz, 1H), 6.84 (s, 1H), 6.74 (dd, J=5.0, 1.1 Hz, 1H), 4.63-4.56 (m, 1H), 4.01 (ddd, J=13.4, 6.4, 4.1 Hz, 2H), 3.42-3.35 (m, 2H), 3.12 (q, J=7.0 Hz, 2H), 2.14-2.07 (m, 2H), 1.91 (dtd, J=13.3, 8.6, 3.9 Hz, 2H), 1.24 (s, 9H), 1.04 (t, J=7.0 Hz, 3H); LC-MS: m/z 369.4 (M+Na).

Example 50

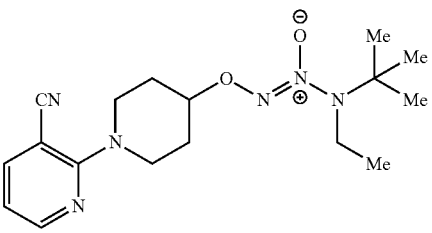 [SMILES: CCN(/[N+]([O-])=N/OC1CCN(c2ncccc2C#N)CC1)C(C)(C)C]

O$^2$-[1-(3-cyanpyridin-2-yl piperidin-4-yl]1-(N-tert-butyl-N-ethylamino)diazen-1-ium-1,2-diolate The title compound was made by following the procedures described in EXAMPLE 46, substituting 2-chloropyridine-4-carbonitrile for 3-fluorobenzonitrile in step A. $^1$H NMR (500 MHz, CDCl$_3$) δ 8.33 (dd, J=4.8, 2.0 Hz, 1H), 7.76 (dd, J=7.7, 2.0 Hz, 1H), 6.75 (dd, J=7.7, 4.8 Hz, 1H), 4.63-4.56 (m, 1H), 4.07 (ddd, J=13.2, 6.5, 3.8 Hz, 2H), 3.49 (ddd, J=13.6, 8.8, 3.4

Hz, 2H), 3.11 (q, J=7.0 Hz, 2H), 2.19-2.12 (m, 2H), 2.04-1.96 (m, 2H), 1.24 (s, 9H), 1.04 (t, J=7.0 Hz, 3H); LC-MS: m/z 369.4 (M+Na).

Example 51

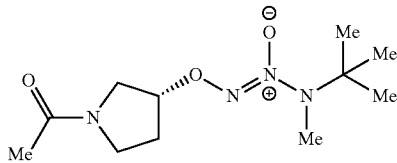 [SMILES: CC(=O)N1CC[C@@H](O/N=[N+](\[O-])N(C)C(C)(C)C)C1]

O²-[(3R)-1-acetylpyrrolidin-3-yl]1-(N-tert-butyl-N-methylamino)diazen-1-ium-1,2-diolate To a stirring dichloromethane (6 mL) solution of O²-[(3R)-pyrrolidin-3-yl]1-(N-tert-butyl-N-methylamino)diazen-1-ium-1,2-diolate (EXAMPLE 15, 500 mg, 2.31 mmol) and triethylamine (644 µL, 4.62 mmol) was added acetyl chloride (247 µL, 3.47 mmol). The reaction mixture was stirred for 16 hours, concentrated in vacuo, and concentrated in vacuo to afford the crude product Chromatography over silica gel, eluting with dichloromethane/methanol, afforded the title compound as a yellow liquid. $^1$H NMR (500 MHz, CDCl$_3$) major rotomer δ 5.03-4.99 (m, 1H), 3.93 (d, J=14.2 Hz, 1H), 3.84-3.54 (m, 3H), 2.84 (s, 3H), 2.45 (ddd, J=14.2, 6.6, 2.1 Hz, 1H), 2.30-2.20 (m, 1H), 2.14 (s, 3H), 1.25 (s, 9H); minor rotomer δ 5.05-5.02 (m, 1H), 3.84-3.54 (m, 4H), 2.84 (s, 3H), 2.41-2.35 (m, 1H), 2.22-2.09 (m, 1H), 2.11 (s, 3H), 1.26 (s, 9H); LC-MS: m/z 281.0 (M+Na).

Example 52

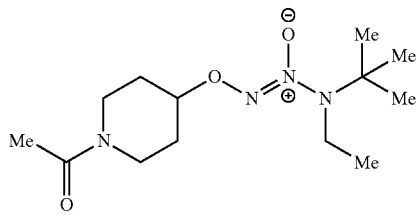 [SMILES: CCN(/[N+]([O-])=N/OC1CCN(C(C)=O)CC1)C(C)(C)C]

O²-(1-acetylpiperidin-4-yl)1-(N-tert-butyl-N-ethylamino)diazen-1-ium-1,2-diolate The title compound was made by following the procedures described in EXAMPLE 51, substituting O²-(piperidin-4-yl)1-(N-tert-butyl-N-ethylamino)diazen-1-ium-1,2-diolate (EXAMPLE 17) for O²-[(3R)-pyrrolidin-3-yl]1-(N-tert-butyl-N-methylamino)diazen-1-ium-1,2-diolate (EXAMPLE 15). $^1$H NMR (500 MHz, CDCl$_3$) δ 4.54 (tt, J=8.0, 3.7 Hz, 1H), 4.03-3.97 (m, 2H, rotamer 1), 3.72 (ddd, J=13.8, 6.9, 3.9 Hz, 2H, rotamer 2), 3.36-3.27 (m, 2H), 3.11 (q, J=7.0 Hz, 2H), 2.10 (s, 3H), 2.04-1.96 (m, 2H), 1.90-1.80 (m, 2H), 1.24 (s, 9H), 1.03 (t, J=7.0 Hz, 3H); LC-MS: m/z 308.9 (M+Na).

Example 53

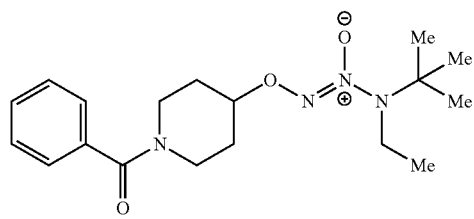 [SMILES: CCN(/[N+]([O-])=N/OC1CCN(C(=O)c2ccccc2)CC1)C(C)(C)C]

O²-[1-(phenylcarbonyl)piperidin-4-yl]1-(N-tert-butyl-N-ethylamino)diazen-1-ium-1,2-diolate The title compound was made by following the procedures described in EXAMPLE 52, substituting benzoyl chloride for acetyl chloride. $^1$H NMR (500 MHz, CDCl$_3$) δ 7.42-7.37 (m, 5H), 4.62-4.56 (m, 1H), 3.71-3.68 (m, 1H, rotamer 1), 3.53-3.44 (m, 1H, rotamer 2), 3.31-3.28 (m, 2H), 3.11 (q, J=7.0 Hz, 2H), 2.13-1.84 (m, 4H), 1.23 (s, 9H), 1.03 (t, J=7.0 Hz, 3H); LC-MS: m/z 370.9 (M+Na).

Example 54

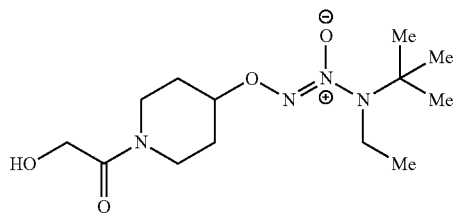 [SMILES: CCN(/[N+]([O-])=N/OC1CCN(C(=O)CO)CC1)C(C)(C)C]

O²-[1-(hydroxyacetyl)piperidin-4-yl]1-(N-tert-butyl-N-ethylamino)diazen-1-ium-1,2-diolate To a dichloromethane (5 mL) solution of glycolic acid (203 mg, 2.67 mmol) was added the hydrochloride salt of O²-(piperidin-4-yl)1-(N-tert-butyl-N-ethylamino)diazen-1-ium-1,2-diolate (326 mg, 0.755 mmol), 1-hydroxybenzotriazole hydrate (297 mg, 2.20 mmol), N-methylmorpholine (0.25 mL, 2.3 mmol), and 1-ethyl-3-(3'-dimethylaminopropyl)carbodiimide hydrochloride (527 mg, 2.75 mmol). The reaction was stirred at room temperature for 18 hours. The reaction mixture was quenched with saturated aqueous ammonium chloride solution (2 mL) and diluted with water (5 mL). The reaction mixture was extracted with dichloromethane (3×20 mL), and the combined organics were washed with water, dried (magnesium sulfate), and concentrated in vacuo to afford the crude product. It was purified by mass-directed reversed-phase HPLC to afford the title compound. $^1$H NMR (500 MHz, CDCl$_3$) δ 4.63-4.57 (m, 1H), 4.21 (s, 2H), 3.94-3.87 (m, 1H, rotamer 1), 3.59-3.46 (m, 2H), 3.19 (ddd, J=13.8, 7.6, 4.0 Hz, 1H, rotamer 2), 3.12 (q, J=7.0

Hz, 2H), 2.06-1.98 (m, 2H), 1.95-1.86 (m, 2H), 1.24 (s, 9H), 1.03 (t, J=7.0 Hz, 3H); LC-MS: m/z 325.0 (M+Na).

Example 55

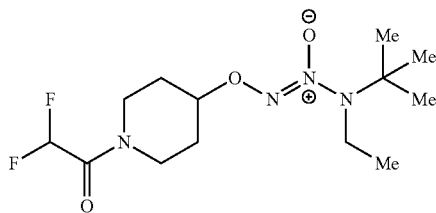 [SMILES: CCN(/[N+]([O-])=N/OC1CCN(C(=O)C(F)F)CC1)C(C)(C)C]

O$^2$-[1-(difluoroacetyl)piperidin-4-yl]1-(N-tert-butyl-N-ethylamino)diaz-1-ium-1,2-diolate The title compound was made by following the procedures described in EXAMPLE 54, substituting difluoroacetic acid for glycolic acid. $^1$H NMR (500 MHz, CDCl$_3$) δ 6.10 (t, J=53.8 Hz, 1H), 4.63-4.57 (m, 1H), 3.90-3.80 (m, 2H), 3.59-3.49 (m, 2H), 3.11 (q, J=7.0 Hz, 2H), 2.06-2.00 (m, 2H), 2.01-1.89 (m, 2H), 1.24 (s, 9H), 1.03 (t, J=7.0 Hz, 3H); LC-MS: m/z 344.9 (M+Na).

Example 56

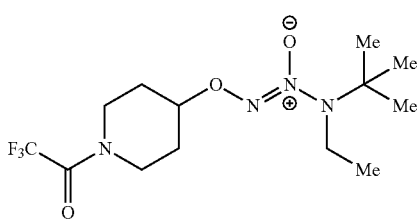 [SMILES: CCN(/[N+]([O-])=N/OC1CCN(C(=O)C(F)(F)F)CC1)C(C)(C)C]

O$^2$-[1-(trifluoroacetyl)piperidin-4-yl]1-(N-tert-butyl-N-ethylamino)diazen-1-ium-1,2-diolate To a dichloromethane (10 mL) solution of the hydrochloride salt of O$^2$-(piperidin-4-yl)1-(N-tert-butyl-N-ethylamino)diazen-1-ium-1,2-diolate (744 mg, 2.65 mmol) and triethylamine (0.95 mL, 6.8 mmol) at 0° C. was added dropwise trifluoroacetic anhydride (0.45 mL, 3.2 mmol) over 2 minutes. Following the addition, the reaction mixture was allowed to warm to room temperature and stirred for 1.5 hour. The reaction mixture was diluted with water (5 mL) and quenched with saturated aqueous sodium bicarbonate solution (10 mL). It was extracted with dichloromethane (25 mL), and the combined organic extracts were dried (magnesium sulfate) and concentrated in vacuo to afford the crude product. Chromatography over silica gel, eluting with hexanes/ethyl acetate, afforded the title compound. $^1$H NMR (500 MHz, CDCl$_3$) δ 4.65-4.59 (m, 1H), 3.88-3.76 (m, 2H), 3.70-3.64 (m, 1H, rotamer 1), 3.57-3.51 (m, 1H, rotamer 2), 3.11 (q, J=7.0 Hz, 2H), 2.07-1.92 (m, 4H), 1.24 (s, 9H), 1.03 (t, J=7.0 Hz, 3H); LC-MS: m/z 362.9 (M+Na).

Example 57

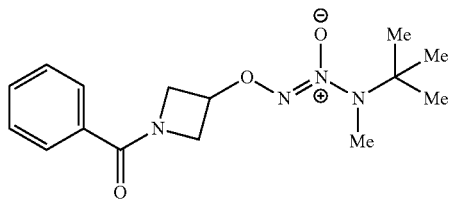 [SMILES: CN(/[N+]([O-])=N/OC1CN(C(=O)c2ccccc2)C1)C(C)(C)C]

O$^2$-[1-(phenylcarbonyl)azetidin-3-yl]1-(N-tert-butyl-N-methylamino)diazen-1-ium-1,2-diolate Step A: O$^2$-(azetidin-3-yl)1-(N-tert-butyl-N-methylamino)diazen-1-ium-1,2-diolate The title compound was made by following the procedures described in EXAMPLE 15, substituting O$^2$-[1-(tert-butoxycarbonyl)azetidin-3-yl]1-(N-tert-butyl-N-methylamino)diazen-1-ium-1,2-diolate (EXAMPLE 13) for O$^2$-[(3R)-1-(tert-butoxycarbonyl)pyrrolidin-3-yl]1-(N-tert-butyl-N-methylamino)diazen-1-ium-1,2-diolate (EXAMPLE 1).

Step B: O$^2$-[1-(phenylcarbonyl)azetidin-3-yl]1-(N-tert-butyl-N-methylamino)diazen-1-ium-1,2-diolate The title compound was made by following the procedures described in EXAMPLE 53, substituting O$^2$-(azetidin-3-yl) 1-(N-tert-butyl-N-methylamino)diazen-1-ium-1,2-diolate for O$^2$-(piperidin-4-yl)1-(N-tert-butyl-N-ethylamino)diazen-1-ium-1,2-diolate (EXAMPLE 17). $^1$H NMR (500 MHz, CDCl$_3$) δ 7.59 (m, 2H), 7.41 (m, 1H), 7.40 (m, 2H), 5.15 (m, 1H), 4.53-4.20 (m, 4H), 3.29 (m, 3H), 1.22 (m, 9H).

Example 58

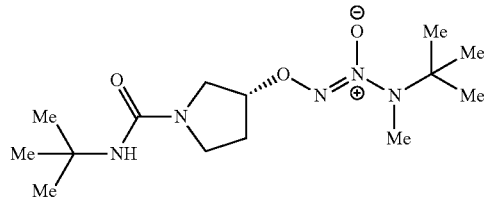 [SMILES: CN(/[N+]([O-])=N/O[C@@H]1CCN(C(=O)NC(C)(C)C)C1)C(C)(C)C]

O$^2$-[(3R)-1-(tert-butylcarbamoyl)pyrrolidin-3-yl]1-(N-tert-butyl-N-methylamino)diazen-1-ium-1,2-diolate To a stirring dichloromethane (10 mL) and diethyl ether (20 mL) solution of the hydrochloride salt of O$^2$-[(3R)-pyrrolidin-3-yl]1-(N-tert-butyl-N-methylamino)diazen-1-ium-1,2-diolate (EXAMPLE 15, 3.00 g, 11.9 mmol) and triethylamine (5.79 mL, 41.5 mmol) was added tert-butyl isocyanate (2.85 mL, 24.9 mmol). The reaction mixture was stirred for 16 hours, concentrated in vacuo, redissolved in ether (70 mL), filtered and concentrated in vacuo to afford the crude product.

Chromatography over silica gel, eluting with hexanes/ethyl acetate, afforded the title compound as a yellow liquid. ¹H NMR (500 MHz, CDCl₁) δ 4.99-4.96 (m, 1H), 4.04 (s, 1H), 3.69 (d, J=12.1 Hz, 1H), 3.62 (dd, J=12.1, 4.7 Hz, 1H), 3.50-3.41 (m, 2H), 2.84 (s, 3H), 2.39-2.30 (m, 1H), 2.19 (dtd, J=13.9, 9.4, 5.0 Hz, 1H), 1.37 (s, 9H), 1.25 (s, 9H); LC-MS: m/z 316.4 (M+H).

Example 59

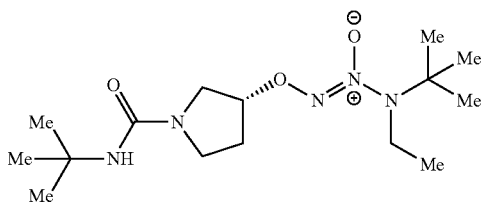 [SMILES: CCN(/[N+]([O-])=N/O[C@@H]1CCN(C(=O)NC(C)(C)C)C1)C(C)(C)C]

O²-[(3R)-1-(tert-butylcarbamoyl)pyrrolidin-3-yl]1-(N-tert-butyl-N-ethylamino)diazen-1-ium-1,2-diolate The title compound was made by following the procedures described in EXAMPLE 51, substituting O²-[(3R)-pyrrolidin-3-yl]1-(N-tert-butyl-N-ethylamino)diazen-1-ium-1,2-diolate (EXAMPLE 16) for O²-[(3R)-pyrrolidin-3-yl]1-(N-tert-butyl-N-methylamino)diazen-1-ium-1,2-diolate (EXAMPLE 15). ¹H NMR (500 MHz, CDCl₃) δ 5.30 (m, 1H), 4.03 (s, 1H), 3.67-3.56 (m, 2H), 3.44 (dd, J=9.4, 4.7 Hz, 2H), 3.10 (q, J=7.0 Hz, 2H), 2.31 (d, J=13.7 Hz, 1H), 2.16 (dtd, J=13.9, 9.4, 5.0 Hz, 1H), 1.34 (s, 9H), 1.23 (s, 9H), 1.03 (t, J=7.0 Hz, 3H); LC-MS: m/z 330 (M+H).

Example 60

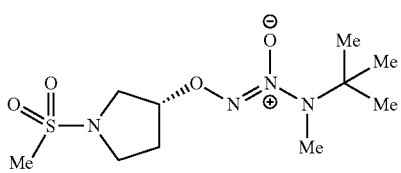 [SMILES: CN(/[N+]([O-])=N/O[C@@H]1CCN(S(C)(=O)=O)C1)C(C)(C)C]

O²-[(3R)-1-(methylsulfonyl)pyrrolidin-3-yl]1-(N-tert-butyl-N-methylamino)diazen-1-ium-1,2-diolate The title compound was made by following the procedures described in EXAMPLE 51, substituting methanesulfonyl chloride for acetyl chloride. ¹H NMR (500 MHz, CDCl₃) δ 5.01-4.99 (m, 1H), 3.67 (d, J=2.7 Hz, 2H), 3.61 (td, J=9.3, 2.1 Hz, 1H), 3.43 (td, J=10.1, 6.8 Hz, 1H), 2.89 (s, 3H), 2.83 (s, 3H), 2.40 (dd, J=14.2, 6.8 Hz, 1H), 2.28-2.18 (m, 1H), 1.26 (s, 9H); LC-MS: m/z 317.3 (M+Na).

Example 61

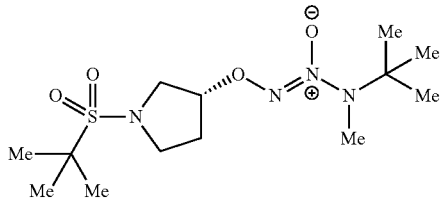 [SMILES: CN(/[N+]([O-])=N/O[C@@H]1CCN(S(=O)(=O)C(C)(C)C)C1)C(C)(C)C]

O²-[(3R)-1-(tert-butylsulfonyl)pyrrolidin-3-yl]1-(N-tert-butyl-N-methylamino)diazen-1-ium-1,2-diolate Step A: O²-[(3R)-1-(tert-butylsulfinyl)pyrrolidin-3-yl]1-(N-tert-butyl-N-methylamino)diazen-1-ium-1,2-diolate The title compound was made by following the procedures described in EXAMPLE 51, substituting tert-butylsulfinyl chloride for acetyl chloride. The crude product was used in the subsequent step without further purification.

Step B: O²-[(3R)-1-(tert-butylsulfonyl)pyrrolidin-3-yl]1-(N-tert-butyl-N-methylamino)diazen-1-ium-1,2-diolate To a stirring dichloromethane (20 mL) solution of O²-[(3R)-1-(tert-butylsulfinyl)pyrrolidin-3-yl]1-(N-tert-butyl-N-methylamino)diazen-1-ium-1,2-diolate (0.951 g, 2.97 mmol) at 0° C. was added 3-chloroperbenzoic acid (1.16 g, 5.18 mmol). The reaction mixture was allowed to warm to room temperature and stirred for 2 hours. It was extracted with dichloromethane (2×20 mL), and the combined organic extracts were washed with saturated aqueous sodium bicarbonate solution, dried (magnesium sulfate), filtered and concentrated in vacuo to afford the crude product. Chromatography over silica gel, eluting with hexanes/ethyl acetate, afforded the title compound. ¹H NMR (500 MHz, CDCl₃) δ 5.03 (t, J=4.8 Hz, 1H), 3.90 (dd, J=12.1, 4.9 Hz, 1H), 3.78 (td, J=9.3, 2.6 Hz, 1H), 3.66 (d, J=12.1 Hz, 1H), 3.55 (td, J=9.9, 6.7 Hz, 1H), 2.83 (s, 3H), 2.34-2.28 (m, 1H), 2.24-2.15 (m, 1H), 1.41 (s, 9H), 1.26 (s, 9H); LC-MS: m/z 359.3 (M+Na).

Example 62

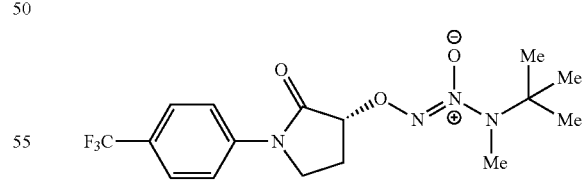

O²-{(3R-2-oxo-1-[4-(trifluoromethyl)phenyl]pyrrolidin-3-yl}1-(N-tert-butyl-N-methylamino)diazen-1-ium-1,2-diolate Step A: (3S)-3-hydroxy-1-[4-(trifluoromethyl)phenyl]pyrrolidin-2-one To a 1,4-dioxane (20 mL) solution of (3S)-3-hydroxypyrrolidin-2-one (372 mg, 3.68 mmol) and 1-bromo-4-(trifluoromethyl)benzene (508 μL, 3.68 mmol) at room temperature was added 4,5-bis(diphenylphosphino)-9,9-dimethylxanthene (64 mg, 0.11 mmol), palladium(II) acetate (17 mg, 0.070 mmol) and cesium carbonate (1.80 g, 5.52 mmol). After stirring at 80° C. for 16 hours, the reaction mixture was allowed to cool down to room temperature and partitioned between diethyl ether (100 mL) and brine (100 mL). The organic layer was washed with brine (2×100 mL), dried (magnesium sulfate) and concentrated in vacuo to afford the crude product. Chromatography over silica gel, eluting with hexanes/ethyl acetate, afforded the title compound. $^1$H NMR (500 MHz, CDCl$_3$) δ 7.81 (d, J=8.6 Hz, 2H), 7.64 (d, J=8.7 Hz, 2H), 4.52-4.48 (m, 1H), 3.89-3.77 (m, 2H), 3.05 (br s, 1H), 2.68-2.62 (m, 1H), 2.18-2.09 (m, 1H).

Step B: (3S)-2-oxo-1-[4-(trifluoromethyl)phenyl] pyrrolidin-3-yl 4-(trifluoromethyl)benzenesulfonate To a dichloromethane (10 mL) solution of (3S)-3-hydroxy-1-[4-(trifluoromethyl)phenyl]pyrrolidin-2-one (691 mg, 2.82 mmol), triethylamine (589 μL, 4.23 mmol), and 4-(dimethylamino)pyridine (69 mg, 0.56 mmol) at 0° C. was added a dichloromethane (10 mL) solution of 4-(trifluoromethyl)benzenesulfonyl chloride (827 mg, 3.38 mmol) dropwise. After stirring for 3 hours, the mixture was partitioned between diethyl ether (100 mL) and water (100 mL). The organic layer was washed with brine (2×100 mL), dried (magnesium sulfate) and concentrated to give the title compound, which was subjected to the next step without further purification. $^1$H NMR (500 MHz, CDCl$_3$) δ 8.19 (d, J=7.9 Hz, 2H), 7.85 (d, J=7.4 Hz, 2H), 7.71 (d, J=8.6 Hz, 2H), 7.62 (d, J=8.7 Hz, 2H), 5.25 (t, J=8.0 Hz, 1H), 3.98-3.93 (m, 1H), 3.85-3.81 (m, 1H), 2.81-2.75 (m, 1H), 2.49-2.43 (m, 1H).

Step C: O$^2$-{(3R)-2-oxo-1-[4-trifluoromethyl)phenyl]pyrrolidin-3-yl}1-(N-tert-butyl-N-methylamino) diazen-1-ium-1,2-diolate The title compound was prepared using procedures described for EXAMPLE 1, substituting (3S)-2-oxo-1-[4-(trifluoromethyl)phenyl]pyrrolidin-3-yl 4-(trifluoromethyl) benzenesulfonate for tert-butyl (3S)-3-({[4-(trifluoromethyl)phenyl]sulfonyl}oxy)pyrrolidine-1-carboxylate in Step B. $^1$H NMR (500 MHz, CDCl$_3$) δ 7.79 (d, J=8.6 Hz, 2H), 7.62 (d, J=8.7 Hz, 2H), 5.15 (t, J=8.2 Hz, 1H), 3.99-3.91 (m, 1H), 3.88-3.82 (m, 1H), 2.83 (s, 3H), 2.73-2.66 (m, 1H), 2.51-2.43 (m, 1H), 1.26 (s, 9H).

Examples 63-78

The following examples were prepared using procedures analogous to those described for EXAMPLE 62, substituting appropriate halides for 1-bromo-4-(trifluoromethyl)benzene in Step A. (LC conditions: Ace 3 C18 3.5 μm 3×50 mm column with gradient 10:90-90:10 v/v CH$_3$CN/H$_2$O+v 0.1% TFA over 2.80 min then hold at 90:10 v/v CH$_3$CN/H$_2$O+v 0.1% TFA for 1.2 min; flow rate 1.0 mL/min, UV wavelength 254 nm).

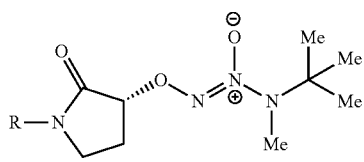

| Example | R | HPLC R$_t$ (min) | MS M + H (or M + Na) |
|---|---|---|---|
| 63 | ![pyridyl-CF3] | 3.05 | 376.2 (398.2) |
| 64 | ![3-OCH3-phenyl] | 2.73 | (359.2) |
| 65 | ![3-CF3-phenyl] | 3.02 | (397.2) |
| 66 | ![3,5-bis-CF3-phenyl] | 3.24 | (465.0) |
| 67 | ![3-CN-phenyl] | 2.74 | (354.2) |
| 68 | H | 2.00 | (253.2) |
| 69 | ![benzyl] | 2.72 | (343.2) |
| 70 | ![3-OCF3-phenyl] | 3.91 | 391.2 (413.2) |
| 71 | ![3-Cl-phenyl] | 3.65 | (363.2) |

57 -continued

Structure (Example 72-78):

R-N(pyrrolidinone)-O-N=N(+)(O−)-N(Me)(C(Me)3)

| Example | R | HPLC R_t (min) | MS M + H (or M + Na) |
|---|---|---|---|
| 72 | 3-(isopropyl)phenyl | 3.06 | 349.2 |
| 73 | 6-(trifluoromethyl)pyridin-3-yl | 2.81 | 376.2 (398.0) |
| 74 | 3-(1H-pyrazol-1-yl)phenyl | 3.46 | (395.2) |
| 75 | 4-methylphenyl | 3.48 | (343.2) |
| 76 | 3-fluorophenyl | 2.80 | (347.2) |
| 77 | 3-(1H-1,2,3-triazol-1-yl)phenyl | 2.57 | 374.2 |
| 78 | 5-cyanopyridin-2-yl | 2.71 | 333.2 (355.2) |

Examples 79-86

The following examples were prepared using procedures analogous to those described for EXAMPLE 62, substituting appropriate halides for 1-bromo-4-(trifluoromethyl)benzene in Step A, and sodium 1-(N-tert-butyl-N-ethylamino)diazen-1-ium-1,2-diolate for sodium 1-(N-tert-butyl-N-methylamino)diazen-1-ium-1,2-diolate in Step C. (LC conditions: Ace 3 C18 3.5 μm 3×50 mm column with gradient 10:90-90:10 v/v CH$_3$CN/H$_2$O+v 0.1% TFA over 2.80 min then hold at 90:10 v/v CH$_3$CN/H$_2$O+v 0.1% TFA for 1.2 min; flow rate 1.0 mL/min, UV wavelength 254 nm).

Structure (Example 79-86):

R-N(pyrrolidinone)-O-N=N(+)(O−)-N(Et)(C(Me)3)

| Example | R | HPLC R_t (min) | MS M + H (or M + Na) |
|---|---|---|---|
| 79 | 4-(trifluoromethyl)phenyl | 3.50 | (411.2) |
| 80 | 3-methylphenyl | 3.03 | (357.2) |
| 81 | 5-chloropyridin-3-yl | 2.75 | 356.2 |
| 82 | 3-(1H-pyrazol-1-yl)phenyl | 2.84 | (409.2) |
| 83 | 5-methylpyridin-3-yl | 2.21 | 336.2 |
| 84 | 3,4-dimethylphenyl | 3.02 | (371.2) |
| 85 | 5-(trifluoromethyl)pyridin-3-yl | 2.86 | 390.2 (412.2) |
| 86 | 3-(1H-1,2,3-triazol-1-yl)phenyl | 2.66 | (410.2) |

Example 87

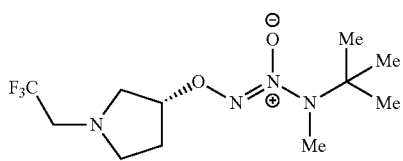 [SMILES: CN(/[N+]([O-])=N/O[C@@H]1CCN(CC(F)(F)F)C1)C(C)(C)C]

O²-[(3R)-1-(2,2,2-trifluoroethyl)pyrrolidin-3-yl]1-(N-tert-butyl-N-methylamino)diazen-1-ium-1,2-diolate The title compound was made by following the procedures described in EXAMPLE 32, substituting O²-[(3R)-pyrolidin-3-yl]1-(N-tert-butyl-N-methylamino)diazen-1-ium-1,2-diolate (EXAMPLE 15) for O²-[(3R)-pyrolidin-3-yl]1-(N-tert-butyl-N-ethylamino)diazen-1-ium-1,2-diolate. $^1$H NMR (500 MHz, CDCl$_3$) δ 4.97-4.92 (m, 1H), 3.25 (dd, J=11.1, 6.1 Hz, 1H), 3.12 (q, J=9.5 Hz, 2H), 2.93-2.83 (m, 3H), 2.81 (s, 3H), 2.23 (dq, J=14.2, 7.7 Hz, 1H), 2.11 (dddd, J=14.1, 7.1, 4.6, 2.5 Hz, 1H), 1.24 (s, 9H); LC-MS: m/z 299.1 (M+H).

Example 88

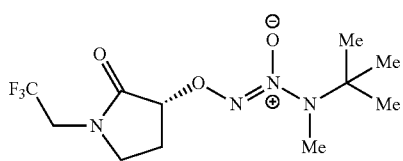 [SMILES: CN(/[N+]([O-])=N/O[C@@H]1CCN(CC(F)(F)F)C1=O)C(C)(C)C]

O²-[(3R)-2-oxo-1-(2,2,2-trifluoroethyl)pyrrolidin-3-yl]1-(N-tert-butyl-N-methylamino)diazen-1-ium-1,2-diolate To a stirring solution of O²-[(3R)-1-(2,2,2-trifluoroethyl)pyrrolidin-3-yl]1-(N-tert-butyl-N-methylamino)diazen-1-ium-1,2-diolate (EXAMPLE 87, 100 mg, 0.34 mmol) in water (225 μL), ethyl acetate (450 μL), and acetonitrile (450 μL) at 0° C. was added ruthenium(IV) oxide (4.5 mg, 0.034 mmol), followed by sodium periodate (215 mg, 1.01 mmol). The reaction mixture was then allowed to warm to room temperature and stirred for 1 hour. The reaction mixture was filtered, and filtrate was concentrated in vacuo to afford the crude product. Chromatography over silica gel, eluting with hexanes/ethyl acetate, afforded the title compound as the less polar regioisomer. $^1$H NMR (500 MHz, CDCl$_3$) δ 5.05 (dd, J=8.6, 7.1 Hz, 1H), 4.13 (dq, J=16.9, 7.6 Hz, 1H), 3.77 (dq, J=15.0, 8.8 Hz, 1H), 3.62 (td, J=9.3, 3.8 Hz, 1H), 3.59-3.52 (m, 1H), 2.84 (s, 3H), 2.65-2.57 (m, 1H), 2.39 (ddt, J=13.8, 8.9, 7.0 Hz, 1H), 1.26 (s, 9H); LC-MS: m/z 313.0 (M+H).

Example 89

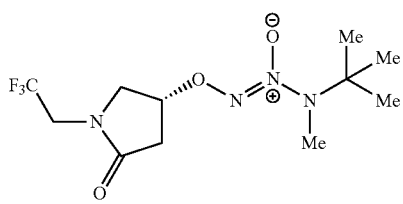 [SMILES: CN(/[N+]([O-])=N/O[C@@H]1CC(=O)N(CC(F)(F)F)C1)C(C)(C)C]

O²-[(3R)-5-oxo-1-(2,2,2-trifluoroethyl)pyrrolidin-3-yl]1-(N-tert-butyl-N-methylamino)diazen-1-ium-1,2-diolate The title compound was made by following the procedures described in Example 88. Chromatography over silica gel, eluting with hexanes/ethyl acetate, afforded the title compound as the more polar regioisomer. $^1$H NMR (500 MHz, CDCl$_3$) δ 5.01-4.96 (m, 1H), 4.05-3.96 (m, 1H), 3.84 (dd, J=11.7, 5.9 Hz, 1H), 3.73-3.60 (m, 2H), 2.78 (dd, J=18.2, 7.1 Hz, 1H), 2.72 (s, 3H), 2.64 (dd, J=18.2, 2.1 Hz, 1H), 1.14 (s, 9H); LC-MS: m/z 313.0 (M+H).

Example 90

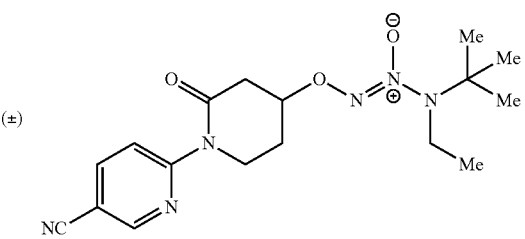 [SMILES: CCN(/[N+]([O-])=N/OC1CCN(c2ccc(C#N)cn2)C(=O)C1)C(C)(C)C]

(±)-O²-[1-(5-cyanopyridin-2-yl)-2-oxopiperidin-1-yl]-(N-tert-butyl-N-ethylamino)diazen-1-ium-1,2-diolate The title compound was made by following the procedures described in EXAMPLE 88, substituting O²-[1-(5-cyanopyridin-2-yl)piperidin-4-yl]1-(N-tert-butyl-N-ethylamino)diazen-1-ium-1,2-diolate (EXAMPLE 48) for O²-[(3R)-1-(2,2,2-trifluoroethyl)pyrrolidin-3-yl]1-(N-tert-butyl-N-methylamino)diazen-1-ium-1,2-diolate. $^1$H NMR (500 MHz, CDCl$_3$) δ 8.70 (d, J=2.2 Hz, 1H), 8.24 (d, J=8.1 Hz, 1H), 7.93 (dd, J=8.8, 2.3 Hz, 1H), 4.91 (qd, J=6.0, 4.4 Hz, 1H), 4.20 (ddd, J=13.5, 7.7, 5.0 Hz, 1H), 4.13 (ddd, J=13.5, 7.0, 5.1 Hz, 1H), 3.18-3.06 (m, 3H), 3.01 (dd, J=17.7, 5.7 Hz, 1H), 2.42-2.30 (m, 2H), 1.27 (s, 9H), 1.08 (t, J=7.0 Hz, 3H); LC-MS: m/z 361.1 (M+H).

Example 91

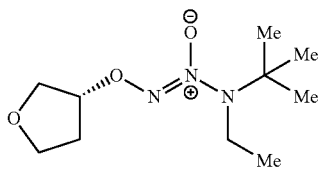 [SMILES: CCN(/[N+]([O-])=N/O[C@@H]1CCOC1)C(C)(C)C]

O²-[(3S)-tetrahydrofuran-3-yl]1-(N-tert-butyl-N-ethylamino)diazen-1-ium-1,2-diolate The title compound was made by following the procedures described in EXAMPLE 3, substituting (3S)-tetrahydrofuran-3-ol for (3S)—N-(tert-butoxycarbonyl)pyrrolidinol. $^1$H NMR (500 MHz, CDCl$_3$) δ 5.06-5.02 (m, 1H), 4.02-3.92 (m, 3H), 3.85 (td, J=8.2, 4.7 Hz, 1H), 3.10 (q, J=7.0 Hz, 2H), 2.27-2.15 (m, 2H), 1.23 (s, 9H), 1.03 (t, J=7.0 Hz, 3H); LC-MS: m/z 254.3 (M+Na).

Example 92

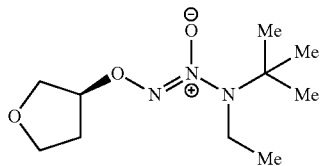 [SMILES: CCN(/[N+]([O-])=N/O[C@H]1CCOC1)C(C)(C)C]

O²-[(3R)-tetrahydrofuran-3-yl]1-(N-tert-butyl-N-ethylamino)diazen-1-ium-1,2-diolate The title compound was made by following the procedures described in EXAMPLE 91, substituting (3R)-tetrahydrofuran-3-ol for (3S)-tetrahydrofuran-3-ol.

Example 93

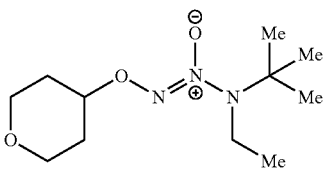 [SMILES: CCN(/[N+]([O-])=N/OC1CCOCC1)C(C)(C)C]

O²-(tetrahydro-2H-pyran-4-yl)1-(N-tert-butyl-N-ethylamino)diazen-1-ium-1,2-diolate The title compound was made by following the procedures described in EXAMPLE 3, substituting tetrahydro-2H-pyran-4-ol for (3S)—N-(tert-butoxycarbonyl)pyrrolidinol. ¹H NMR (500 MHz, CDCl₃) δ 4.54-4.46 (m, 1H), 3.97 (dt, J=11.8, 4.5 Hz, 2H), 3.49 (td, J=10.7, 2.4 Hz, 2H), 3.10 (q, J=7.1 Hz, 2H), 2.08-2.01 (m, 2H), 1.85 (dtd, J=13.1, 9.5, 4.2 Hz, 2H), 1.23 (s, 9H), 1.03 (t, J=7.0 Hz, 3H); LC-MS: m/z 246.1 (M+H).

Example 94

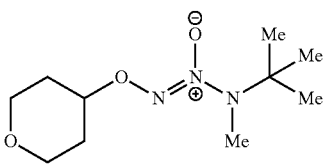 [SMILES: CN(/[N+]([O-])=N/OC1CCOCC1)C(C)(C)C]

O²-(tetrahydro-2H-pyran-4-yl)1-(N-tert-butyl-N-methylamino)diazen-1-ium-1,2-diolate The title compound was made by following the procedures described in EXAMPLE 93, substituting sodium 1-(N-tert-butyl-N-methylamino)diazen-1-ium-1,2-diolate for sodium 1-(N-tert-butyl-N-ethylamino)diazen-1-ium-1,2-diolate. ¹H NMR (500 MHz, CDCl₃) δ 4.47 (tt, J=9.4, 4.2 Hz, 1H), 3.97 (dt, J=11.8, 4.4 Hz, 2H), 3.48 (td, J=10.8, 2.5 Hz, 2H), 2.81 (s, 3H), 2.08-2.00 (m, 2H), 1.89-1.80 (m, 2H), 1.23 (s, 9H); LC-MS: m/z 254.2 (M+Na).

Example 95

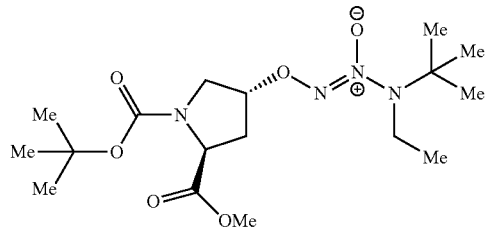 [SMILES: CCN(/[N+]([O-])=N/O[C@@H]1C[C@@H](C(=O)OC)N(C(=O)OC(C)(C)C)C1)C(C)(C)C]

O²-[(3R,5S)-1-(tert-butoxycarbonyl)-5-(methoxycarbonyl)pyrrolidin-3-yl]1-(N-tert-butyl-N-ethylamino)diazen-1-ium-1,2-diolate The title compound was made by following the procedures described in EXAMPLE 3, substituting 1-tert-butyl 2-methyl (2S,4S)-4-hydroxypyrrolidine-1,2-dicarboxylate for (3S)—N-(tert-butoxycarbonyl)pyrrolidinol. ¹H NMR (500 MHz, CDCl₃) δ 5.00 (s br, 1H), 4.49 (t, J=7.9 Hz, D1, 3H), 4.42 (t, J=8.0 Hz, D2, 3H), 3.93-3.81 (m, 1H), 3.79-3.71 (m, 4H), 3.11 (q, J=7.1 Hz, 2H), 2.66-2.56 (m, 1H), 2.29-2.19 (m, 1H), 1.44 (s, D1, 9H), 1.40 (s, D2, 9H), 1.24 (s, D1, 9H), 1.23 (s, D2, 9H), 1.04 (t, J=7.0 Hz, 3H); LC-MS: m/z 411.3 (M+Na).

Example 96

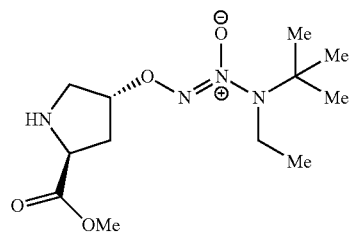 [SMILES: CCN(/[N+]([O-])=N/O[C@H]1CN[C@H](C(=O)OC)C1)C(C)(C)C]

O²-[(3R,5S)-5-(methoxycarbonyl)pyrrolidin-3-yl]1-(N-tert-butyl-N-ethylamino)diazen-1-ium-1,2-diolate To a stirring dichloromethane (11 mL) solution of O²-[(3R,5S)-1-(tert-butoxycarbonyl)-5-(methoxycarbonyl)pyrrolidin-3-yl]1-(N-tert-butyl-N-ethylamino)diazen-1-ium-1,2-diolate (EXAMPLE 95, 2.47 g, 6.36 mmol) was added trifluoroacetic acid (1.72 mL, 22.3 mmol). It was heated to 40° C. for 24 hours. The reaction mixture was purified by reversed phase HPLC to afford the hydrochloride salt of the title compound. ¹H NMR (500 MHz, CDCl₃) δ 8.56 (s br, 2H), 5.17 (s br, 1H), 4.60 (t, J=8.4 Hz, 1H), 3.96 (d, J=12.5 Hz, 1H), 3.81 (s, 3H), 3.66 (d, J=13.2 Hz, 1H), 3.10 (q, J=7.0

Hz, 2H), 2.73 (dd, J=14.5, 6.8 Hz, 1H), 2.58-2.47 (m, 1H), 1.22 (s, 9H), 1.02 (t, J=6.9 Hz, 3H); LC-MS: m/z 289.0 (M+H).

Example 97

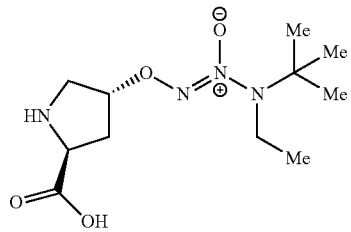 [SMILES: CCN(/[N+]([O-])=N/O[C@H]1CN[C@H](C(=O)O)C1)C(C)(C)C]

$O^2$-[(3R,5S)-5-carboxypyrrolidin-3-yl]1-(N-tert-butyl-N-ethylamino)diazen-1-ium-1,2-diolate To a stirring isopropanol/water (20/80, 0.5 mL) solution of $O^2$-[(3R,5S)-5-(methoxycarbonyl)pyrrolidin-3-yl]1-(N-tert-butyl-N-ethylamino)diazen-1-ium-1,2-diolate (EXAMPLE 96, 200 mg, 0.14 mmol) was added potassium hydroxide (12 mg, 0.21 mmol). After 1.5 hours, the reaction mixture was concentrated in vacuo and purified by reversed phase HPLC to afford the title compound. $^1$H NMR (500 MHz, CD$_3$OD) δ 5.20 (t, J=4.7 Hz, 1H), 4.47 (dd, J=10.4, 7.9 Hz, 1H), 3.71 (dd, J=13.5, 4.5 Hz, 1H), 3.58 (d, J=13.6 Hz, 1H), 3.13 (q, J=7.0 Hz, 2H), 2.70 (dd, J=14.9, 7.9 Hz, 1H), 2.46 (ddd, J=14.9, 10.4, 5.0 Hz, 1H), 1.22 (s, 9H), 1.00 (t, J=7.0 Hz, 3H); LC-MS: m/z 275.0 (M+H).

Example 98

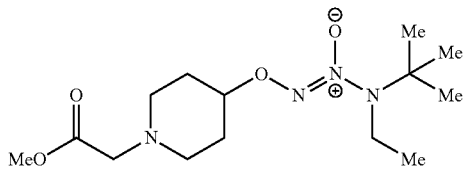 [SMILES: CCN(/[N+]([O-])=N/OC1CCN(CC(=O)OC)CC1)C(C)(C)C]

$O^2$-[1-(2-methoxy-2-oxoethyl)piperidin-4-yl]1-(N-tert-butyl-N-ethylamino)diazen-1-ium-1,2-diolate To a N,N-dimethylformamide solution of the hydrochloride salt of $O^2$-(piperidin-4-yl)1-(N-tert-butyl-N-ethylamino)diazen-1-ium-1,2-diolate (EXAMPLE 17, 1.0 g, 3.6 mmol) and triethylamine (2.0 mL, 14 mmol) was added methyl bromoacetate (1.09 g, 7.02 mmol). The reaction mixture was stirred at room temperature and after 16 hours, the reaction mixture was diluted with ethyl acetate (50 mL) and washed with 1 N hydrochloric acid (20 mL). The organic layer was dried (magnesium sulfate), filtered and concentrated in vacuo to afford the crude product. Chromatography over silica gel, eluting with hexanes/ethyl acetate, afforded the title compound. $^1$H NMR (500 MHz, CDCl$_3$) δ 4.36 (tt, J=8.5, 3.9 Hz, 1H), 3.71 (s, 3H), 3.22 (s, 2H), 3.09 (q, J=7.0 Hz, 2H), 2.82-2.76 (m, 2H), 2.48-2.42 (m, 2H), 2.07-2.02 (m, 2H), 1.97-1.88 (m, 2H), 1.22 (s, 9H), 1.02 (t, J=7.0 Hz, 3H); LC-MS: m/z 317.3 (M+H).

Example 99

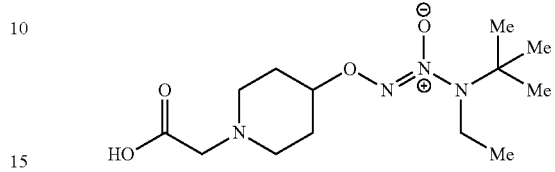

$O^2$-[1-(carboxymethyl)piperidin-4-yl]1-(N-tert-butyl-N-ethylamino)diazen-1-ium-1,2-diolate The title compound was made by following the procedures described in EXAMPLE 97, substituting $O^2$-[1-(2-methoxy-2-oxoethyl)piperidin-4-yl]1-(N-tert-butyl-N-ethylamino)diazen-1-ium-1,2-diolate (EXAMPLE 98) for $O^2$-[(3R,5S)-5-(methoxycarbonyl)pyrrolidin-3-yl]1-(N-tert-butyl-N-ethylamino)diazen-1-ium-1,2-diolate (EXAMPLE 96). $^1$H NMR (500 MHz, CDCl$_3$) δ 4.70 (br s, 1H), 3.91 (br s, 2H), 3.68 (br s, 2H), 3.22 (br s, 2H), 3.12 (q, J=7.1 Hz, 2H), 2.45 (br s, 2H), 2.31-2.21 (m, 2H), 1.24 (s, 9H), 1.03 (t, J=7.0 Hz, 3H); LC-MS: m/z 303.4 (M+H).

Example 100

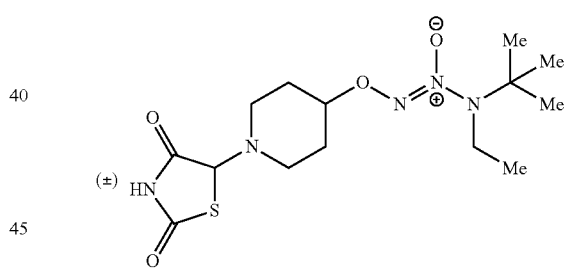

(±)-$O^2$-[1-(2,4-dioxo-1,3-thiazolidin-5-yl)piperidin-4-yl]1-(N-tert-butyl-N-ethylamino)diazen-1-ium-1,2-diolate Step A: (±)-5-bromothiazolidine-2,4-dione To an acetic acid (25 mL) solution of thiazolidine-2,4-dione (10.0 g, 85.4 mmol) at 85° C. was added bromine (4.4 mL, 85 mmol) dropwise over 1 hour. The reaction mixture was stirred at 85° C. for an additional hour. The solution was cooled to room temperature and poured into water (100 mL). The crude product was extracted into ether (100 mL), dried (magnesium sulfate), filtered and concentrated in vacuo. Chromatography over silica gel, eluting with chloroform/acetonitrile, afforded the title compound as an oil, which on trituration with hexane turned into a white solid. $^1$H NMR (500 MHz, d$_6$-acetone) δ 11.3 (br s, 1H), 6.40 (s, 1H).

Step B: (±)-O²-[1-(2,4-dioxo-1,3-thiazolidin-5-yl)piperidin-4-yl]1-(N-tert-butyl-N-ethylamino)diazen-1-ium-1,2-diolate The title compound was made by following the procedures described in EXAMPLE 98, substituting (±)-5-bromothiazolidine-2,4-dione for methyl bromoacetate. ¹H NMR (500 MHz, CDCl₃) δ5.68 (s, 1H), 4.38 (tt, J=8.1, 3.8 Hz, 1H), 3.10 (q, J=7.0 Hz, 2H), 2.95-2.90 (m, 1H), 2.74-2.69 (m, 1H), 2.67-2.59 (m, 1H), 2.44-2.37 (m, 1H), 2.13-1.90 (m, 4H), 1.23 (s, 9H), 1.02 (t, J=7.0 Hz, 3H); LC-MS: m/z 360.3 (M+H).

Example 101

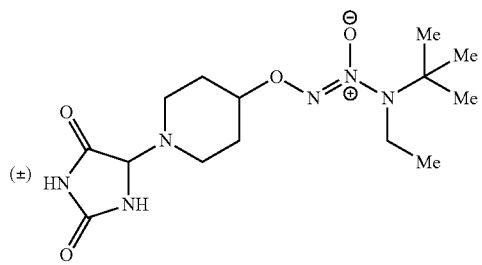 [SMILES: CCN(/[N+]([O-])=N/OC1CCN(C2NC(=O)NC2=O)CC1)C(C)(C)C]

O²-[1-(2,5-dioxoimidazolidin-4-yl)piperidin-4-yl]1-(N-tert-butyl-N-ethylamino)diazen-1-ium-1,2-diolate The title compound was made by following the procedures described in EXAMPLE 100, substituting imidazolidine-2,4-dione for thiazolidine-2,4-dione in step A. ¹H NMR (500 MHz, d₆-DMSO) δ 11.05 (s, 1H), 8.48 (s, 1H), 4.97 (s, 1H), 4.36 (br s, 1H), 3.03-2.97 (m, 3H), 2.78 (br s, 2H), 2.63-2.51 (m, 1H), 1.99 (br s, 2H), 1.73 (br s, 2H), 1.11 (s, 9H), 0.86 (t, J=6.9 Hz, 3H); LC-MS: m/z 343.3 (M+H).

Example 102

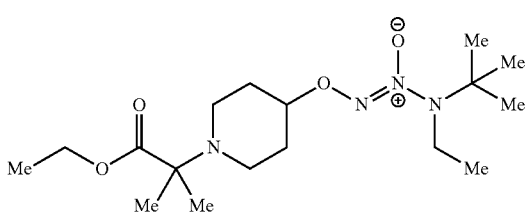 [SMILES: CCOC(=O)C(C)(C)N1CCC(O/N=[N+](\[O-])N(CC)C(C)(C)C)CC1]

O²-[1-(1-ethoxy-2-methyl-1-oxopropan-2-yl)piperidin-4-yl]1-(N-tert-butyl-N-ethylamino)diazen-1-ium-1,2-diolate The title compound was made by following the procedures described in EXAMPLE 98, substituting ethyl 2-bromoisobutyrate for methyl bromoacetate. ¹H NMR (500 MHz, CDCl₃) δ 4.31 (br s, 1H), 4.16 (q, J=7.1 Hz, 2H), 3.09 (q, J=7.0 Hz, 2H), 2.89 (br s, 2H), 2.36 (br s, 2H), 2.04 (br s, 2H), 1.84 (br s, 2H), 1.35-1.15 (m, 16H), 1.02 (t, J=7.0 Hz, 3H); LC-MS: m/z 359.4 (M+H).

Example 103

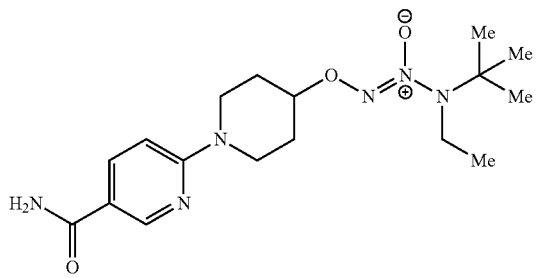 [SMILES: CCN(/[N+]([O-])=N/OC1CCN(c2ccc(C(N)=O)cn2)CC1)C(C)(C)C]

O²-[1-(5-carbamoylpyridin-2-yl)piperidin-4-yl]1-(N-tert-butyl-N-ethylamino diazen-1-ium-1,2-diolate A mixture of O²-[1-(5-cyanopyridin-2-yl)piperidin-4-yl]1-(N-tert-butyl-N-ethylamino)diazen-1-ium-1,2-diolate (EXAMPLE 48, 591 mg, 1.71 mmol) and sodium perborate tetrahydrate (1050 mg, 6.82 mmol) in water (5 mL)/methanol (5 mL) was heated at 50° C. for 16 hours. The reaction mixture was cooled, acidified with 1 N hydrochloric acid, and purified by reversed phase HPLC to afford the title compound. ¹H NMR (500 MHz, CDCl₃) δ 8.87 (d, J=2.2 Hz, 1H), 8.37 (dd, J=9.5, 2.1 Hz, 1H), 6.99 (d, J=9.5 Hz, 1H), 4.75-4.67 (m, 1H), 4.04-3.97 (m, 2H), 3.88-3.81 (m, 2H), 3.96-3.36 (m, 2H), 3.12 (q, J=7.0 Hz, 2H), 2.21-2.13 (m, 4H), 1.24 (s, 9H), 1.04 (t, J=6.9 Hz, 3H); LC-MS: m/z 365.1 (M+H).

Example 104

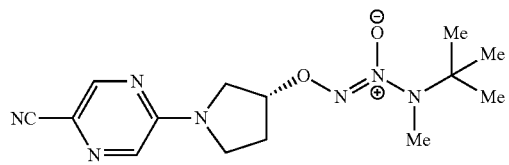 [SMILES: CN(/[N+]([O-])=N/O[C@@H]1CCN(c2cnc(C#N)cn2)C1)C(C)(C)C]

O²-[(3R)-1-(5-cyanopyrazin-2-yl)pyrrolidin-3-yl]1-(N-tert-butyl-N-methylamino)diazen-1-ium-1,2-diolate To a N,N-dimethylformamide (10 mL) solution of O²-[(3R)-pyrrolidin-3-yl]1-(N-tert-butyl-N-methylamino)diazen-1-ium-1,2-diolate (EXAMPLE 15, 500 mg, 1.98 mmol) was added cesium carbonate (1930 mg, 5.93 mmol) and 5-bromopyrazine-2-carbonitrile (400 mg, 2.18 mmol). The reaction mixture was stirred at room temperature for 24 hours. It was then diluted with ethyl acetate (100 mL), and washed with water (2×50 mL) and brine (50 mL). The combined organic layers were dried (magnesium sulfate), filtered, and concentrated in vacuo. Chromatography over silica gel, eluting with hexanes/ethyl acetate, afforded the title compound. ¹H NMR (500 MHz, CDCl₃) δ 8.34 (s, 1H), 7.89 (s, 1H), 5.14 (br s, 1H), 3.99 (br s, 1H), 3.82-3.67 (m, 3H), 2.80 (s, 3H), 2.55 (br s, 1H), 2.32 (br s, 1H), 1.22 (s, 9H); LC-MS: m/z 320.3 (M+H).

Example 105

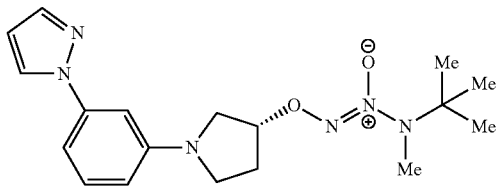 [SMILES: CN(/[N+]([O-])=N/O[C@@H]1CCN(c2cccc(-n3cccn3)c2)C1)C(C)(C)C]

O²-{(3R)-1-[3-(1H-pyrazol-1-yl)phenyl]pyrrolidin-3-yl}1-(N-tert-butyl-N-methylamino)diazen-1-ium-1,2-diolate The title compound was made by following the procedures described in EXAMPLE 38, substituting 1-(3-bromophenyl)-1H-pyrazole for 3-bromobenzonitrile. ¹H NMR (500 MHz, CDCl₃) δ 7.8-6.4 (m, 7H), 5.15-5.09 (m, 1H), 3.75-3.40 (m, 4H), 2.81 (s, 3H), 2.50-2.20 (m, 2H), 1.23 (s, 9H); LC-MS: m/z 359.2 (M+H).

Example 106

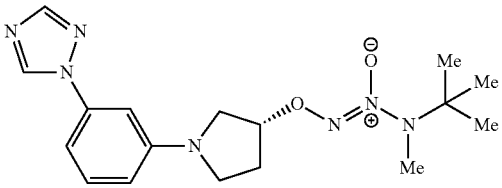 [SMILES: CN(/[N+]([O-])=N/O[C@@H]1CCN(c2cccc(-n3cncn3)c2)C1)C(C)(C)C]

O²-{(3R)-1-[3-(1H-1,2,4-triazol-1-yl)phenyl]pyrrolidin-3-yl}1-(N-tert-butyl-N-methylamino)diazen-1-ium-1,2-diolate The title compound was made by following the procedures described in EXAMPLE 38, substituting 1-(3-bromophenyl)-1H-1,2,4-triazole for 3-bromobenzonitrile. ¹H NMR (500 MHz, CDCl₃) δ 8.5-6.5 (m, 6H), 5.12 (br s, 1H), 3.75-3.40 (m, 4H), 2.81 (s, 3H), 2.50-2.20 (m, 2H), 1.28 (s, 9H); LC-MS: m/z 360.2 (M+H).

Example 107

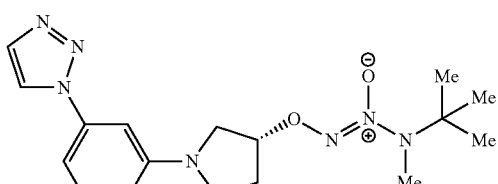

O²-{(3R)-1-[3-(1H-1,2,3-triazol-1-yl)phenyl]pyrrolidin-3-yl}1-(N-tert-butyl-N-methylamino)diazen-1-ium-1,2-diolate The title compound was made by following the procedures described in EXAMPLE 38, substituting 1-(3-bromophenyl)-1H-1,2,3-triazole for 3-bromobenzonitrile. ¹H NMR (500 MHz, CDCl₃) δ 8.0-6.6 (m, 6H), 5.16 (br s, 1H), 3.75-3.40 (m, 4H), 2.84 (s, 3H), 2.50-2.20 (m, 2H), 1.26 (s, 9H); LC-MS: m/z 382.3 (M+Na).

Example 108

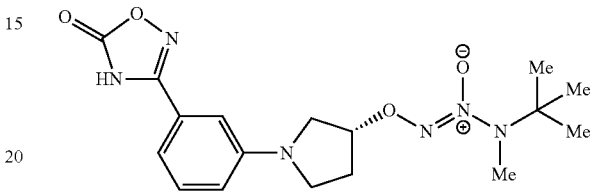

O²-{(3R)-1-[3-(5-oxo-4,5-dihydro-1,2,4-oxadiazol-3-yl)phenyl]pyrrolidin-3-yl}1-(N-tert-butyl-N-methylamino)diazen-1-ium-1,2-diolate To an ethanolic (2 mL) solution of O²-[(3R)-1-(3-cyanophenyl)pyrrolidin-3-yl]1-(N-tert-butyl-N-methylamino)diazen-1-ium-1,2-diolate (EXAMPLE 38, 285 mg, 0.898 mmol) was added triethylamine (0.30 mL, 2.2 mmol) and hydroxylamine hydrochloride (100 mg, 1.44 mmol). The reaction mixture was heated to 80° C. for 2 hours. It was cooled, concentrated in vacuo, redissolved in ethyl acetate, washed with water, dried (potassium carbonate), and concentrated in vacuo again. This crude material was redissolved in acetonitrile (2 mL), and carbonyldiimidazole (180 mg, 1.11 mmol) was added. The reaction mixture was heated to 60° C. for 1.5 hour. It was cooled and concentrated in vacuo. Chromatography over silica gel, eluting with hexanes/ethyl acetate, afforded the title compound. ¹H NMR (500 MHz, CDCl₃) δ 7.3-6.6 (min, 4H), 5.19 (br s, 1H), 3.65-3.35 (m, 4H), 2.88 (s, 3H), 2.5-2.2 (m, 2H), 1.28 (s, 9H); LC-MS: m/z 376.8 (M+H).

Example 109

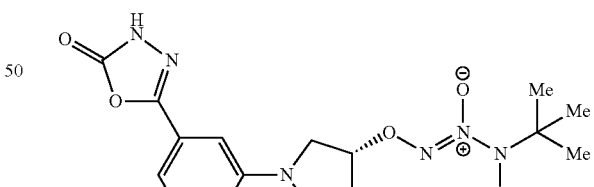

O²-{(3R)-1-[3-(5-oxo-4,5-dihydro-1,3,4-oxadiazol-2-yl)phenyl]pyrrolidin-3-yl}1-(N-tert-butyl-N-methylamino)diazen-1-ium-1,2-diolate Step A: O²-{(3R)-1-[3-(ethoxycarbonyl)phenyl]pyrrolidin-3-yl}1-(N-tert-butyl-N-methylamino)diazen-1-ium-1,2-diolate The title compound was made by following the procedures described in EXAMPLE 38, substituting ethyl 3-bromobenzoate for 3-bromobenzonitrile. ¹H NMR (500 MHz, CDCl₃) δ 7.40-7.24 (m, 3H), 6.73 (dd, J=8.2, 1.3 Hz, 1H), 5.14 (br s, 1H), 4.38 (q, J=7.1 Hz, 2H), 3.72-3.45 (m, 4H), 2.83 (s, 3H), 2.50-2.20 (m, 2H), 1.40 (t, J=7.2 Hz, 3H), 1.25 (s, 9H); LC-MS: m/z 387.2 (M+Na).

Step B: O²-{(3R)-1-[3-(5-oxo-4,5-dihydro-1,3,4-oxadiazol-2-yl)phenyl]pyrrolidin-3-yl}1-(N-tert-butyl-N-methylamino)diazen-1-ium-1,2-diolate The title compound was made by following the procedures described in EXAMPLE 108, substituting hydrazine for triethylamine and hydroxylamine hydrochloride. ¹H NMR (500 MHz, CDCl₃) δ 7.3-6.6 (m, 4H), 5.22 (br s, 1H), 3.8-3.4 (m, 4H), 2.87 (s, 3H), 2.5-2.2 (m, 2H), 1.28 (s, 9H); LC-MS: m/z 377.2 (M+H).

Example 110

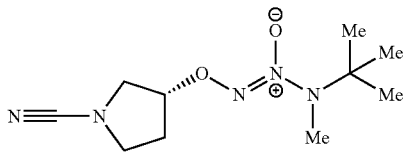 [SMILES: CN(/[N+]([O-])=N/O[C@@H]1CCN(C#N)C1)C(C)(C)C]

O²-[(3R)-1-cyanopyrrolidin-3-yl]1-(N-tert-butyl-N-methylamino)diazen-1-ium-1,2-diolate To an ethanol (22 mL) suspension of the hydrochloride salt of O²-[(3R)-pyrrolidin-3-yl]1-(N-tert-butyl-N-methylamino)diazen-1-ium-1,2-diolate (EXAMPLE 15, 1.70 g, 6.73 mmol) and sodium bicarbonate (3.60 g, 42.9 mmol) was added a 5.0 M acetonitrile solution of cyanogen bromide (2.69 mL, 13.5 mmol). The reaction mixture was stirred at room temperature for 3 hours, after which it was concentrated in vacuo. The residue was redissolved in dichloromethane, filtered and concentrated in vacuo. Chromatography over silica gel, eluting with hexanes/ethyl acetate, afforded the title compound. ¹H NMR (500 MHz, CDCl₃) δ 4.98-4.93 (m, 1H), 3.71-3.59 (m, 3H), 3.55 (td, J=9.1, 2.5 Hz, 1H), 2.82 (s, 3H), 2.38-2.30 (m, 1H), 2.21-2.11 (m, 1H), 1.24 (s, 9H); LC-MS: m/z 264.3 (M+Na).

Example 111

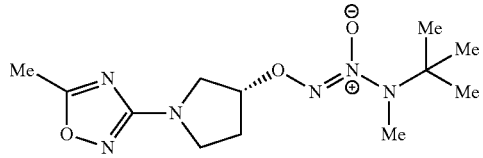 [SMILES: Cc1nc(N2CC[C@@H](O/N=[N+](\[O-])N(C)C(C)(C)C)C2)no1]

O²-[(3R)-1-(5-methyl-1,2,4-oxadiazol-3-yl)pyrrolidin-3-yl]1-(N-tert-butyl-N-methylamino)diazen-1-ium-1,2-diolate To an ethanol (6 mL) solution of O²-[(3R)-1-cyanopyrrolidin-3-yl]1-(N-tert-butyl-N-methylamino)diazen-1-ium-1,2-diolate (EXAMPLE 110, 700 mg, 2.90 mmol) and triethylamine (1.01 mL, 7.25 mmol) was added hydroxylamine hydrochloride (222 mg, 3.19 mmol). The reaction mixture was heated to 80° C. for 1 hour. It was then cooled to room temperature and concentrated in vacuo. The crude residue was dissolved in pyridine (4.0 mL, 50 mmol), and acetic anhydride (0.328 mL, 3.48 mmol) was added to the reaction mixture. It was heated to 80° C. for 2 hours. The reaction mixture was cooled and purified by reversed phase HPLC to afford the title compound. ¹H NMR (500 MHz, CDCl₃) δ 5.11-5.05 (m, 1H), 3.77 (d, J=12.3 Hz, 1H), 3.71 (dd, J=12.3, 4.7 Hz, 1H), 3.62 (d, J=9.4 Hz, 1H), 3.61 (dd, J=9.5, 1.2 Hz, 1H), 2.81 (s, 3H), 2.46 (s, 3H), 2.47-2.37 (m, 1H), 2.30-2.20 (m, 1H), 1.23 (s, 9H); LC-MS: m/z 321.3 (M+H).

Example 112

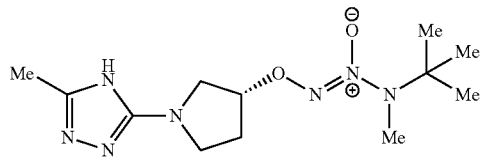 [SMILES: Cc1nnc(N2CC[C@@H](O/N=[N+](\[O-])N(C)C(C)(C)C)C2)[nH]1]

O²-[(3R)-1-(5-methyl-4H-1,2,4-triazol-3-yl)pyrrolidin-3-yl]1-(N-tert-butyl-N-methylamino)diazen-1-ium-1,2-diolate The title compound was made by following the procedures described in EXAMPLE 111, substituting hydrazine for hydroxylamine hydrochloride. ¹H NMR (500 MHz, CDCl₃) δ): 5.22-5.13 (m, 1H), 3.90 (d, J=12.3 Hz, 1H), 3.84 (dd, J=12.4, 4.2 Hz, 1H), 3.75 (t, J=9.5 Hz, 1H), 3.63 (td, J=10.3, 6.8 Hz, 1H), 2.84 (s, 3H), 2.52 (dd, J=14.3, 6.5 Hz, 1H), 2.45-2.22 (m, 4H), 1.25 (s, 9H); LC-MS: m/z 298.0 (M+H).

Example 113

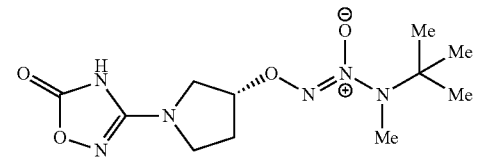 [SMILES: CN(/[N+]([O-])=N/O[C@@H]1CCN(c2noc(=O)[nH]2)C1)C(C)(C)C]

O²-[(3R)-1-(5-oxo-4,5-dihydro-1,2,4-oxadiazol-3-yl)pyrrolidin-3-yl]1-(N-tert-butyl-N-methylamino)diazen-1-ium-1,2-diolate The title compound was made by following the procedures described in EXAMPLE 108, substituting O²-[(3R)-1-cyanopyrrolidin-3-yl]1-(N-tert-butyl-N-methylamino)diazen-1-ium-1,2-diolate (EXAMPLE 110) for O²-[(3R)-1-(3-cyanophenyl)pyrrolidin-3-yl]1-(N-tert-butyl-N-methylamino)diazen-1-ium-1,2-diolate. ¹H NMR (500 MHz, CDCl₃) δ 5.14-5.07 (m, 1H), 3.72 (d, J=12.0 Hz, 1H), 3.66 (dd, J=12.1, 4.5 Hz, 1H), 3.64-3.52 (m, 2H), 2.84 (s, 3H), 2.51-2.44 (m, 1H), 2.34-2.24 (m, 1H), 1.26 (s, 9H); LC-MS: m/z 301.3 (M+H).

Example 114

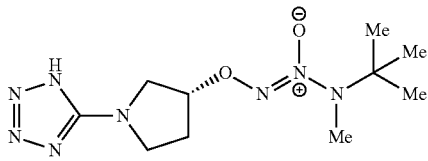 [SMILES: CN(/[N+]([O-])=N/O[C@@H]1CCN(c2nnn[nH]2)C1)C(C)(C)C]

$O^2$-[(3R)-1-(1H-tetrazol-5-yl)pyrrolidin-3-yl]1-(N-tert-butyl-N-methylamino)diazen-1-ium-1,2-diolate To a toluene (8 mL) solution of $O^2$-[(3R)-1-cyanopyrrolidin-3-yl]1-(N-tert-butyl-N-methylamino)diazen-1-ium-1,2-diolate (EXAMPLE 110, 700 mg, 2.90 mmol) and trimethylsilyl azide (0.78 mL, 5.8 mmol) was added dibutyltin oxide (100 mg, 0.40 mmol). The reaction mixture was heated to 80° C. for 6 hours. The reaction mixture was cooled and purified by reversed phase HPLC to afford the title compound. $^1$H NMR (500 MHz, CDCl$_3$) δ 8.8 (br s, 1H), 5.20-5.16 (m, 1H), 3.89-3.80 (m, 2H), 3.69 (td, J=9.3, 2.2 Hz, 1H), 3.62 (td, J=9.8, 6.8 Hz, 1H), 2.86 (s, 3H), 2.48 (dd, J=14.3, 6.6 Hz, 1H), 2.38-2.28 (m, 1H), 1.27 (s, 9H); LC-MS: m/z 285.1 (M+H).

Example 115

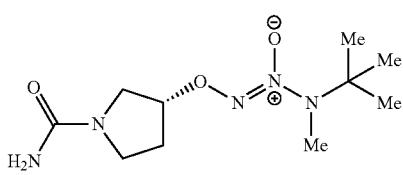

$O^2$-[(3R)-1-carbamoylpyrrolidin-3-yl]1-(N-tert-butyl-N-methylamino)diazen-1-ium-1,2-diolate To a dichloromethane (20 mL) solution of the hydrochloride salt of $O^2$-[(3R)-pyrrolidin-3-yl]1-(N-tert-butyl-N-methylamino)diazen-1-ium-1,2-diolate (EXAMPLE 15, 1.00 g, 3.96 mmol) and triethylamine (1.11 mL, 7.96 mmol) at 0° C. was added chlorosulfonyl isocyanate (0.515 mL, 5.93 mmol). The reaction mixture was stirred for 2 hours, after which the reaction mixture was warmed to room temperature and quenched with water (11 mL). It was concentrated in vacuo, diluted with water (20 mL), and extracted with ethyl acetate (4×50 mL). The combined organic extracts were dried (magnesium sulfate), filtered and concentrated in vacuo. The crude residue was purified by reversed phase HPLC to afford the title compound. $^1$H NMR (500 MHz, CDCl$_3$) δ 5.74 (s, 2H), 5.06-4.95 (m, 1H), 3.86-3.74 (m, 1H), 3.64 (dd, J=12.5, 4.6 Hz, 1H), 3.60-3.50 (m, 2H), 2.82 (s, 3H), 2.48-2.38 (m, 1H), 2.29-2.19 (m, 1H), 1.23 (s, 9H); LC-MS: m/z 260.3 (M+H).

Example 116

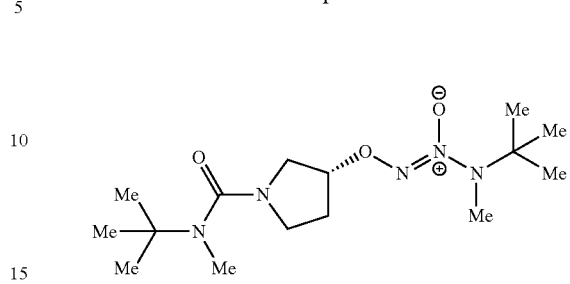

$O^2$-{(3R)-1-[tert-butyl(methyl)carbamoyl]pyrrolidin-3-yl}1-(N-tert-butyl-N-methylamino)diazen-1-ium-1,2-diolate To a chloroform (2 mL) solution of N-methyl-tert-butylamine (26.0 μL, 0.22 mmol) and triethylamine (110 μL, 0.79 mmol) at 0° C. was added triphosgene (22 mg, 0.073 mmol). The reaction mixture was stirred at 0° C. for 10 minutes, then at room temperature for 1 hour. To this reaction mixture was added triethylamine (110 μl, 0.79 mmol), followed by the hydrochloride salt of $O^2$-[(3R)-pyrrolidin-3-yl]1-(N-tert-butyl-N-methylamino)diazen-1-ium-1,2-diolate (EXAMPLE 15, 50 mg, 0.198 mmol). After being stirred for 1 hour at room temperature, the reaction mixture was concentrated in vacuo. Chromatography over silica gel, eluting with hexanes/ethyl acetate, afforded the title compound. $^1$H NMR (500 MHz, CDCl$_3$) δ 4.96-4.93 (m, 1H), 3.76 (dd, J=12.8, 5.1 Hz, 1H), 3.58-3.50 (m, 2H), 3.46 (ddd, J=10.5, 8.6, 3.1 Hz, 1H), 2.81 (s, 3H), 2.73 (s, 3H), 2.28-2.21 (m, 1H), 2.15-2.04 (m, 1H), 1.30 (s, 9H), 1.24 (s, 9H); LC-MS: m/z 330.4 (M+H).

Example 117

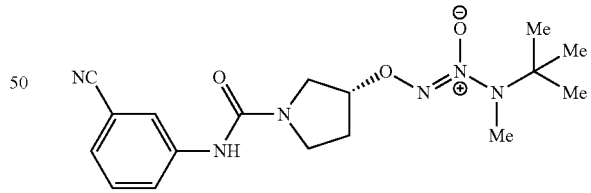

$O^2$-{(3R)-1-[(3-cyanophenyl)carbamoyl]pyrrolidin-3-yl}1-(N-tert-butyl-N-methylamino)diazen-1-ium-1,2-diolate The title compound was made by following the procedures described in EXAMPLE 58, substituting 3-cyanophenyl isocyanate for tert-butyl isocyanate. $^1$H NMR (500 MHz, CDCl$_3$) δ 7.81 (s, 1H), 7.65 (dd, J=8.4, 1.2 Hz, 1H), 7.40 (t, J=7.9 Hz, 1H), 7.33 (d, J=7.7 Hz, 1H), 6.38 (br s, 1H), 5.08-5.06 (m, 1H), 3.90 (d, J=12.3 Hz, 1H), 3.76 (dd, J=12.3, 4.5

Hz, 1H), 3.69-3.66 (m, 2H), 2.85 (s, 3H), 2.49-2.45 (m, 1H), 2.34-2.26 (m, 1H), 1.27 (s, 9H); LC-MS: m/z 361 (M+H).

Example 118

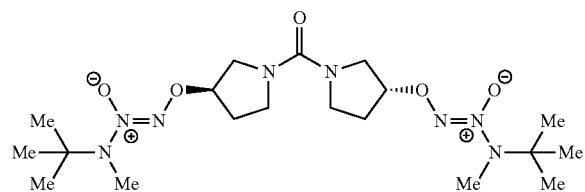 [SMILES: CN(/[N+]([O-])=N/O[C@@H]1CCN(C(=O)N2CC[C@@H](O/N=[N+](\[O-])N(C)C(C)(C)C)C2)C1)C(C)(C)C]

1,1'-carbonylbis{O$^2$-[(3R-pyrrolidin-3-yl]1-(N-tert-butyl-N-methylamino)diazen-1-ium-1,2-diolate}

To a dichloromethane (2 mL) solution of the hydrochloride salt of O$^2$-[(3R)-pyrrolidin-3-yl]1-(N-tert-butyl-N-methylamino)diazen-1-ium-1,2-diolate (EXAMPLE 15, 50 mg, 0.20 mmol) and triethylamine (110 µL, 0.79 mmol) at 0° C. was added a 20% toluene solution of phosgene (208 µL, 0.396 mmol). The reaction mixture was warmed up to room temperature and stirred for 1 hour. It was concentrated in vacuo and redissolved in tetrahydrofuran (10 mL). More hydrochloride salt of O$^2$-[(3R)-pyrrolidin-3-yl]1-(N-tert-butyl-N-methylamino)diazen-1-ium-1,2-diolate (EXAMPLE 15, 50 mg, 0.20 mmol) and triethylamine (110 µl, 0.79 mmol) were added. The reaction mixture was stirred for another 2 hours and concentrated in vacuo. The crude residue was purified by reversed phase HPLC to afford the title compound. $^1$H NMR (500 MHz, CDCl$_3$) δ 4.99-4.96 (m, 2H), 3.85 (dd, J=12.8, 4.5 Hz, 2H), 3.71-3.62 (m, 4H), 3.58 (td, J=9.4, 1.7 Hz, 2H), 2.83 (s, 6H), 2.33 (dd, J=14.0, 6.2 Hz, 2H), 2.15-2.05 (m, 2H), 1.25 (s, 18H); LC-MS: m/z 459.3 (M+H).

Example 119

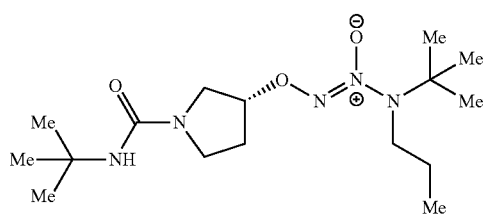 [SMILES: CCCN(/[N+]([O-])=N/O[C@@H]1CCN(C(=O)NC(C)(C)C)C1)C(C)(C)C]

O$^2$-[(3R)-1-(tert-butylcarbamoyl)pyrrolidin-3-yl]1-(N-tert-butyl-N-propylamino)diazen-1-ium-1,2-diolate Step A: (S)—N-(tert-butyl)-3-hydroxypyrrolidine-1-carboxamide To a dichloromethane (100 mL)/diethyl ether (200 mL) solution of (S)-pyrrolidin-3-ol (9.80 mL, 121 mmol) and triethylamine (21.9 mL, 157 mmol) at 0° C. was added tert-butyl isocyanate (13.8 mL, 121 mmol). The reaction mixture was stirred for 30 minutes and concentrated in vacuo to afford the title compound. $^1$H NMR (500 MHz, CDCl$_3$) δ 4.54-4.38 (m, 1H), 4.10 (br s, 1H), 3.48-3.32 (m, 5H), 2.06-1.95 (m, 2H), 1.35 (s, 9H); LC-MS: m/z 187.3 (M+H).

Step B: O$^2$-[(3R)-1-(tert-butylcarbamoyl)pyrrolidi-3-yl]1-(N-tert-butyl-N-propylamino)diazen-1-ium-1,2-diolate The title compound was made by following the procedures described in EXAMPLE 1, substituting (S)—N-(tert-butyl)-3-hydroxypyrrolidine-1-carboxamide for (3S)—N-(tert-butoxycarbonyl)pyrrolidinol in step A, and sodium 1-(N-tert-butyl-N-propylamino)diazen-1-ium-1,2-diolate for sodium 1-(N-tert-butyl-N-methylamino)diazen-1-ium-1,2-diolate in step B. $^1$H NMR (500 MHz, CDCl$_3$) δ 4.98-4.94 (m, 1H), 4.01 (br s, 1H), 3.65-3.59 (m, 1H) 3.59 (dd, J=12.1, 4.5 Hz, 1H), 3.45 (d, J=9.5 Hz, 1H), 3.44 (d, J=9.5 Hz, 1H), 2.97 (dd, J=8.4, 6.3 Hz, 2H), 2.35-2.22 (m, 1H), 2.20-2.10 (m, 1H), 1.40-1.30 (m, 11H), 1.20 (s, 9H), 0.91 (t, J=7.4 Hz, 3H); LC-MS: m/z 344.4 (M+H).

Example 120

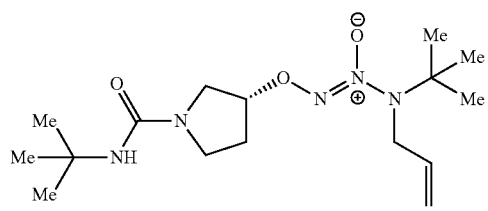 [SMILES: C=CCN(/[N+]([O-])=N/O[C@@H]1CCN(C(=O)NC(C)(C)C)C1)C(C)(C)C]

O$^2$-[(3R)-1-(tert-butylcarbamoyl)pyrrolidin-3-yl]-(N-tert-butyl-N-allylamino)diazen-1-ium-1,2-diolate The title compound was made by following the procedures described in EXAMPLE 8, substituting N-tert-butyl-N-allylamine for N-tert-butyl-N-propylamine in step A and (S)—N-(tert-butyl)-3-hydroxypyrrolidine-1-carboxamide (EXAMPLE 119, STEP A) for N-(tert-butoxycarbonyl)-4-hydroxypiperidine in step B. $^1$H NMR (500 MHz, CDCl$_3$) δ 5.78 (ddt, J=17.1, 10.0, 6.7 Hz, 1H), 5.27 (dd, J=17.1, 1.6 Hz, 1H), 5.17 (d, J=10.1 Hz, 1H), 4.98-4.94 (m, 1H), 4.01 (br s, 1H), 3.65-3.54 (m, 4H), 3.43-3.38 (m, 2H), 2.32-2.26 (m, 1H), 2.18-2.07 (m, 1H), 1.34 (s, 9H), 1.26 (s, 9H); LC-MS: m/z 342.2 (M+H).

Example 121

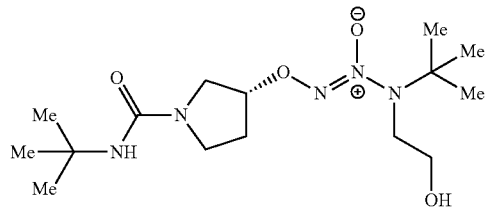 [SMILES: CC(C)(C)NC(=O)N1CC[C@@H](O/N=[N+](\[O-])N(CCO)C(C)(C)C)C1]

O$^2$-[(3R)-1-(tert-butylcarbamoyl)pyrrolidin-3-yl]1-[N-tert-butyl-N-(2'-hydroxyethyl)amino]diazen-1-ium-1,2-diolate The title compound was made by following the procedures described in EXAMPLE 120, substituting N-tert-butyl-N-(2'- hydroxyethyl)amine for N-tert-butyl-N-propylamine. $^1$H NMR (500 MHz, CDCl$_3$) δ 4.96 (tt, J=4.7, 1.7 Hz, 1H), 4.03 (br s, 1H), 3.70 (d, J=12.3 Hz, 1H), 3.58-3.50 (m, 3H), 3.42 (d, J=9.5 Hz, 1H), 3.41 (d, J=9.5 Hz, 1H), 3.22 (t, J=5.1 Hz, 2H), 2.48 (t, J=5.6 Hz, 1H), 2.33-2.27 (m, 1H), 2.16 (dtd, J=14.0, 9.5, 4.8 Hz, 1H), 1.32 (s, 9H), 1.23 (s, 9H); LC-MS: m/z 346.4 (M+H).

Example 122

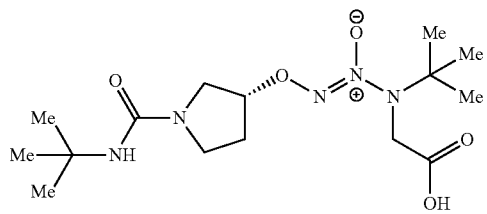 [SMILES: CC(C)(C)NC(=O)N1CC[C@@H](O/N=[N+](\[O-])N(CC(=O)O)C(C)(C)C)C1]

O$^2$-[(3R-1-(tert-butylcarbamoyl)pyrrolidin-3-yl]1-[N-tert-butyl-N-(carboxymethyl)amino]diazen-1-ium-1,2-diolate To an acetone (3 mL) solution of O$^2$-[(3R)-1-(tert-butylcarbamoyl)pyrrolidin-3-yl]1-[N-tert-butyl-N-(2'-hydroxyethyl)amino]diazen-1-ium-1,2-diolate (EXAMPLE 121, 100 mg, 0.29 mmol) at room temperature was added dropwise a 2.5 M dilute sulfuric acid solution of chromium(VI) oxide (0.12 mL, 0.29 mmol) till orange color persisted. The reaction mixture was stirred for 45 minutes before being quenched with isopropyl alcohol until green color persisted. It was dried (sodium sulfate) and concentrated in vacuo. Chromatography over silica gel, eluting with hexanes/ethyl acetate with 10% acetic acid as additive, afforded the title compound. $^1$H NMR (500 MHz, CDCl$_3$) δ 5.02 (br s, 1H), 3.96 (d, J=16.8 Hz, 1H), 3.88-3.76 (m, 2H), 3.55-3.37 (m, 3H), 2.48-2.28 (m, 1H), 2.30-2.11 (m, 1H), 1.47-1.26 (m, 9H), 1.32-1.22 (m, 9H); LC-MS: m/z 360.1 (M+H).

Example 123

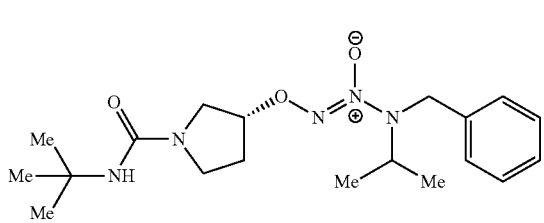 [SMILES: CC(C)N(Cc1ccccc1)/[N+]([O-])=N/O[C@@H]1CCN(C(=O)NC(C)(C)C)C1]

O$^2$-[(3R)-1-(tert-butylcarbamoyl)pyrrolidin-3-yl]1-(N-benzyl-N-isopropylamino)diazen-1-ium-1,2-diolate The title compound was made by following the procedures described in EXAMPLE 120, substituting N-benzyl-N-isopropylamine for N-tert-butyl-N-propylamine. $^1$H NMR (500 MHz, CDCl$_3$) δ 7.34-7.26 (m, 5H), 4.73-4.64 (m, 1H), 4.16 (d, J=13.0 Hz, 1H), 4.13 (d, J=13.0 Hz, 1H), 3.89 (s, 1H), 3.66 (septet, J=6.4 Hz, 1H). 3.38 (dd, J=11.9, 5.0 Hz, 1H), 3.31 (td, J=9.1, 2.6 Hz, 1H), 3.23 (d, J=11.9 Hz, 1H), 3.17 (td, J=9.6, 6.9 Hz, 1H), 1.88 (dtd, J=13.9, 9.3, 4.9 Hz, 1H), 1.81-1.75 (m, 1H), 1.33 (s, 9H), 1.24 (d, J=6.4 Hz, 3H). 1.22 (d, J=6.4 Hz, 3H); LC-MS: m/z 378.2 (M+H).

Example 124

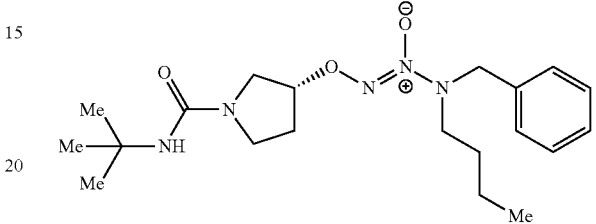

O$^2$-[(3R)-1-(tert-butylcarbamoyl)pyrrolidin-3-yl]1-(N-benzyl-N-butylamino)diazen-1-ium-1,2-diolate The title compound was made by following the procedures described in EXAMPLE 120, substituting N-benzyl-N-butylamine for sodium 1-(N-tert-butyl-N-propylamine. $^1$H NMR (500 MHz, CDCl$_3$) δ 7.38-7.24 (m, 5H), 4.79-4.71 (m, 1H), 4.17 (s, 2H), 3.93 (br s, 1H), 3.44 (dd, J=12.0, 5.0 Hz, 1H), 3.39-3.31 (m, 2H), 3.24 (td, J=9.4, 7.2 Hz, 1H), 3.20-3.07 (m, 2H), 2.00-1.87 (m, 2H), 1.48 (quintet, J=7.4 Hz, 2H), 1.45-1.26 (m, 11H), 0.90 (t, J=7.3 Hz, 3H); LC-MS: m/z 392.2 (M+H).

Example 125

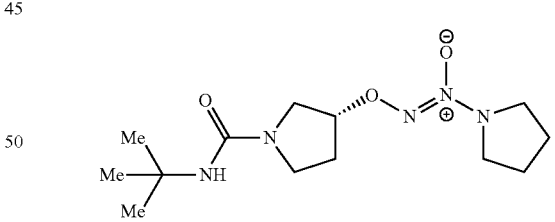

O$^2$-[(3R)-1-(tert-butylcarbamoyl)pyrrolidin-3-yl]1-(pyrrolidin-1-yl)diazen-1-ium-1,2-diolate The title compound was made by following the procedures described in EXAMPLE 120, substituting pyrrolidine for N-tert-butyl-N-propylamine. $^1$H NMR (500 MHz, CDCl$_3$) δ 4.86 (t, J=4.5 Hz, 1H), 3.71 (d, J=12.0 Hz, 1H), 3.58 (dd, J=12.0, 4.8 Hz, 11H), 3.54 (t, J=6.4 Hz, 4H), 3.46 (td, J=9.6, 6.8 Hz, 1H), 3.42 (td, J=9.0, 2.6 Hz, 1H), 2.33 (dd, J=13.9, 6.5

Hz, 1H), 2.15 (dtd, J=13.9, 9.5, 5.0 Hz, 1H), 1.98-1.92 (m, 4H), 1.35 (s, 9H); LC-MS: m/z 322.1 (M+Na).

Example 126

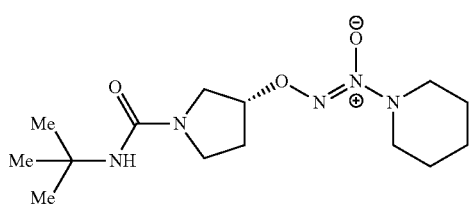 [SMILES: CC(C)(C)NC(=O)N1CC[C@@H](O/N=[N+](\[O-])N2CCCCC2)C1]

$O^2$-[(3R)-1-(tert-butylcarbamoyl)pyrrolidin-3-yl]1-(piperidin-1-yl)diazen-1-ium-1,2-diolate The title compound was made by following the procedures described in EXAMPLE 120, substituting piperidine for N-tert-butyl-N-propylamine. $^1$H NMR (500 MHz, CDCl$_3$) δ 4.91 (t, J=4.6 Hz, 1H), 3.70 (d, J=12.2 Hz, 1H), 3.59 (dd, J=12.1, 4.8 Hz, 1H), 3.47-3.38 (m, 2H), 3.34 (t, J=5.5 Hz, 4H), 2.36-2.30 (m, 1H), 2.17 (dtd, J=13.9, 9.5, 5.1 Hz, 1H), 1.75 (quintet, J=5.7 Hz, 4H), 1.51 (quintet, J=5.9 Hz, 2H), 1.35 (s, 9H); LC-MS: m/z 336.1 (M+Na).

Example 127

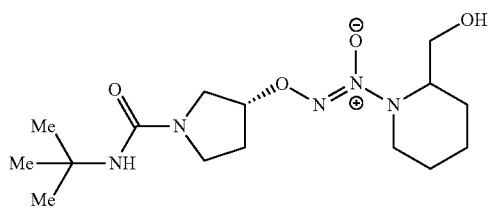 [SMILES: CC(C)(C)NC(=O)N1CC[C@@H](O/N=[N+](\[O-])N2CCCCC2CO)C1]

$O^2$-[(3R)-1-(tert-butylcarbamoyl)pyrrolidin-3-yl]-1-[2-(hydroxymethyl)piperidin-1-yl]diazen-1-ium-1,2-diolate The title compound was made by following the procedures described in EXAMPLE 120, substituting (+)-piperidin-2-ylmethanol for N-tert-butyl-N-propylamine. Chromatography over silica gel, eluting with hexanes/ethyl acetate, afforded the title compound as separated diastereomers. Less polar diastereomer: $^1$H NMR (500 MHz, CDCl$_3$) δ 4.94 (t, J=4.0 Hz, 1H), 4.10 (d, J=12.7 Hz, 1H), 3.54-3.43 (m, 3H), 3.40-3.35 (m, 2H), 3.28-3.19 (m, 2H), 3.15-3.10 (m, 1H), 2.39 (ddd, J=14.2, 7.1, 2.0 Hz, 1H), 2.20 (dtd, J=14.2, 9.6, 4.7 Hz, 1H), 1.87-1.69 (m, 6H), 1.33 (s, 9H); LC-MS: m/z 344.2 (M+H). More polar diastereomer: $^1$H NMR (500 MHz, CDCl$_3$) δ 4.97 (t, J=4.6 Hz, 1H), 3.72 (d, J=12.3 Hz, 1H), 3.61-3.53 (m, 2H), 3.53-3.34 (m, 4H), 3.28-3.20 (m, 2H), 2.38-2.29 (m, 1H), 2.23-2.12 (m, 1H), 1.84-1.67 (m, 6H), 1.34 (s, 9H); LC-MS: m/z 344.2 (M+H).

Activity

Compounds of the invention were evaluated for blood pressure reduction efficacy using the following canine telemetry protocol described below.

Male beagle dogs (approximately 1-3 years old) with a body weight of between 10 and 16 kg were surgically implanted with DSI radiotelemetry devices (model: TL11M2-D70-PCT). Briefly, under an inhalant anesthesia, isoflurane/oxygen mixture (1-3.5%/to effect), the body of the telemetry device was positioned and secured intra-abdominally. Subsequently, the arterial catheter of the telemetry device was passed subcutaneously to the inguinal area and introduced into the femoral artery and advanced to the level of the descending aorta. The catheter was secured with 2-0 silk ligatures. The muscle and underlying fascia was closed over the catheter using absorbable suture and the skin was closed using non-absorbable suture. The animals were allowed a minimum recovery period of 2 weeks between surgery and the evaluation of test compounds.

Compound evaluation consisted of a 3 day paradigm at a 3 mg/kg dose. On the first day, no compounds were administered during a 24 hour period of baseline data collection. Blood pressure and heart rate data were collected continuously for one minute periods at 10 minute intervals. On the days of compound administration half the animals received test article with the other half receiving the vehicle used for compound formulation. All test materials were administered by oral gavage in a volume of 1 mL/kg. Data are expressed either as raw values (mm Hg or beats per minute) or as the change from baseline (average value for about 12 hours in low activity period prior to dosing). Change is SBP (systolic blood pressure) and PP (pulse pressure) over time is shown below:

|  | ΔSBP (mm Hg) | | | ΔPP (mm Hg) | | |
| --- | --- | --- | --- | --- | --- | --- |
| Example | 1-6 h | 6-12 h | 12-18 h | 1-6 h | 6-12 h | 12-18 h |
| 1 | −16 | −15 | −11 | −16 | −17 | −15 |
| 6 | −25 | −16 | −9 | −19 | −17 | −15 |
| 28 | −21 | −14 | −7 | −12 | −10 | −5 |
| 32 | −32 | −16 | −5 | −23 | −15 | −10 |
| 48 | −16 | −12 | −11 | −17 | −16 | −15 |
| 59 | −19 | −18 | −17 | −17 | −16 | −15 |
| 64 | −13 | −12 | −11 | −12 | −15 | −13 |

The exemplified compounds reduced blood pressure over the indicated time periods. Examples 1-6, 12, 14, 16, 23, 28, 30, 32-36, 38, 40-49, 51-56. 58-67, 70-73, 76, 80, 81, 88, 90, 92, 94, 100, 101,103-108, 111-113, 115-119, 125, 126 were also tested in the canine telemetry protocol, and dropped blood pressure by at least 5 mm Hg over a 1-6 hour period of time.

What is claimed is:
1. A compound having the formula I:

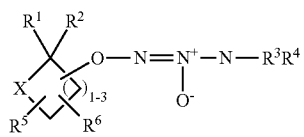

or a pharmaceutically acceptable salt thereof, wherein

X is O or NR⁷;

R¹ is hydrogen, —C(O)OC₁₋₆alkyl, or —C(O)OH, or together with R², forms =O;

R² is hydrogen, or together with R¹, forms =O;

R³ and R⁴ are independently
- —C₁₋₆alkyl,
- —CD₂C₁₋₅alkyl,
- —C₂₋₅alkylene-OH,
- —C₂₋₅alkylene-O—C(O)C₁₋₆alkyl,
- —C₁₋₆alkylene-aryl, or
- —CH₂CH=CH₂,
- or, together with the nitrogen atom to which they are attached, form a 4- to 7-membered heterocyclic ring containing one nitrogen atom and 0 or 1 oxygen atoms, wherein said ring is unsubstituted or mono-, di- or tri-substituted with halogen or —C₁₋₆alkyl;

R⁵ and R⁶, which are attached to any available carbon ring atom, are independently hydrogen,
- —C₁₋₆alkyl,
- —C(O)OC₁₋₆alkyl,
- —C(O)OH,
- aryl,
- or R⁵ and R⁶, when they are attached to the same carbon atom, together form =O;

R⁷ is
- hydrogen,
- deuterium,
- —C₁₋₆alkyl,
- —C₁₋₆alkylene-aryl,
- —C₁₋₆alkyleneC(O)O—C₁₋₆alkyl,
- —C₁₋₆alkyleneCF₃,
- —CN,
- —C(O)O—C₁₋₆alkyl,
- —C(O)C₁₋₆alkyl,
- —C(O)OC₃₋₆carbocycle,
- —C(O)CHF₂,
- —C(O)CHF₃,
- —C(O)CH₂OH,
- —C(O)aryl,
- —C(O)C₁₋₆alkyleneOHC(O)C₃₋₆carbocycle,
- —C(O)NH₂,
- —C(O)NHC₁₋₆alkyl,
- —C(O)heterocycle,
- —C(O)NHC₃₋₆carbocycle,
- —C(O)N(C₁₋₆alkyl)C₁₋₆alkyl,
- —C(O)NHSO₂aryl,
- —SOC₁₋₆alkyl,
- —SO₂C₁₋₆alkyl,
- —SO₂CF₃,
- —SO₂aryl,
- —SO₂heteroaryl,
- aryl,
- heteroaryl,
- heterocycle, or
- —C₃₋₆carbocycle;

wherein aryl, alkyl, carbocycle, heteroaryl, and heterocycle are unsubstituted or substituted with 1, 2, 3 or 4 groups independently selected from —CN, halogen, —CF₃, =O, —C(O)OC₁₋₆alkyl or —O—C₁₋₆alkyl.

2. A compound of claim 1, having the formula Ia

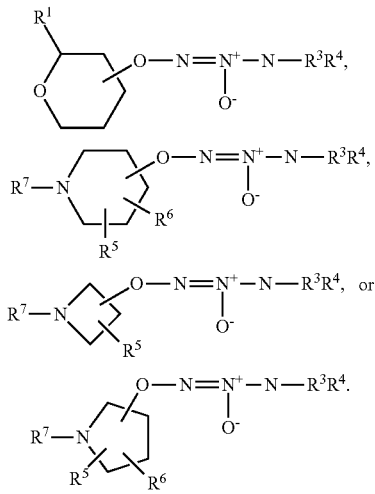

or a pharmaceutically acceptable salt thereof.

3. A compound of claim 1, having the formula Ib

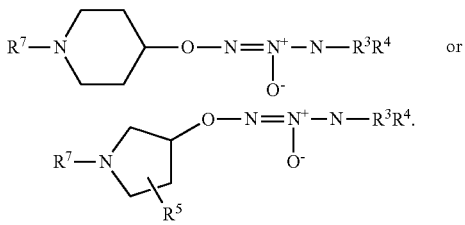

or a pharmaceutically acceptable salt thereof.

4. A compound of claim 1, wherein R¹ is hydrogen, —C(O)OH, or —C(O)OCH₃, or a pharmaceutically acceptable salt thereof.

5. A compound of claim 1, wherein R² is hydrogen, or a pharmaceutically acceptable salt thereof.

6. A compound of claim 1, wherein R³ is —C(CH₃)₃ or —CH₂CH₃, or a pharmaceutically acceptable salt thereof.

7. A compound of claim 1, wherein R⁴ is —CH₃, —CH₂CH₃, —CH₂CH₂CH₃, —CH₂CH₂CH₂CH₃, —CH₂CH₂-phenyl, —CD₂CH₃, —CH₂CH₂OH, or —CH₂CH₂OC(O)CH₃ or a pharmaceutically acceptable salt thereof.

8. A compound of claim 1, wherein R⁵ is hydrogen, —CH₃, C(O)OCH₃, —C(O)OH, phenyl, or a pharmaceutically acceptable salt thereof.

9. A compound of claim 1, wherein R⁶ is hydrogen or —CH₃, or a pharmaceutically acceptable salt thereof.

10. A compound of claim 1, wherein R⁵ and R⁶ together form =O, or a pharmaceutically acceptable salt thereof.

11. A compound of claim 1, or a pharmaceutically acceptable salt thereof, wherein R⁷ is hydrogen, —CH₃, —CH₂CF₃, —CH₂C₆H₅, —CH(CH₃)C₆H₅, —CH(CH₃)C(O)OCH₂CH₃, —CH₂CH(CH₂CH₃)₂, —CH(CH₂CH₃)₂, —C(CH₃)₂C₆H₅, —C(CH₃)₃, —CN, —CH₂CH(CH₃)₂, or

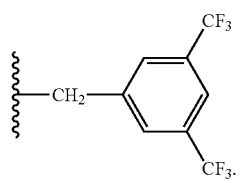 [SMILES: *Cc1cc(C(F)(F)F)cc(C(F)(F)F)c1]

12. A compound of claim 1, or a pharmaceutically acceptable salt thereof, wherein $R^7$ is —C(O)OC(CH$_3$)$_3$, —C(O)CH$_3$, —C(O)CF$_3$, —C(O)OCH$_2$CH$_3$, —C(O)OC$_6$H$_{11}$, —C(O)CHF$_2$, —C(O)C$_6$H$_5$, —C(O)CH$_2$OH, —C(O)C$_3$H$_5$, —C(O)C(CH$_3$)$_3$, —C(O)NH$_2$, —C(O)NHC(CH$_3$)$_3$, —C(C)NHC$_6$H$_{11}$, —C(O)N(CH$_3$)C(CH$_3$)$_3$, —C(O)SC(CH$_3$)$_3$, —C(C)NHSO$_2$C$_6$H$_5$,

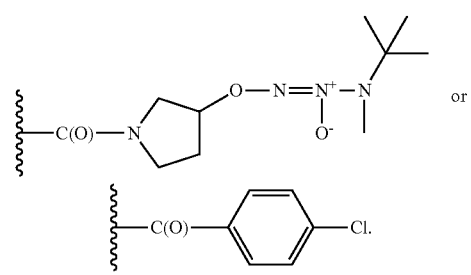

13. A compound of claim 1, or a pharmaceutically acceptable salt thereof, wherein $R^7$ is —SO$_2$CH$_3$, —SO$_2$C$_6$H$_5$, —SO$_2$C(CH$_3$)$_3$, —SOC(CH$_3$)$_3$, —SO$_2$CF$_3$,

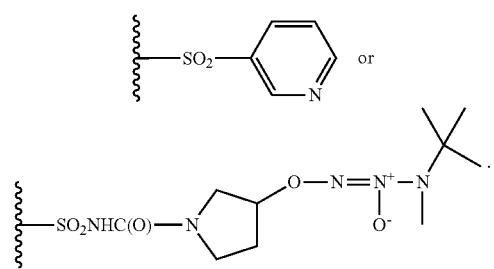

14. A compound of claim 1, or a pharmaceutically acceptable salt thereof, wherein $R^7$ is
—C$_6$H$_5$,

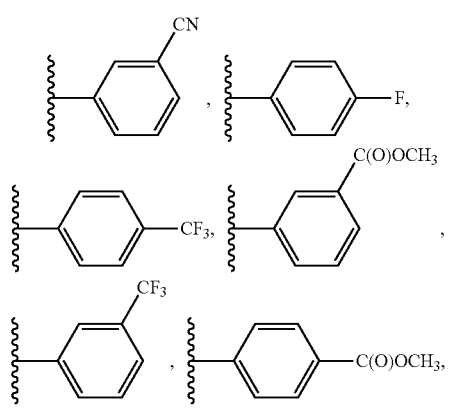

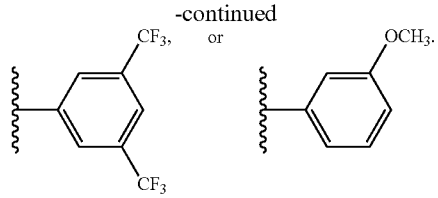

15. A compound of claim 1, or a pharmaceutically acceptable salt thereof, wherein $R^7$ is

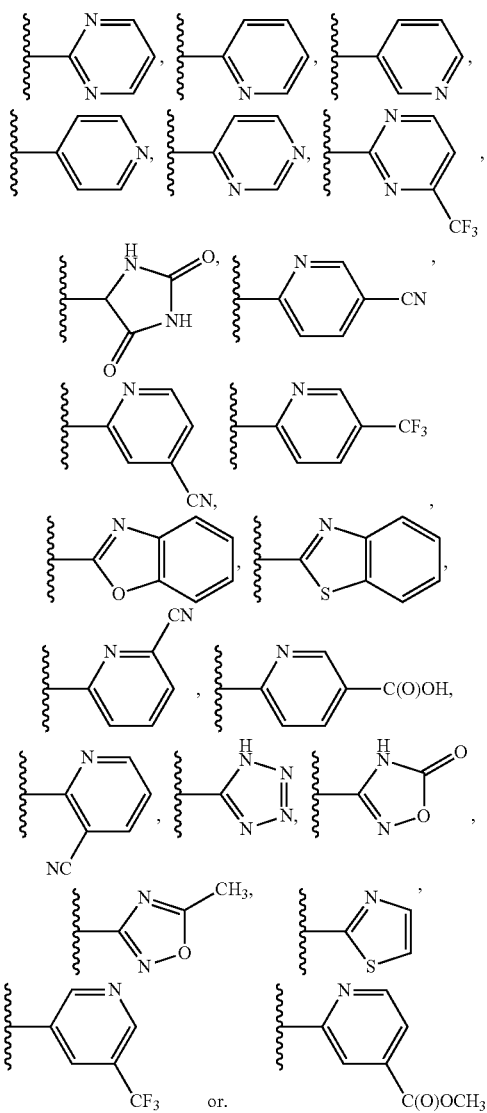

16. A compound of claim 1, or a pharmaceutically acceptable salt thereof, wherein $R^7$ is —C$_6$H$_{11}$ or —C$_5$H$_9$.

17. A compound of claim 1, which is
O$^2$-[(3R)-1-(tert-butoxycarbonyl)pyrrolidin-3-yl]1-(N-tert-butyl-N-methylamino)diazen-1-ium-1,2-diolate,
O$^2$-[(3S)-1-(tert-butoxycarbonyl)pyrrolidin-3-yl]1-(N-tert-butyl-N-methylamino)diazen-1-ium-1,2-diolate,
O$^2$-[(3R)-1-(tert-butoxycarbonyl)pyrrolidin-3-yl]1-(N-tert-butyl-N-ethylamino)diazen-1-ium-1,2-diolate,
O$^2$-[(3R)-1-(tert-butoxycarbonyl)pyrrolidin-3-yl]1-(N-tert-butyl-N-ethylamino)diazen-1-ium-1,2-diolate, $O^2$[1-(tert-butoxycarbonyl)piperidin-4-yl]1-(N-tert-butyl-N-methylamino)diazen-1-ium-1,2-diolate, $O^2$-[1-(tert-butoxycarbonyl)piperidin-4-yl]1-(N-tert-butyl-N-ethylamino)diazen-1-ium-1,2-diolate, $O^2$-[1-(tert-butoxycarbonyl)piperidin-4-yl]1-(N,N-diethylamino)diazen-1-ium-1,2-diolate, $O^2$-[1-(tert-butoxycarbonyl)piperidin-4-yl]1-(N-tert-butyl-N-propylamino)diazen-1-ium-1,2-diolate, $O^2$-[1-(tert-butoxycarbonyl)piperidin-4-yl]1-(N-butyl-N-tert-butylamino)diazen-1-ium-1,2-diolate, $O^2$-[1-(tert-butoxycarbonyl)piperidin-4-yl]1-(N-tert-butyl-N-phenylethylamino)diazen-1-ium-1,2-diolate, $O^2$-[1-(tert-butoxycarbonyl)piperidin-4-yl]1-[N-tert-butyl-N-(2'-hydroxyethyl)amino]diazen-1-ium-1,2-diolate, (±)-$O^2$[1-(tert-butoxycarbonyl)piperidin-3-yl]1-(N-tert-butyl-N-methylamino)diazen-1-ium-1,2-diolate, $O^2$-[1-(tert-butoxycarbonyl)azetidin-3-yl]1-(N-tert-butyl-N-methylamino)diazen-1-ium-1,2-diolate, $O^2$[1-(tert-butoxycarbonyl)azetidin-3-yl]1-(N-tert-butyl-N-ethylamino)diazen-1-ium-1,2-diolate, $O^2$[(3R)-pyrrolidin-3-yl]1-(N-tert-butyl-N-methylamino)diazen-1-ium-1,2-diolate, $O^2$[(3R)-pyrrolidin-3-yl]1-(N-tert-butyl-N-ethylamino)diazen-1-ium-1,2-diolate, $O^2$-(piperidin-4-yl) 1-(N-tert-butyl-N-ethylamino)diazen-1-ium-1,2-diolate, $O^2$-[(3R)-1-(2-methylpropyl)pyrrolidin-3-yl]1-(N-tert-butyl-N-methylamino)diazen-1-ium-1,2-diolate, $O^2$-[(3R)-1-benzylpyrrolidin-3-yl]1-(N-tert-butyl-N-methylamino)diazen-1-ium-1,2-diolate, (±)-$O^2$-[(3R)-1-(1-phenylethyl)pyrrolidin-3-yl]1-(N-tert-butyl-N-methylamino)diazen-1-ium-1,2-diolate, $O^2$-[(3R)-1-(2-phenylpropan-2-yl)pyrrolidin-3-yl]1-(N-tert-butyl-N-methylamino)diazen-1-ium-1,2-diolate, $O^2$-[(3R)-1-tert-butylpyrrolidin-3-yl]1-(N-tert-butyl-N-methylamino)diazen-1-ium-1,2-diolate, $O^2$-(1-methylpiperidin-4-yl) 1-(N-tert-butyl-N-ethylamino)diazen-1-ium-1,2-diolate, $O^2$-[(3R)-1-(2,2,2-trifluoroethyl)pyrrolidin-3-yl]1-(N-tert-butyl-N-ethylamino)diazen-1-ium-1,2-diolate, $O^2$-[1-(2,2,2-trifluoroethyl)piperidin-4-yl]1-(N-tert-butyl-N-ethylamino)diazen-1-ium-1,2-diolate, $O^2$-(1-benzylpiperidin-4-yl) 1-(N-tert-butyl-N-ethylamino)diazen-1-ium-1,2-diolate, (±)-$O^2$-[1-(1-phenylethyl)piperidin-4-yl]1-(N-tert-butyl-N-ethylamino)diazen-1-ium-1,2-diolate, $O^2$-[(3R)-1-phenylpyrrolidin-3-yl]1-(N-tert-butyl-N-methylamino)diazen-1-ium-1,2-diolate, $O^2$-[(3R)-1-(3-cyanophenyl)pyrrolidin-3-yl]1-(N-tert-butyl-N-methylamino)diazen-1-ium-1,2-diolate, $O^2$-{(3R)-1-[3-(methoxycarbonyl)phenyl]pyrrolidin-3-yl}1-(N-tert-butyl-N-methylamino)diazen-1-ium-1,2-diolate, $O^2$-{(3R)-1-[3-(trifluoromethyl)phenyl]pyrrolidin-3-yl}1-(N-tert-butyl-N-methylamino)diazen-1-ium-1,2-diolate, $O^2$-{(3R)-1-[3,5-bis(trifluoromethyl)phenyl]pyrrolidin-3-yl}1-(N-tert-butyl-N-methylamino)diazen-1-ium-1,2-diolate, $O^2$-[(3R)-1-(1,3-thiazol-2-yl)pyrrolidin-3-yl]1-(N-tert-butyl-N-methylamino)diazen-1-ium-1,2-diolate, $O^2$-[1-(pyridin-2-yl)piperidin-4-yl]1-(N-tert-butyl-N-methylamino)diazen-1-ium-1,2-diolate, $O^2$-[1-(pyridin-3-yl)piperidin-4-yl]1-(N-tert-butyl-N-methylamino)diazen-1-ium-1,2-diolate, $O^2$-(1-phenylpiperidin-4-yl) 1-(N-tert-butyl-N-ethylamino)diazen-1-ium-1,2-diolate, $O^2$-[1-(3-cyanophenyl)piperidin-4-yl]1-(N-tert-butyl-N-ethylamino)diazen-1-ium-1,2-diolate, $O^2$-[1-(6-cyanopyridin-2-yl)piperidin-4-yl]1-(N-tert-butyl-N-ethylamino)diazen-1-ium-1,2-diolate, $O^2$-[1-(5-cyanopyridin-2-yl)piperidin-4-yl]1-(N-tert-butyl-N-ethylamino)diazen-1-ium-1,2-diolate, $O^2$-[1-(4-cyanopyridin-2-yl)piperidin-4-yl]1-(N-tert-butyl-N-ethylamino)diazen-1-ium-1,2-diolate, $O^2$-[1-(3-cyanopyridin-2-yl)piperidin-4-yl]1-(N-tert-butyl-N-ethylamino)diazen-1-ium-1,2-diolate, $O^2$-[(3R)-1-(tert-butylcarbamoyl)pyrrolidin-3-yl]1-(N-tert-butyl-N-methylamino)diazen-1-ium-1,2-diolate, $O^2$-[(3R)-1-(tert-butylcarbamoyl)pyrrolidin-3-yl]1-(N-tert-butyl-N-ethylamino)diazen-1-ium-1,2-diolate, $O^2$-{(3R)-2-oxo-1-[4-(trifluoromethyl)phenyl]pyrrolidin-3-yl}1-(N-tert-butyl-N-methylamino)diazen-1-ium-1,2-diolate, $O^2$-[(3R)-1-acetylpyrrolidin-3-yl]1-(N-tert-butyl-N-methylamino)diazen-1-ium-1,2-diolate, $O^2$-(1-acetylpiperidin-4-yl) 1-(N-tert-butyl-N-ethylamino)diazen-1-ium-1,2-diolate, $O^2$-[1-(phenylcarbonyl)piperidin-4-yl]1-(N-tert-butyl-N-ethylamino)diazen-1-ium-1,2-diolate, $O^2$-[1-(hydroxyacetyl)piperidin-4-yl]1-(N-tert-butyl-N-ethylamino)diazen-1-ium-1,2-diolate, $O^2$-[1-(difluoroacetyl)piperidin-4-yl]1-(N-tert-butyl-N-ethylamino)diazen-1-ium-1,2-diolate, $O^2$[1-(trifluoroacetyl)piperidin-4-yl]1-(N-tert-butyl-N-ethylamino)diazen-1-ium-1,2-diolate, $O^2$[1-(phenylcarbonyl)azetidin-3-yl]1-(N-tert-butyl-N-methylamino)diazen-1-ium-1,2-diolate, $O^2$-[(3R)-1-(methylsulfonyl)pyrrolidin-3-yl]1-(N-tert-butyl-N-methylamino)diazen-1-ium-1,2-diolate, $O^2$-[(3R)-1-(tert-butylsulfonyl)pyrrolidin-3-yl]1-(N-tert-butyl-N-methylamino)diazen-1-ium-1,2-diolate,

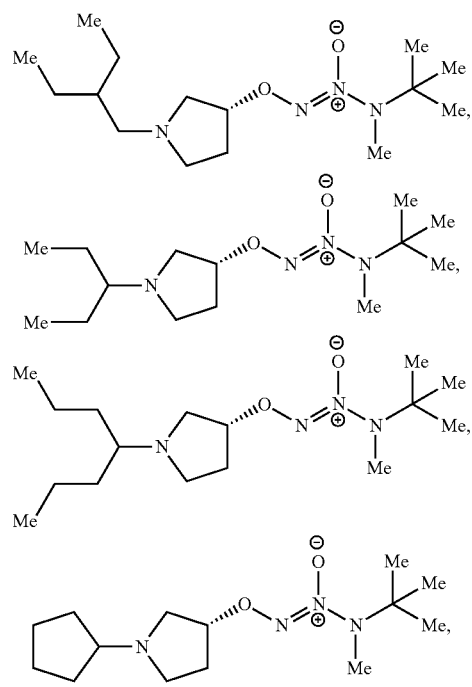

-continued

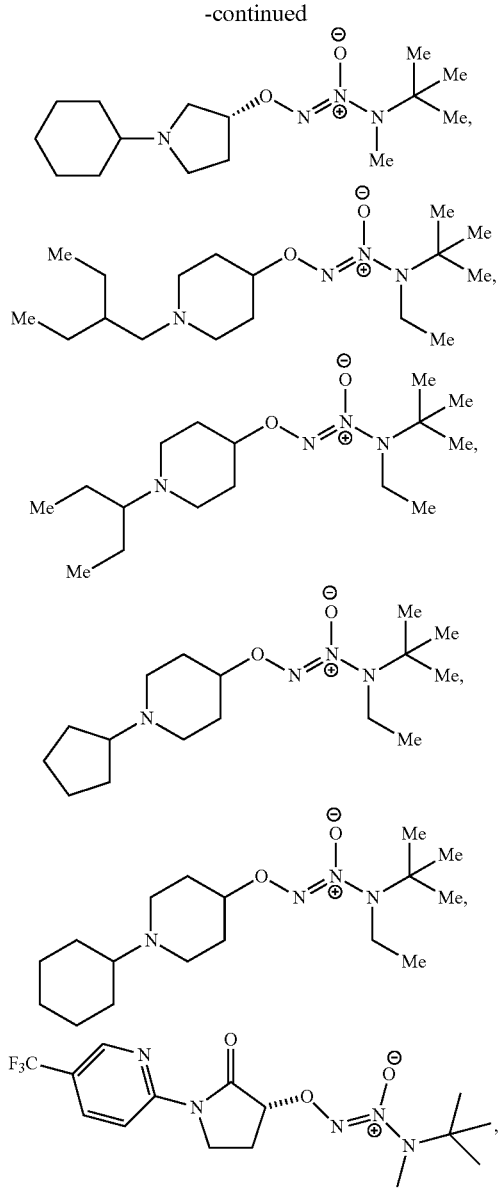

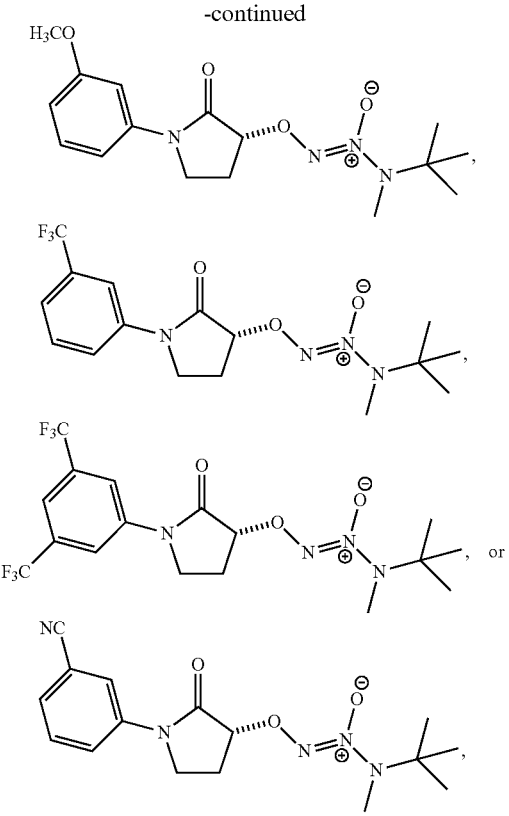

or a pharmaceutically acceptable salt thereof.

18. A pharmaceutical composition comprising a compound of claim 1 and a pharmaceutically acceptable carrier.

19. A pharmaceutical composition comprising a compound of claim 17 and a pharmaceutically acceptable carrier.

20. A pharmaceutical composition comprising a compound of claim 17, a diuretic, and a pharmaceutically acceptable carrier.

21. A method for treating hypertension in a patient which comprises administering to the patient a therapeutically effective amount of the composition of claim 20.

* * * * *